US012594140B2

(12) United States Patent
Nie et al.

(10) Patent No.: US 12,594,140 B2
(45) Date of Patent: Apr. 7, 2026

(54) HEAD BRACE WITH ADJUSTABLE-LENGTH CONNECTOR AND FIXATION CONNECTOR THEREOF

(71) Applicant: The First Affiliated Hospital Of Ningbo University, Ningbo (CN)

(72) Inventors: Sheng Nie, Ningbo (CN); Jie Sun, Ningbo (CN); Yi Huang, Ningbo (CN); Xiang Gao, Shanghai (CN)

(73) Assignee: The First Affiliated Hospital Of Ningbo University, Ningbo (CN)

( * ) Notice: Subject to any disclaimer, the term of this patent is extended or adjusted under 35 U.S.C. 154(b) by 0 days.

(21) Appl. No.: 19/090,316

(22) Filed: Mar. 25, 2025

(65) Prior Publication Data

US 2025/0228641 A1 Jul. 17, 2025

Related U.S. Application Data

(63) Continuation of application No. PCT/CN2023/120091, filed on Sep. 20, 2023.

(30) Foreign Application Priority Data

Sep. 28, 2022 (CN) .......................... 202211187069.0
Sep. 28, 2022 (CN) .......................... 202211187090.0

(51) Int. Cl.
A61B 90/14 (2016.01)
A61G 13/12 (2006.01)

(52) U.S. Cl.
CPC ............ *A61B 90/14* (2016.02); *A61G 13/121* (2013.01)

(58) Field of Classification Search
None
See application file for complete search history.

(56) References Cited

U.S. PATENT DOCUMENTS

| | | | | |
|---|---|---|---|---|
| 4,617,925 A | * | 10/1986 | Laitinen ................. | A61B 90/14 |
| | | | | 606/130 |
| 4,667,660 A | * | 5/1987 | Eingom ............... | A61H 1/0218 |
| | | | | 24/64 |
| 5,171,296 A | * | 12/1992 | Herman ................. | A61B 90/14 |
| | | | | 602/17 |
| 5,387,220 A | * | 2/1995 | Pisharodi ............... | A61B 90/14 |
| | | | | 128/898 |
| 5,423,832 A | * | 6/1995 | Gildenberg ............ | A61B 90/10 |
| | | | | 606/130 |

(Continued)

*Primary Examiner* — William A. Rivera
(74) *Attorney, Agent, or Firm* — Che-Yang Chen

(57) ABSTRACT

This invention provides a head brace with an adjustable-length connector and a fixation connector. The head brace with the adjustable-length connector includes a head brace and a connector. The connector is installed to the head brace, so as to fix medical equipments. The connector includes an outer cover body, an inner core body, a reversible structure, and a fixation rope body. The outer cover body is sleeved out of the inner core body. The reversible structure is installed on the inner core body. The fixation rope body is suitable for being connected to the outer cover body and the inner core body, so as to tighten the fixation rope body by the forward rotation of the inner core body relative to the outer cover body, and to realize the relax the fixation rope body by the reversible structure, so as to realize the adjustable length of the fixation rope body.

7 Claims, 37 Drawing Sheets

(56)         References Cited

U.S. PATENT DOCUMENTS

| | | | | |
|---|---|---|---|---|
| 7,730,563 | B1 * | 6/2010 | Sklar ..................... | A61G 13/121 |
| | | | | 5/640 |
| 8,845,654 | B2 * | 9/2014 | Hong ..................... | A61B 90/14 |
| | | | | 606/56 |
| 10,307,219 | B2 * | 6/2019 | Yang ....................... | A61B 90/14 |
| 11,653,710 | B2 * | 5/2023 | Lu ............................ | A42B 3/08 |
| | | | | 2/418 |
| 11,700,902 | B2 * | 7/2023 | Roberts ................. | A42B 3/145 |
| | | | | 2/421 |
| 2013/0081636 | A1 * | 4/2013 | Schuele ................ | A61B 90/14 |
| | | | | 128/845 |
| 2013/0239303 | A1 * | 9/2013 | Cotterman ............ | A42B 3/324 |
| | | | | 2/417 |
| 2014/0024925 | A1 * | 1/2014 | Piferi .................... | A61B 5/055 |
| | | | | 600/415 |
| 2023/0076366 | A1 * | 3/2023 | Farnan ................. | A61B 6/0421 |
| 2023/0225446 | A1 * | 7/2023 | Pritz ..................... | A42B 3/142 |
| | | | | 2/417 |

* cited by examiner

106—

106

1061

1070

1081

1082

1083

1084

10841

1084

10842

106B

1076

1070   1081

1076

1083
1082
10841
1084
10842
1082
1083

1090

HEAD BRACE WITH ADJUSTABLE-LENGTH CONNECTOR AND FIXATION CONNECTOR THEREOF

CROSS REFERENCE OF RELATED APPLICATION

This is a Continuation Application of PCT/CN2023/120091, filed Sep. 20, 2023, which claims priority under 35 U.S.C. 119 (a-d) to Chinese application numbers 202211187090.0, filed Sep. 28, 2022, and 202211187069.0, filed Sep. 28, 2022, the afore-mentioned patent applications are hereby incorporated by reference in their entireties.

BACKGROUND OF THE PRESENT INVENTION

Field of Invention

The present invention relates to the field of medical devices, and more particular to a head brace with an adjustable-length connector and a fixation connector thereof, that the head brace is adjustable in length and convenient to fix.

Description of Related Arts

In modern life, due to unhealthy diets and bad habits, there are more and more physical diseases, among which the more serious ones are tumor related diseases. Brain tumors, intracranial aneurysms, and vascular malformations are all common brain diseases. When treating tumor related diseases, surgical treatment is the main approach. During intracranial surgery, unstable fixation of the head can affect the surgeon's surgical operation and treatment effectiveness. Therefore, the implementation of cranial surgery must have a fixed position that is convenient for surgical operation, so as to facilitate the exposure of the surgical field of view. At the same time, patient comfort and good posture during surgery are also important conditions for anesthesia and surgical procedures. Therefore, the quality of the fixation device of the head brace in cranial surgery greatly affects the progress of the surgery.

A general cranial fixation frame can be adjusted back and forth, left and right, high and low according to surgical needs, so as to achieve the best head position and posture, facilitate surgical operation and anesthesia management, and play a reliable role in ensuring the smooth progress of surgery. It is an indispensable ideal tool for neurosurgery.

Craniocerebral surgery generally requires general anesthesia. Before the surgery, anesthesia is injected, which can mainly paralyze the skin and avoid pain during the surgery. Then, stent implantation surgery is needed to minimize the damage to the skull. After craniotomy, necrotic tissue needs to be removed, and bruising needs to be cleared before suturing treatment In head surgery, a head brace is needed to secure the patient's head for ease of surgical operation. And in surgery, a large number of small surgical instruments are required to assist the operator in completing intracranial surgery. These small surgical instruments are often fixed to the head brace by winding connectors, making it easy for the surgical instrument operator to access the instruments for surgical operations. Therefore, connectors play an important role in the use of the head brace. The problem with existing connectors is that when fixed by winding, it is difficult to adjust the entire length. The winding cannot be loosened after fixation. In other words, the fixation is irreversible, which can cause inconvenience during use and prevent small instruments from being removed after fixation, resulting in some drawbacks after use.

In a series of surgeries in the head area, it is necessary to fix the patient's head in an ideal position, usually using a head brace to fix the patient's head. Then performing the surgery to facilitate the operation of medical staff and prevent the patient's head from shaking during the surgery, thereby increasing the risk of surgery. After fixing the patient's head with the head brace, small surgical instruments such as surgical knives, catheters, etc. are fixed in specific positions using the fixation connectors on the head brace, making it convenient for medical staff to operate.

The traditional fixation connector is fixed by winding, but this fixing method is unstable and may cause the fixture to fall off due to the weight of the surgical instrument itself, which can increase the risk of surgery. Furthermore, the length adjustment of traditional fixation connectors is difficult and can only achieve unidirectional length adjustment. In other words, when the length of the fixation connector is shortened, it cannot be further extended. Therefore, for fixing different surgical instruments, it cannot reach a reasonable specified position. The range of fixation is relatively narrow.

Therefore, it is necessary to propose a new fixation connector so that the length of the fixation connector can be adjusted during surgery and the adjusted length is convenient for fixation.

SUMMARY OF THE PRESENT INVENTION

The invention is advantageous in that it provides a head brace with an adjustable-length connector, wherein the connector of the head brace comprises a reversible structure and a fixation rope body, wherein the reversible structure enables the length of the fixation rope body to be adjusted arbitrarily when fixing medical devices, making the connector reusable and reducing the use cost of the connector.

Another advantage of the present invention is to provide a head brace with an adjustable-length connector, wherein the length of the fixation rope of the connector can be adjusted arbitrarily, which can conveniently fix medical devices, facilitating the operator to better access the surgical instruments during the operation, enabling the operator to complete the intracranial operation more quickly and shortening the operation time.

Another advantage of the present invention is to provide a head brace with an adjustable-length connector, wherein the reversible structure is installed on the inner core body, which is convenient to use.

Another advantage of the present invention is to provide a head brace with an adjustable-length connector, wherein the reversible structure is simple and not easy to damage.

Another advantage of the present invention is to provide a head brace with an adjustable-length connector, wherein the reversible structure is simple and has a low production cost, which does not increase the production cost and use cost due to the addition of the adjustable-length function.

Another advantage of the present invention is to provide a head brace with an adjustable-length connector, wherein the head brace can fix small surgical equipment through the adjustable-length connector.

Another advantage of the present invention is to provide a head brace with an adjustable-length connector, wherein the head brace can adjust the width of the fixation rope of the connector to fix small surgical equipment to adapt to surgical equipment of different widths.

Another advantage of the present invention is to provide a head brace with an adjustable-length connector, wherein when fixing small surgical equipment, the adjustment of the fixation rope of the head brace is reversible and can be reused many times.

Another advantage of the present invention is to provide a head brace with an adjustable-length connector, wherein the connector of the head brace has a high utilization rate, that can not only fix the surgical instruments in a fixed state but also return the deeply fixed fixation rope by rotation.

Another advantage of the present invention is to provide a head brace with an adjustable-length connector, wherein the head brace can make the ratchet visible or hidden on the surface through the operator's control of the connecting rod.

Another advantage of the present invention is to provide a head brace with an adjustable-length connector, wherein the head brace can accurately fix small surgical equipment in the air for subsequent precise operations.

Another advantage of the present invention is to provide a head brace with an adjustable-length connector, wherein the head brace has a lower use cost compared with traditional connectors and is conducive to mass production.

According to the present invention, the foregoing and other objects and advantages are attained by a head brace with an adjustable-length connector, comprising:

a connector comprising an outer cover body, an inner core body, a reversible structure, and a fixation rope body, wherein the outer cover body is suitable for being sleeved on the outer end of the inner core body, wherein the reversible structure is installed on the inner core body, wherein the fixation rope body is suitable for being connected to the outer cover body and the inner core body, so as to tighten the fixation rope body by the forward rotation of the inner core body relative to the outer cover body, and to relax the fixation rope body by the reverse rotation of the inner core body relative to the outer cover body through the reversible structure, so as to realize the adjustable length of the fixation rope body of the connector; and a head brace comprising a guidance adapter and a head clamp, wherein the guidance adapter is suitable for being installed on the head clamp, wherein the connector is suitable for being installed on the head clamp through the guidance adapter.

According to an embodiment of the present invention, the inner core body comprises a fixation member and a grip member, wherein the fixation member is integrally connected to the grip member.

According to an embodiment of the present invention, the outer cover body has an inner core accommodation cavity, wherein the fixation member of the inner core body is suitable for being accommodated in the outer cover body through the inner core accommodation cavity of the outer cover body.

According to an embodiment of the present invention, the outer cover body has a first fixation hole, a second fixation hole, and a third fixation hole, wherein the first fixation hole, the second fixation hole, wherein the third fixation hole are located on the side end of the outer cover body, wherein the first fixation hole and the second fixation hole are on one side of the outer cover body, wherein the third fixation hole is on the other side of the outer cover body, wherein the first fixation hole and the third fixation hole are on the same axis.

According to an embodiment of the present invention, the fixation member has a first fixation groove and a second fixation groove, wherein the first fixation groove and the second fixation groove are located on the side end of the fixation member, recessed on the surface of the side end of the fixation member, wherein the fixation member further has a first inner hole and a second inner hole, wherein the first inner hole and the second inner hole are respectively located at the bottom of the first fixation groove and the second fixation groove, and horizontally penetrate the fixation member, wherein the first inner hole is on the same axis as the first fixation hole and the third fixation hole, wherein the second inner hole is on the same axis as the second fixation hole, wherein one end of the fixation rope body is suitable for passing through the first fixation hole, the first inner hole, and the third fixation hole, wherein the other end of the fixation rope body is suitable for passing through the second fixation hole and the second inner hole, so that when the inner core body rotates relative to the outer cover body, the two ends of the fixation rope body are respectively wound around the first fixation groove and the second fixation groove, so that the length of the fixation rope is continuously reduced, thereby fixing the medical device on the outer wall of the outer cover body.

According to an embodiment of the present invention, the outer cover body has a clamping groove, which is located on the inner wall of the outer cover body, recessed on the inner wall of the outer cover body and communicating with the inner core accommodation cavity.

According to an embodiment of the present invention, the reversible structure comprises a control member and a connection unit, wherein the control member is installed on the grip member, wherein the clamping member is installed on the fixation member, wherein the clamping member is suitable for engaging with the clamping groove of the outer cover body to achieve fixation.

According to an embodiment of the present invention, the reversible structure further comprises a connection unit, wherein one end of the connection unit is connected to the clamping member, wherein the other end of the connection unit is connected to the control member, so as to drive the movement of the clamping member through the connection unit connected to the control member by controlling the movement of the control member, so as to realize the engagement and separation of the clamping member and the clamping groove, and thus realize the reversible rotation of the inner core body.

According to an embodiment of the present invention, the reversible structure further comprises an elastic element, wherein one end of the elastic element is connected to the clamping member or the connection unit, wherein the other end of the elastic element is connected to the inner core body.

According to an embodiment of the present invention, the fixation member further has an installation hole, wherein the clamping member is suitable for being installed on the fixation member through the installation hole.

According to another aspect of the present invention, the present invention further provides a head brace with an adjustable-length connector, comprising:

a head brace body comprising a base, a plurality of head nails, a plurality of connection members, and a retraction member, wherein the base provides an installation platform, wherein one end of the connection member is connected to the base, wherein the other end one end of the connection member is connected to the head nail and the retraction member, wherein the head nail is suitable for fixing the patient's skull, wherein the retraction member is suitable for retracting the patient's craniocerebrum; and a connector connected to the connection member, wherein the connector comprises a housing, an operation unit, and a fixation rope, wherein the housing has a working cavity, wherein the fixation rope is suitable for being fixed between the housing and the operation unit, wherein the operation unit comprises a second ratchet unit, wherein the housing comprises a first ratchet unit, wherein the first ratchet unit is movably engaged with the second ratchet unit, so as to allow the second ratchet unit to rotate bidirectionally, so as to adjust the coil length between the two fixed points of the fixation rope.

According to an embodiment of the present invention, the housing has a hidden groove and a plurality of extension rods, wherein the hidden groove is located between the inner wall and the outer wall of the housing, wherein the first ratchet unit is suitable for being stored in the hidden groove, wherein the second ratchet unit in the working cavity can rotate bidirectionally, wherein one end of the extension rod is connected to the first ratchet unit, wherein the other end extends out of the upper end of the housing.

According to an embodiment of the present invention, the housing comprises a plurality of limitation members and has a plurality of reservation grooves, wherein the extension rod is suitable for being engaged by the limitation members, wherein the limitation members are located in the hidden groove, wherein the reservation grooves are located on the inner wall of the housing, wherein the first ratchet unit is suitable for passing through the reservation grooves, wherein the reservation grooves communicate with the working cavity and the hidden groove.

According to an embodiment of the present invention, the operation unit has a wire receiving groove. One end of the fixation rope is suitable for being wound and placed in the wire receiving groove, wherein the other end of the fixation rope is suitable for passing through the operation unit, wherein the size of the coil can be adjusted by the rotation of the operation unit.

According to an embodiment of the present invention, the housing comprises a pair of limitation members and has a plurality of reservation grooves, wherein the reservation grooves communicate with the working cavity and the outside, wherein the first ratchet unit is suitable for passing through the reservation grooves, wherein the limitation members are suitable for passing through the reservation grooves to engage the first ratchet unit with the second ratchet unit, thereby limiting the rotation of the operation unit.

According to an embodiment of the present invention, the limitation member comprises a rotation member and an elastic member, wherein one end of the elastic member is connected to the rotation member, wherein the other end of the elastic member is connected to the first ratchet unit, wherein the rotation member is suitable for rotatably passing through the reservation groove, wherein the elastic member movably controls the contact between the first ratchet unit and the second ratchet unit.

According to an embodiment of the present invention, the first ratchet units are distributed on two sides of the housing to control the bidirectional rotation of the second ratchet unit.

Another advantage of the present invention is to provide a fixation connector, wherein the length of the fixation connector can be adjusted and the adjusted length is very convenient to fix, which is convenient for fixing different small surgical instruments during the operation.

Another advantage of the present invention is to provide a fixation connector, wherein the control unit of the fixation connector controls the rotation direction of the ratchet through a guide member, which is convenient for the operator to use.

Another advantage of the present invention is to provide a fixation connector, wherein the fixation connector comprises a control unit, which controls the length of a fixation cable to fix different small surgical instruments.

Another advantage of the present invention is to provide a fixation connector, wherein an elastic element of the fixation connector has a certain stretching limit, wherein when the elastic element reaches the stretching limitation, a stopper abuts against the pawl of the ratchet, wherein the ratchet cannot complete the reverse rotation, thereby stably fixing the length of the fixation cable to meet the need of fixing different small surgical instruments.

Another advantage of the present invention is to provide a fixation connector, wherein the fixation connector controls the contraction of the stopper through a control member, wherein when the ratchet rotates in reverse, the stopper contracts and does not abut against the pawl of the ratchet, completing the reverse rotation of the ratchet and thus controlling the length of the fixation cable.

Another advantage of the present invention is to provide a fixation connector, wherein the fixation connector can adjust the length of the fixation cable and maintain the length, wherein when the fixation cable is subjected to a certain force, it can still ensure that the fixed length remains unchanged.

Another advantage of the present invention is to provide a fixation connector, wherein the fixation connector can provide paragraph-type length adjustment. In other words, every time the ratchet rotates one tooth, the length of the fixation cable changes a little, wherein the changed length can be locked, so that the fixation cable can be fixed in a suitable position.

Another advantage of the present invention is to provide a fixation connector, wherein after fixing, the fixation connector does not expose the fixation cable outside, that does not affect the doctor's operation and prevents tripping the doctor during the operation.

Another advantage of the present invention is to provide a fixation connector, wherein the fixation connector can be reused, so that the length of the fixation cable can be continuously adjusted to reach a suitable use position.

Another advantage of the present invention is to provide a fixation connector, wherein the spacer ring can separate the fixation cable and wind it into different wire-winding cavities, preventing the fixation cable from knotting when it is wound into the wire-winding cavity and facilitating the extraction of the fixation cable from the wire-winding cavity, so that the fixation connector can flexibly adjust the length of the fixation cable and greatly reduce the failure rate of the fixation connector.

Another advantage of the present invention is to provide a fixation connector, wherein the fixation cable is fixed through the relative movement of the core body and the housing by the locking hole and the fixation hole, which is convenient, quick, simple in structure, firm in locking, and convenient for replacement when the fixation cable is worn after repeated use.

Another advantage of the present invention is to provide a fixation connector, wherein the fixation cable can be quickly fixed through the relative movement of the core body and the housing by the wire-sealing hole and the wire-threading hole, wherein the locking is firm and the locking structure is stable.

Another advantage of the present invention is to provide a fixation connector, wherein the grip member is convenient for users to operate, wherein users only need to rotate the grip member to complete the length adjustment of the fixation cable, which is simple and quick and saves time for adjustment during the operation.

Other advantages and features of the present invention are fully embodied through the following detailed description and can be realized through the combination of the means and devices specially pointed out in the appended claims.

According to another aspect of the present invention, the present invention further provides a fixation connector, wherein the fixation connector comprises:

a plug unit;

a housing having a receiving cavity, wherein the plug unit is rotatably installed in the receiving cavity;

a control unit comprising a ratchet, at least one stopper, and a guide member, wherein the ratchet is sleeved on the plug unit, wherein one end of the stopper is connected to the housing, wherein the other end of the stopper abuts against the ratchet to complete the forward rotation of the ratchet, wherein one end of the guide member is pivotally arranged on the housing, wherein the other end is suitable for pushing the stopper away from the ratchet to complete the reverse rotation of the ratchet; and a fixation cable, wherein the two ends of the fixation cable are fixed on the plug unit, wherein the length of the fixation cable for fixing a small surgical instrument is changed by the bidirectional rotation of the ratchet.

According to an embodiment of the present invention, the control unit further comprises at least one elastic element, wherein the elastic element is fixed on the stopper to control one end of the stopper to abut against the ratchet, wherein the stopper, the guide member, and the ratchet are arranged on the same plane.

According to an embodiment of the present invention, the stopper comprises a first stopper and a second stopper, wherein the first stopper and the second stopper are arranged on two sides of the guide member, wherein the first stopper and the second stopper respectively abut against the ratchet to control the bidirectional rotation of the ratchet.

According to an embodiment of the present invention, the plug unit comprises an inner core and a grip portion, wherein the grip portion is connected to the inner core and protrudes from the housing, wherein the ratchet is connected to the inner core to drive the inner core to rotate, wherein the plug unit further comprises a surrounding portion, a fixation portion, and a protruding ring, wherein the protruding ring protrudes outward from the surface of the inner core to divide the inner core into the surrounding portion and the fixation portion, wherein the two ends of the fixation cable are respectively fixed on the surrounding portion and the fixation portion.

According to an embodiment of the present invention, the plug unit further has a limitation hole and a fixation hole, wherein the limitation hole recesses inward from the surface of the surrounding portion and extends through the surrounding portion, wherein the fixation hole recesses inward from the surface of the fixation portion and extends through the fixation portion, wherein the housing comprises an inlet hole and a communication hole, wherein the inlet hole communicates with the limitation hole to fix one end of the fixation cable on the surrounding portion, wherein the communication hole communicates with the fixation hole to fix the other end of the fixation cable on the fixation portion.

According to another aspect of the present invention, the present invention further provides a fixation connector, wherein the fixation connector comprises:

a fixation connector comprising:

a plug unit;

a housing having an receiving cavity, wherein the plug unit is rotatably installed in the receiving cavity;

a control unit comprising a ratchet, at least one stopper, and having at least one installation groove, wherein the ratchet and the stopper are respectively arranged on the housing and the plug unit, wherein one end of the stopper abuts against the ratchet to complete the forward rotation of the ratchet, wherein the installation groove recesses inward from the surface of the plug unit to accommodate the stopper, wherein when the stopper is accommodated in the installation groove, the ratchet can rotate in reverse; and a fixation cable, wherein the two ends of the fixation cable are fixed on the plug unit, wherein the length of the fixation cable for fixing a small surgical instrument is changed by the bidirectional rotation of the ratchet.

According to an embodiment of the present invention, the control unit further comprises a control member and a traction member, wherein the control member is arranged on the housing, and one end of the traction member is connected to the control member, wherein the other end is connected to the stopper to store the stopper in the installation groove.

According to another aspect of the present invention, the present invention further provides a fixation connector, wherein the fixation connector comprises:

a core body;

a housing having an installation groove, wherein the core body is pivotally arranged in the installation cavity; and a ratchet locking component comprising a ratchet, at least one brake member, at least one elastic component, and a reversing component, wherein the ratchet is coaxially installed on the core body, wherein one end of the brake member is pivotally installed on the housing, wherein the other end is biased against the ratchet by the elastic component to limit the ratchet to rotate unidirectionally, wherein the reversing component is installed on one side of the brake member and makes the rotation member move away from the ratchet when the reversing component rotates to unlock the ratchet.

According to an embodiment of the present invention, the core body comprises a grip portion, a main body shaft, and a spacer ring, wherein said grip portion is installed at one end of the main body shaft and protrudes from the housing, wherein said ratchet is installed between the grip portion and the main body shaft to basically close the installation cavity, wherein said spacer ring is set on the main body shaft and divides the installation cavity into a first winding cavity and a second winding cavity.

According to an embodiment of the present invention, the main body shaft further has a locking hole and a sealing hole, wherein the locking hole is located below the spacer ring and connects to the second winding cavity, wherein the sealing hole is located above the spacer ring and connects to the first winding cavity, wherein the housing further has a fixation hole and a pair of threading holes, wherein the fixation hole is set on the side wall of the housing and coaxial with the locking hole, wherein the threading hole is symmetrically set on the side wall of the housing and coaxial with the sealing hole.

According to another aspect of the present invention, the present invention further provides a fixation connector, comprising:

a core body comprising a grip portion, a main body shaft, and a spacer ring;

a housing, wherein the housing has an installation cavity, and the core body is rotatably disposed in the installation cavity;

a ratchet locking component comprising a ratchet, at least one brake member, at least one elastic component, and a reversing component; and a fixation cable, wherein the grip portion is installed at one end of the main body shaft and protrudes from the housing, the ratchet is installed between the grip portion and the main body shaft to basically close the installation cavity, wherein the spacer ring is set on the main body shaft and divides the installation cavity into a first winding cavity and a second winding cavity, wherein the main body shaft also has a locking hole and a sealing hole, wherein the locking hole is located below the spacer ring and connects to the second winding cavity, wherein the sealing hole is located above the spacer ring and connects to the first winding cavity, wherein the housing also has a fixation hole and a pair of threading holes, wherein the fixation hole is set on the side wall of the housing and coaxial with the locking hole, wherein the threading hole is symmetrically set on the side wall of the housing and coaxial with the sealing hole, and one end of the brake component is rotatably installed on the housing, wherein the other end is biased against the ratchet by the elastic component, and the reversing component is installed on one side of the brake member, so that when the reversing component rotates, it pushes the rotating member away from the ratchet, wherein one end of the fixation cable passes through the fixation hole and is inserted into the locking hole, and the other end passes through the threading hole and the sealing hole, wherein in a locked state, the braking member is supported by the elastic component and biased against the ratchet to restrict the one-way rotation of the ratchet, wherein at this time, rotating the core body wraps the fixation cable into the first winding cavity and the second winding cavity, wherein in an unlocked state, rotating the reversing member will wrap the fixation cable into the first winding cavity and the second winding cavity, wherein the brake component is pushed away from the ratchet, and at this time, the core can rotate freely to adjust the length of the fixation cable.

According to an embodiment of the present invention, the ratchet is rigidly connected to the core body, wherein the reversing component is provided on one side of the braking component and supports the braking component, and the elastic component is provided on the other side of the brake member.

According to an embodiment of the present invention, when the fixation connector is in the locked state, the ratchet rotates towards the elastic component to compress the elastic component, causing the brake component to detach from the ratchet, wherein after the ratchet rotates, the brake component is elastically supported and biased against the ratchet by the elastic component, wherein when the ratchet rotates towards the direction of the reversing component, it is restricted by the brake component supported by the reversing component, causing the ratchet to be in an one-way locked state, wherein when the reversing component is unlocked, rotating the reversing component pushes the brake component away from the ratchet, wherein the ratchet can be rotated freely.

According to an embodiment of the present invention, the number of said brake components is two, wherein the number of said elastic components is two, wherein the brake components and said elastic components are symmetrically arranged on both sides of the reversing component, so that the one-way rotation direction of the ratchet can be switched when rotating the reversing component.

According to another aspect of the present invention, the present invention further provides a fixation connector, comprising:

a core body comprising a grip portion, a main body shaft, and a spacer ring;

a housing having an installation cavity, wherein the core body is rotatably disposed in the installation cavity;

a ratchet component comprising a ratchet, a brake member, a reversing component, and a top pin; and a fixation cable, wherein the grip portion is installed at one end of the main body shaft and protrudes from the housing, wherein the ratchet is installed between the grip portion and the main body shaft to basically close the installation cavity, wherein the spacer ring is set on the main body shaft and divides the installation cavity into a first winding cavity and a second winding cavity, wherein the main body shaft also has a locking hole and a sealing hole, wherein the locking hole is located below the spacer ring and connects to the second winding cavity, wherein the sealing hole is located above the spacer ring and connects to the first winding cavity, wherein the housing also has a fixation hole and a pair of threading holes, wherein said fixation hole is set on the side wall of the housing and coaxial with the locking hole, and the threading hole is symmetrically set on the side wall of the housing and coaxial with the sealing hole, wherein one end of the fixation cable is inserted into the locking hole through the fixation hole, and the other end passes through the threading hole and the sealing hole, wherein one end of the top pin is elastically fixed to the reversing component, and the other end is elastically pressed against the brake block and biases the brake block against the ratchet, wherein the brake block has a top tooth surface, a left side surface, a right side surface, a first contact point, and a second contact point, wherein the top tooth surface contacts the ratchet, wherein the reversing component is in a forward rotation state, wherein said top pin contacts the first contact point, which contacts the top tooth surface of the brake block against the ratchet, wherein the left side surface is biased to the housing, causing the ratchet to rotate in the forward direction, and the reverse rotation is restricted, driving the core body to roll the fixation cable into the first winding cavity and the second winding cavity, wherein in the reverse state, said top pin is pressed against the second contact point, and the top tooth surface of the brake block is pressed against the ratchet wheel wherein the right side is biased against the housing, causing the ratchet wheel to rotate in the opposite direction, and the forward rotation is restricted, so that the fixation cable can be adjusted.

Additional advantages and features of the invention will become apparent from the description which follows, and may be realized by means of the instrumentalities and combinations particularly pointing out in the appended claims.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
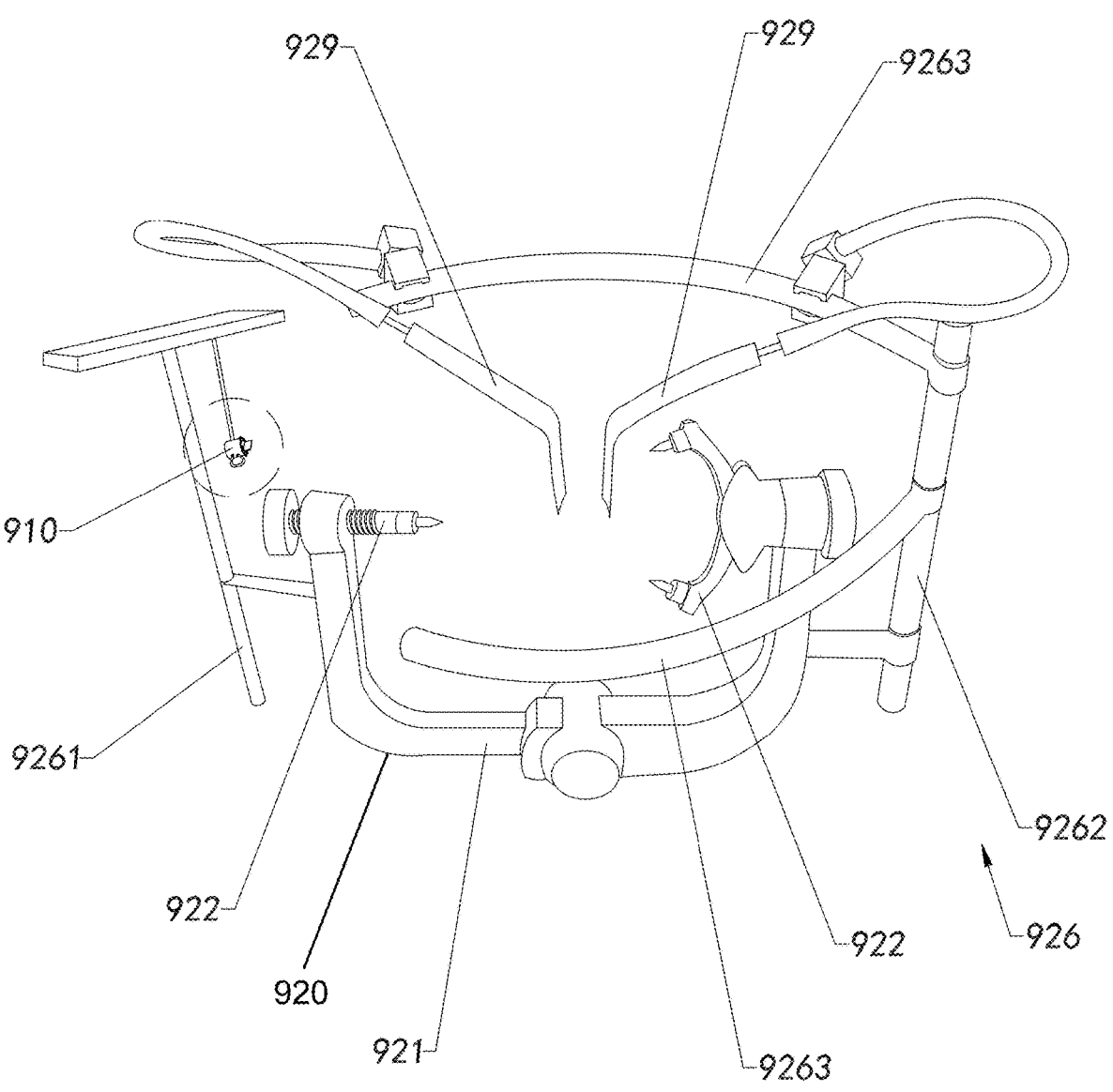
FIG. 1 is a perspective view of a head brace with a length-adjustable connector according to a first preferred embodiment of the present invention.
Figure 2A:
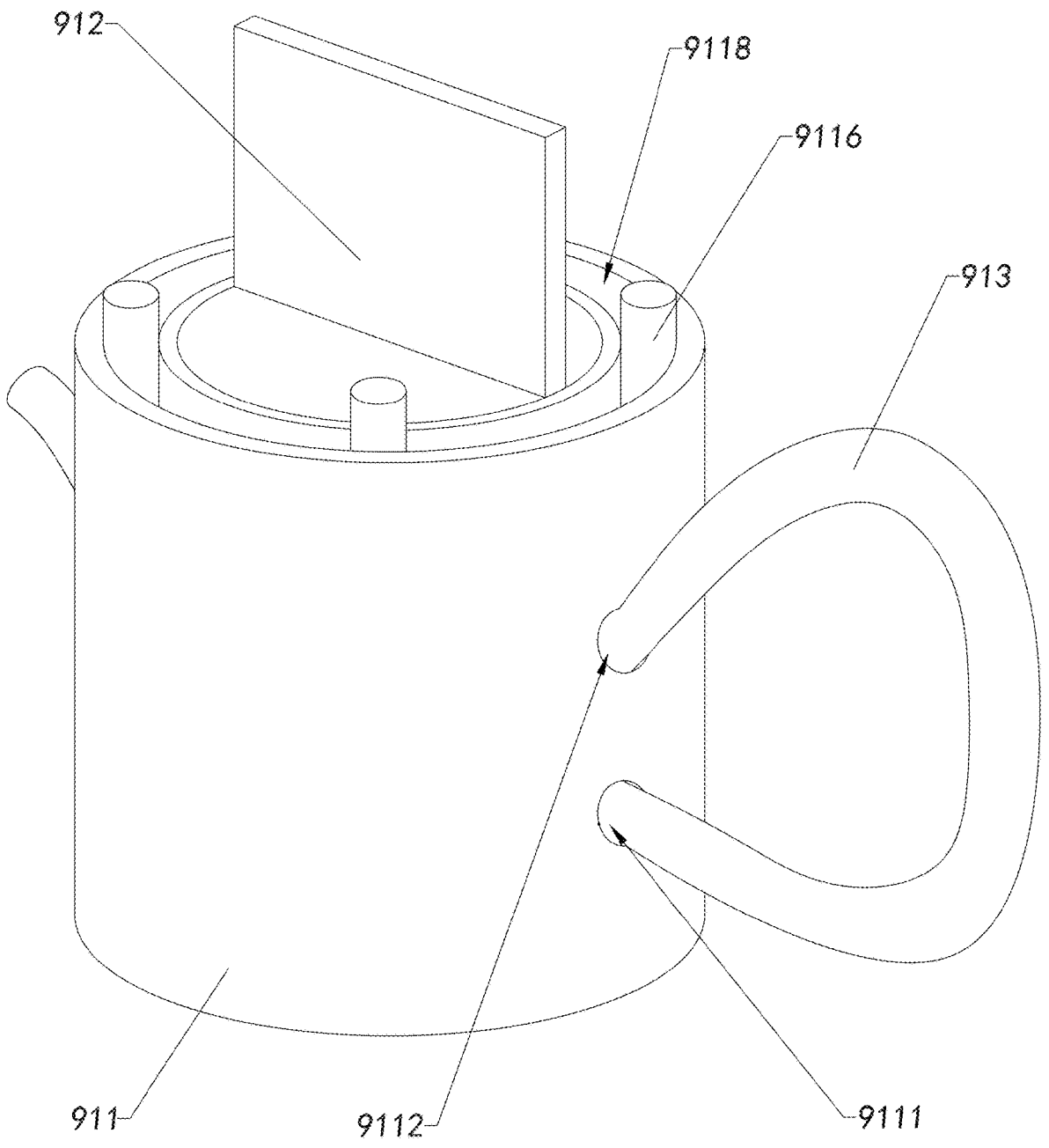
FIG. 2A is a perspective view of the connector of the head brace with the length-adjustable connector according to the above first preferred embodiment of the present invention, illustrating a fixed state of the connector.
Figure 2B:
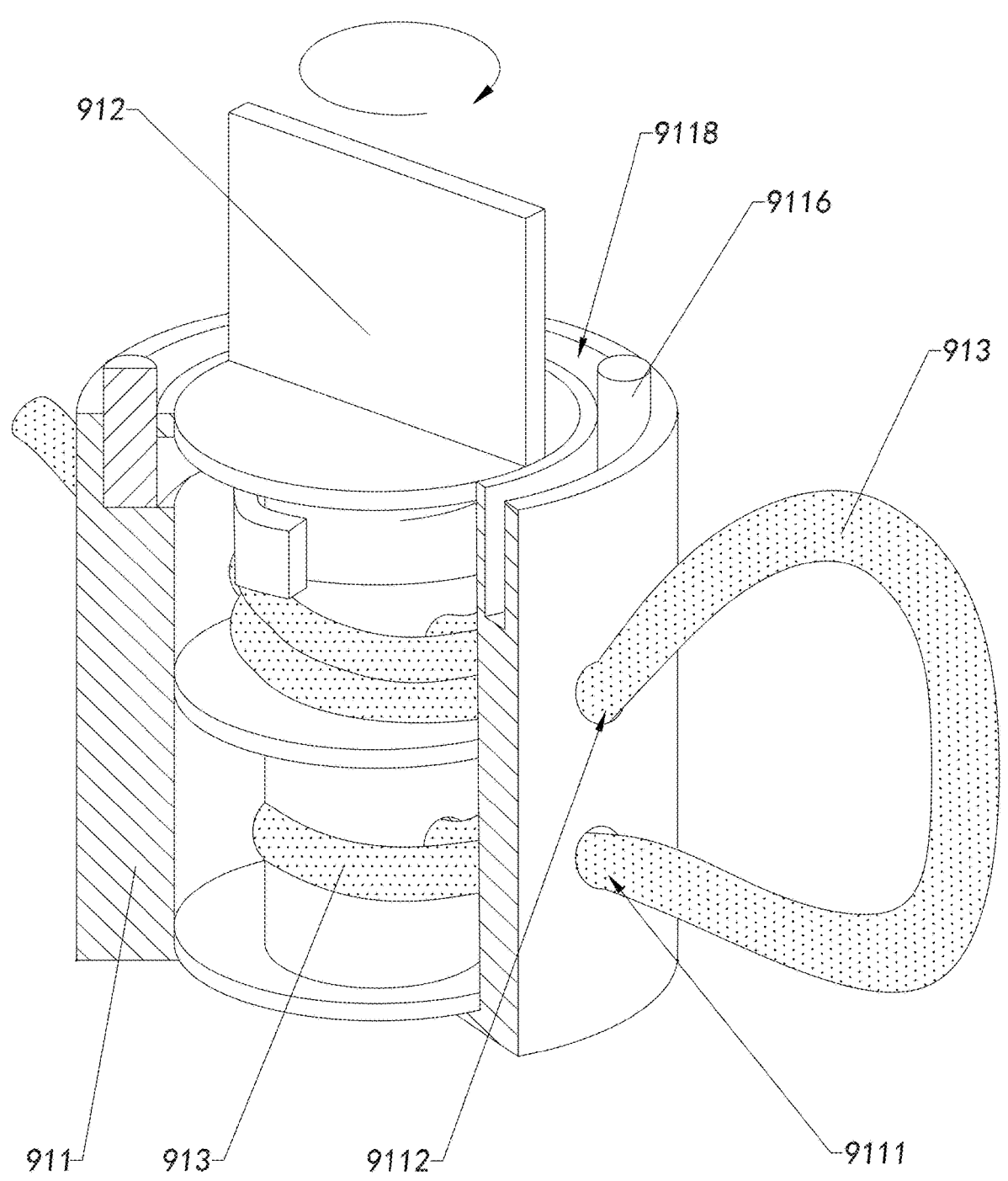
FIG. 2B is a semi sectional view of the connector of the head brace with the length-adjustable connector according to the above first preferred embodiment of the present invention, illustrating the fixed state of the connector.
Figure 3:
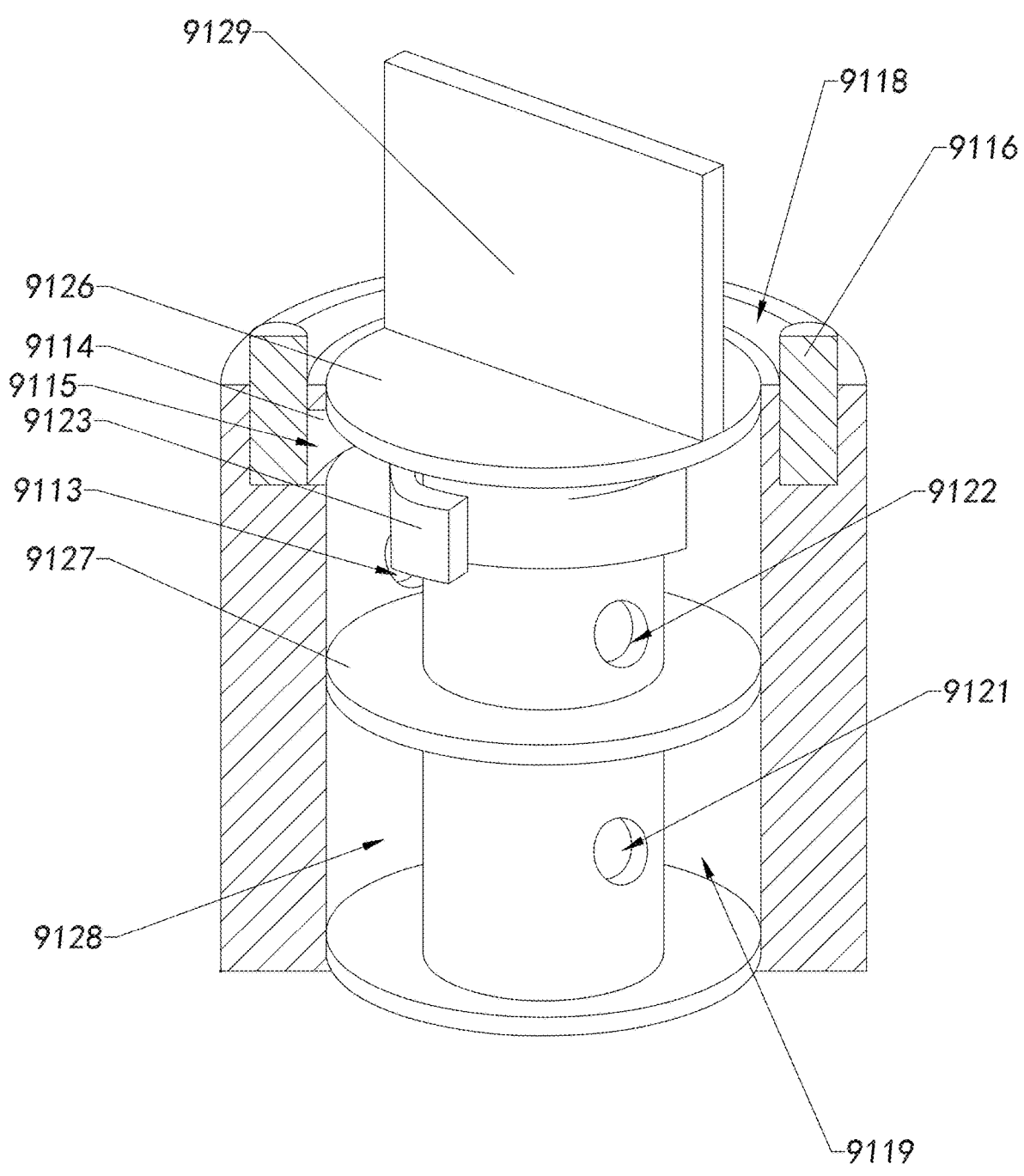
FIG. 3 is a sectional view of the connector of the head brace with the length-adjustable connector according to the above first preferred embodiment of the present invention, illustrating the relationship between a housing and an operation unit of the connector.
Figure 4A:
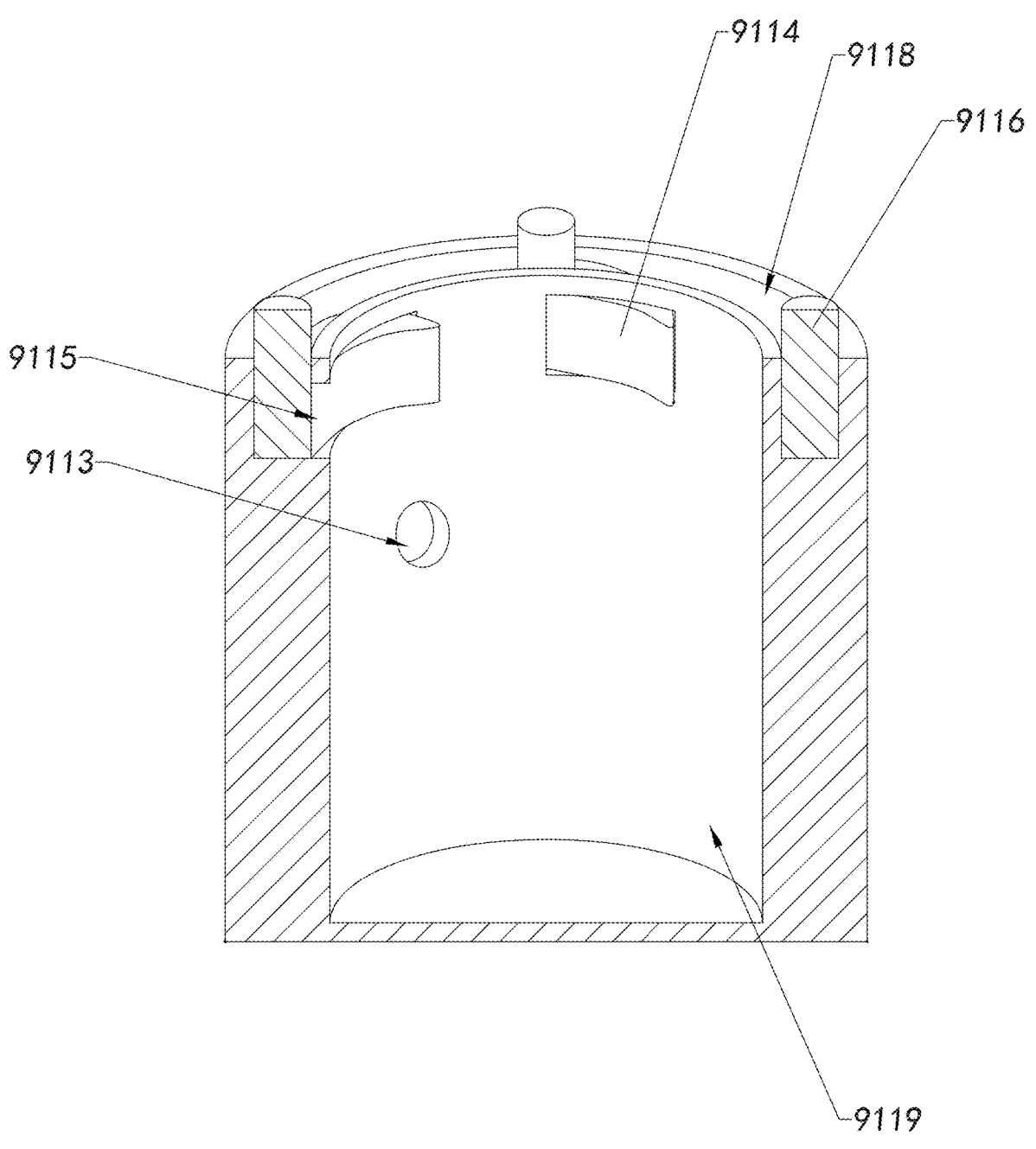
FIG. 4A is a sectional view of the housing of the connector of the head brace with the length-adjustable connector according to the above first preferred embodiment of the present invention, illustrating the fixed state of the connector.
Figure 4B:
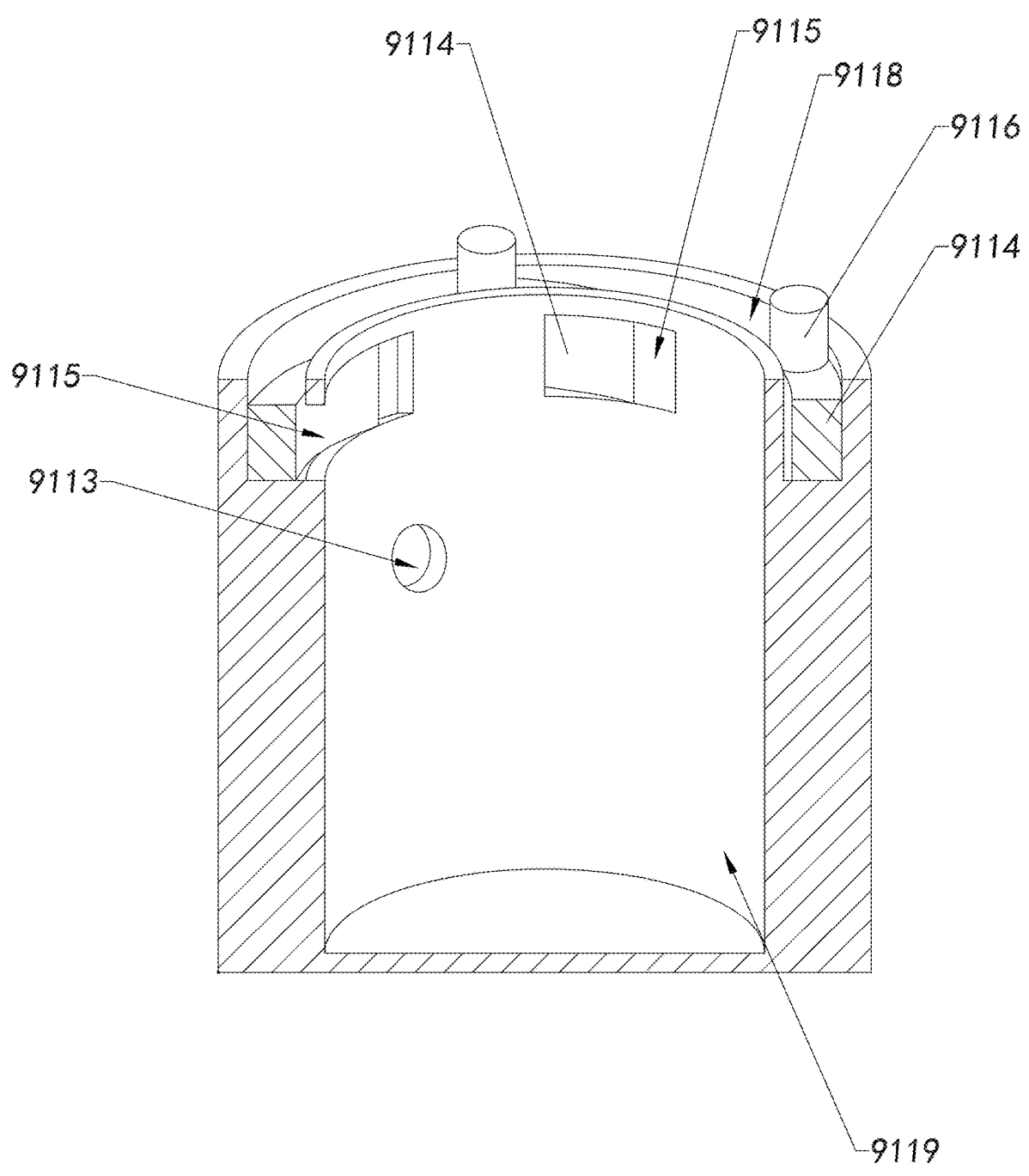
FIG. 4B is a sectional view of the housing of the connector of the head brace with the length-adjustable connector according to the above first preferred embodiment of the present invention, illustrating an adjustable state of the housing.
Figure 5A:
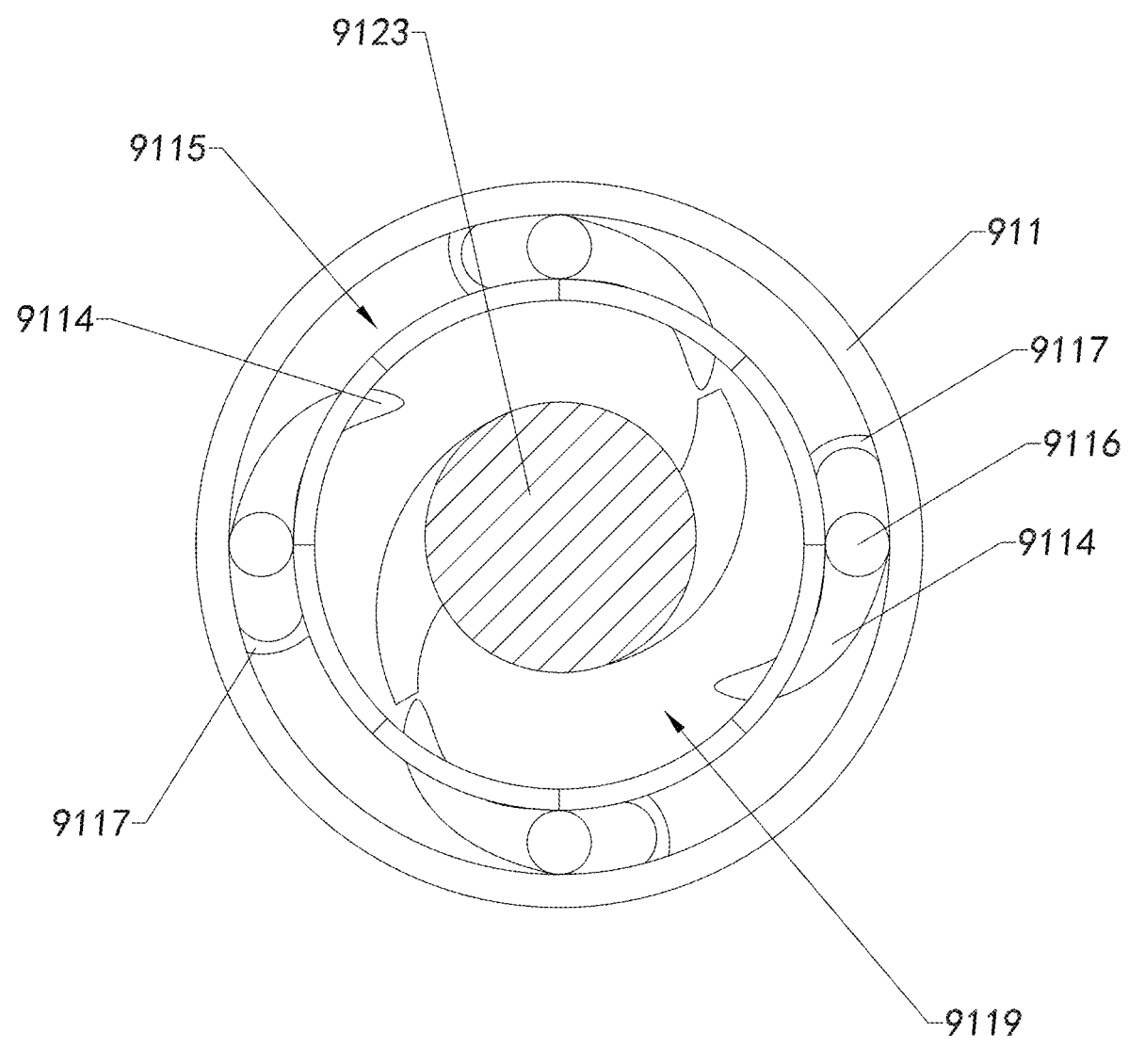
FIG. 5A is a schematic top sectional view of the connector of the head brace with the length-adjustable connector according to the above first preferred embodiment of the present invention, illustrating the fixed state of the connector.
Figure 5B:
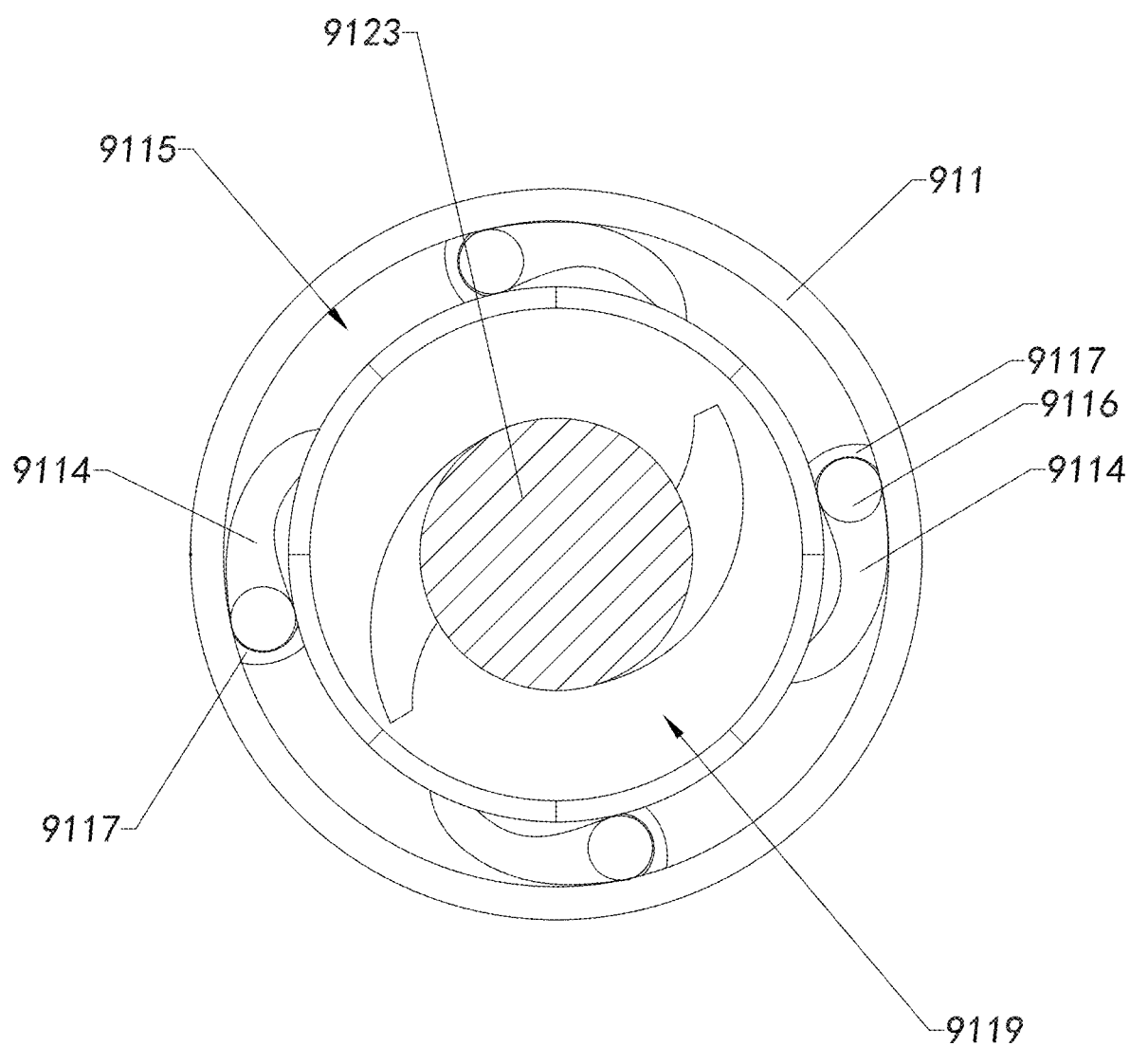
FIG. 5B is a schematic top sectional view of the connector of the head brace with the length-adjustable connector according to the above first preferred embodiment of the present invention, illustrating the adjustable state of the connector.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Those skilled in the art should understand that, in the disclosure of the present invention, terminologies of "longitudinal," "lateral," "upper," "front," "back," "left," "right," "perpendicular," "horizontal," "top," "bottom," "inner," "outer," and etc. that indicate relations of directions or positions are based on the relations of directions or positions shown in the appended drawings, which are only to facilitate descriptions of the present invention and to simplify the descriptions, rather than to indicate or imply that the referred device or element is limited to the specific direction or to be operated or configured in the specific direction. Therefore, the above-mentioned terminologies shall not be interpreted as confine to the present invention.

It can be understood that the term "one" should be understood as "at least one" or "one or more", In other words, in one embodiment, the number of elements can be one, while in another embodiment, the number of elements can be multiple. The term "one" cannot be understood as a limitation on the quantity.

Embodiment 1

As shown in FIGS. 1 to 5, a head brace with a length-adjustable connector according to a preferred embodiment of the present invention is illustrated. The head brace with a length-adjustable connector is suitable for fixing a head of a patient undergoing craniotomy surgery. The head brace with a length-adjustable connector comprises a head brace body 920 and a connector 910. According to this embodiment, the head brace body 920 is used to fix the position of the patient's head. The connector 910 is used to fix the position of small surgical instruments.

The head brace body 920 comprises a base 921 and a plurality of head nails 922. The base 921 provides an installation platform. The head nails 922 are set on the base 921. The head nail 922 is suitable for insertion into the patient's skull. According to this embodiment, the number of the head nails 922 is three. The quantity at one end is one. The quantity at the other end is two. When the patient lies horizontally on the operating table, two of the head nails 922 on one side are first firmly placed on the patient's head. Then pressure is applied with the head nail 922 on the opposite side to achieve the final fixation.

The head brace body 920 comprises a plurality of connection member 926, which comprise a first upright 9261 and a second upright 9262. The first upright 9261 and the second upright 9262 are respectively arranged on two sides of the base 921. In detail, the first upright 9261 is connected to the connector 910. The second upright 9262 is connected to other operating components.

In detail, the head brace body 920 further comprises a pair of retraction members 929. The connection member 926 further comprises a pair of extension members 9263. The extension members 9263 are connected to the second upright 9262. The retraction members 929 are connected to the extension members 9263. In other words, the retraction members 929 are connected to the second upright 9262 through the extension member 9263. The first upright 9261 and the second upright 9262 widen the longitudinal range of the base 921. The extension members 9263 widen the lateral range of the upper space of the base 921. The extension members 9263 are flexibly installed on the second upright 9262. The retraction members 929 are adapted to retract the patient's skull. In other words, the operator is suitable for controlling the movement of the retraction members 929 through the extension members 9263.

The connector 910 comprises a housing 911, an operation unit 912, and a fixation rope 913. The operation unit 912 is adapted to be installed inside the housing 911. The fixation rope 913 is adapted to be clamped between the housing 911 and the operation unit 912. In other words, the fixation rope 913 is set between the housing 911 and the operation unit 912, wherein the fixation rope 913 is adjustable in length. In other words, the operator can adjust the fixation rope 913 between the housing 911 and the operation unit 912 by controlling the operation unit 912.

The housing 911 has a working chamber 9119, which is suitable for placing the operation unit 912. In other words, the operation unit 912 is suitable for performing clamping operations inside the working chamber 9119. In other words, the working chamber 9119 provides a workspace for the operation unit 912 for the operator to control operations through the operation unit 912.

For ease of explanation, the direction of the connection gap between the housing 911 and the operation unit 912 is defined as front. The direction of the housing 911 from the outer diameter towards the center of the cross-section is defined as inner.

The housing 911 has an inner wall and an outer wall, wherein the inner wall is located inside the outer wall. The working chamber 9119 is located inside the inner wall. In other words, the inner wall surrounds and forms the working chamber 9119.

It is worth mentioning that the housing 911 comprises a first ratchet unit 9114 and has a hidden groove 9118, wherein the first ratchet unit 9114 is adapted to be located within the hidden groove 9118. The first ratchet unit 9114 is adapted to be located within the working chamber 9119. In detail, the connector 910 has two states: a fixed state and an adjustable state. Compared with the two states of traditional connectors, traditional connectors can be stably fixed, but adjusting the state is an irreversible operation process, In other words, the fixation rope 913 can only be adjusted to a smaller size. The fixation rope 913 that has been reduced in coil size cannot be rotated to increase it. In other words, the fixed state of the connector 910 can either stably fix the coil size of the fixation rope 913, or rotate the reduced coil size of the fixation rope 913 to increase it.

The first ratchet unit 9114 is adapted to engage the operation unit 912. In detail, when the connector 910 is in a fixed state, the first ratchet unit 9114 is located in the working chamber 9119, and at this time, the operation unit 912 is engaged to the first ratchet unit 9114. The operation unit 912 can irreversibly rotate along the plane where the first ratchet unit 9114 is located to one side. In other words, the motion of the operation unit 912 at this time is irreversible and unidirectional.

When the connector 910 is in the adjustable state, the first ratchet unit 9114 is located in the hidden groove 9118, and at the same time, the operation unit 912 is still located in the working chamber 9119. The operation unit 912 is not engaged by the first ratchet unit 9114, so that the operation unit 912 can rotate clockwise and counterclockwise in the working chamber 9119 without being constrained by the first ratchet unit 9114. In other words, the motion of the operation unit 912 at this time is reversible and in two directions.

In detail, the housing 911 further has a reservation groove 9115, which is set as a channel slot connecting the working chamber 9119 and the hidden groove 9118. In other words, the first ratchet unit 9114 achieves the state transition of the connector 910 through the reservation groove 9115. In other words, the reservation groove 9115 is located on the inner wall of the housing 911. The width of the reservation groove 9115 is greater than the single ratchet width of the first ratchet unit 9114. In other words, the reservation groove 9115 is suitable for accommodating the passage of the first ratchet unit 9114. In other words, the reservation groove 9115 allows the first ratchet unit 9114 to pass through to switch the state of the connector 910.

According to this embodiment, due to the inherent characteristics of the first ratchet unit 9114, it has a plurality of ratchets. Correspondingly, the number of reservation grooves 9115 is also multiple. The number of ratchets of the first ratchet unit 9114 is equal to the number of reservation grooves 9115.

The housing 911 further comprises a limitation member 9117, which is set inside the hidden groove 9118. In other words, the limitation member 9117 is located between the inner wall and the outer wall. The limitation member 9117 is adapted to limit the position of the first ratchet unit 9114, to maintain that the first ratchet unit 9114 is always located in the working chamber 9119 or always in the hidden groove 9118 without being touched by the operator. In other words, the limitation member 9117 plays a role in fixing the position of the connector 910 after the state switch.

The housing 911 further comprises a plurality of extension rod 9116, which is connected to the first ratchet unit 9114. Each extension rod 9116 corresponds to a single ratchet of the first ratchet unit 9114. In detail, the front end of the extension rod 9116 protrudes from the hidden groove 9118. The rear end is connected to the first ratchet unit 9114. In other words, the side of the extension rod 9116 protruding outside the housing 911 is the control end of the first ratchet unit 9114. In other words, the operator can rotate and offset the first ratchet unit 9114 by controlling one end of the extension rod 9116, thereby changing the state of the connector 910.

The extension rod 9116 is adapted to be engaged with the limitation member 9117. The two states of the extension rod 9116 engaged with the limitation member 9117 respectively correspond to the two states of the connector 910. In other words, the connector 910 can always maintain a stable state through the engagement of the limitation member 9117 and the extension rod 9116 in both fixed and adjustable states. In other words, the engagement of the limitation member 9117 and the extension rod 9116 restricts the position of the first ratchet unit 9114 protruding from the working chamber 9119, thereby limiting the range of the limitation member 9117 and preventing the phenomenon that the operation unit 912 is located in the working chamber 9119 but cannot be controlled by the operator due to the excessive protrusion of the first ratchet unit 9114 from the working chamber 9119, In other words, the operator cannot control the length of the fixation rope 913.

Due to the structural characteristics of the first ratchet unit 9114 itself, the front end of each ratchet of the first ratchet unit 9114 is elongated and curved in a crescent shape. The operation unit 912 comprises a second ratchet unit 9123, which corresponds to the first ratchet unit 9114. The second ratchet unit 9123 is adapted to be engaged by the first ratchet unit 9114. In detail, the first ratchet unit 9114 only allows the second ratchet unit 9123 to rotate in one direction. In other words, the first ratchet unit 9114 restricts the unidirectional and irreversible movement of the second ratchet unit 9123. The structure of the second ratchet unit 9123 is different from that of the first ratchet unit 9114. The number of the second ratchet unit 9123 is one. The second ratchet unit 9123 is a single ratchet structure. In other words, the second ratchet unit 9123 is made in one piece and can only be controlled by the operator to rotate and move the second ratchet unit 9123 in its plane.

The operation unit 912 comprises a first partition plate 9126 and a toggle plate 9129. The first partition plate 9126 divides the toggle plate 9129 and the second ratchet unit 9123 into two parts. In other words, the first partition plate 9126 separates the second ratchet unit 9123 from the toggle plate 9129. The toggle plate 9129 is located at the front of the second ratchet unit 9123. The toggle plate 9129 is suitable for being manipulated by an operator and is manufactured as a single unit. In other words, the operator rotates the toggle plate 9129 to achieve the purpose of rotating the operation unit 912. In other words, the toggle plate 9129 drives the overall rotation of the operation unit 912. The toggle plate 9129 is located outside the working chamber 9119. The first partition plate 9126 serves as the opening of the working chamber 9119. In other words, the working chamber 9119 is semi closed with the first partition plate 9126 as the opening.

The operation unit 912 further comprises a second partition plate 9127 and has a wire receiving groove 9128. The second partition plate 9127 divides the second ratchet unit 9123 and the wire receiving groove 9128 into two parts. In other words, the second ratchet unit 9123 and the wire receiving groove 9128 are separated by the second partition plate 9127. The second ratchet unit 9123 is located at the front of the wire receiving groove 9128. When the fixation rope 913 is in the fixed state and adjustable state of the connector 910, two ends are located at the two parts separated by the second partition plate 9127.

For ease of explanation, the wire receiving groove 9128 is located in the first part. The second ratchet unit 9123 is located in the second part.

The wire receiving groove 9128 is suitable for storing the fixation rope 913 therein. In other words, one end of the fixation rope 913 is fixed to the wire receiving groove 9128.

It is worth mentioning that the housing 911 has a first hole 9111, a second hole 9112, and a third hole 9113. The first hole 9111, the second hole 9112. The third hole 9113 respectively pass through the housing 911. In other words, the first hole 9111, the second hole 9112. The third hole 9113 are respectively connected to the inner and outer walls of the housing 911. In other words, the first hole 9111, the second hole 9112. The third hole 9113 are respectively connected to the working chamber 9119 and the outside of the housing 911. The first hole 9111, the second hole 9112. The third hole 9113 are suitable for allowing the fixation rope 913 to pass through. In other words, the fixation rope 913 is suitable for passing through the first hole 9111, the second hole 9112. The third hole 9113 to complete fixation and adjustment.

The first hole 9111 and the second hole 9112 are spaced apart on one side of the housing 911. The second hole 9112 corresponds to the third hole 9113. In other words, the third hole 9113 is located on the other side of the housing 911. The center of the second hole 9112 and the center of the third hole 9113 correspond with each other. In other words, the fixation rope 913 can vertically pass through the third hole 9113 through the second hole 9112.

It is worth mentioning that the fixation rope 913 enters the wire receiving groove 9128 between the operation unit 912 and the housing 911 through the first hole 9111. The fixation rope 913 enters the second part between the operation unit 912 and the housing 911 through the second hole 9112.

It is worth mentioning that the operation unit 912 has a first perforation 9121 and a second perforation 9122. The first perforation 9121 is located inside the wire receiving groove 9128. The second perforation 9122 is located in the second part. The first perforation 9121 runs through the operation unit 912. The second perforation 9122 runs through the second part to connect the two sides. The first perforation 9121 is adapted to correspond to the first hole 9111. The second perforation 9122 is adapted to correspond to the second hole 9112 and the third hole 9113. In other words, when the operation unit 912 rotates within the working chamber 9119, at a moment, the first perforation 9121 and the first hole 9111 are located on the same straight line. The second perforation 9122, the second hole 9112. The third hole 9113 are located on the same straight line.

As an example of the operation of the connector 910 in the fixed state, the operator connects the operation unit 912 to the housing 911, and drives the operation unit 912 to rotate in the working chamber 9119 through the toggle plate 9129, so that the first perforation 9121 corresponds to the first hole 9111. One end of the fixation rope 913 enters into the wire receiving groove 9128 along the first hole 121 and continues to pass through the first perforation 9121. The operator rotates the toggle plate 9129, so as to drive the rotation of the operation unit 912, so that the fixation rope 913 passing through the first perforation 9121 is fixed, and a certain length of the fixation rope 913 is pulled into the wire receiving groove 9128.

At this time, the first ratchet unit 9114 is located inside the working chamber 9119. The operation unit 912 located inside the working chamber 9119 is only allowed to rotate in one direction. The first ratchet unit 9114 is restricted by the second ratchet unit 9123. Rotate the operation unit 912 in one direction and wrap the fixation rope 913 in a circular shape around the operation unit 912. At this time, one end of the fixation rope 913 has been completely fixed to the connector 910.

An example, an operation diagram of the connector 910 is illustrated when the connector is in the adjustable state. The operator continues to rotate the operation unit 912 to a position that the second perforation 9122 corresponds to the second hole 9112 and the third hole 9113, passes the other end of the fixation rope 913 that is not fixed through the second hole 9112, continues to penetrate the second perforation 9122, and passes through the third hole 9113. Pulling the toggle plate 9129, the second perforation 9122 and the second hole 9112 are not aligned with the third hole 9113. The fixation rope 913 that has been passed through pulls the remaining part into the second part. At this point, both sections of the fixation rope 913 are fixed by the connector 910. In other words, the fixation rope 913 is used to place small surgical instruments by the size of the coil between the two ends fixed by the connector 910. Adjust the size of the coil by adjusting the toggle plate 9129 according to the size of the surgical equipment being placed. When it is necessary to further shrink the coil, continue to move the toggle plate 9129 to increase the amount of the fixation rope 913 passing through the second perforation 9122, in order to reduce the size of the coil.

It is worth mentioning that when the coil size needs to be enlarged, the operator needs to control the extension rod 9116 to drive the first ratchet unit 9114 to rotate in the direction, and make the extension rod 9116 engage with the limitation member 9117. Finally, the first ratchet unit 9114 is kept in the hidden groove 9118. At this time, the rotation of the operation unit 912 is not limited by the first ratchet unit 9114. The operator can rotate the toggle plate 9129 in the opposite direction to return the fixation rope 913 along the original path, increasing the length of the coil between the two fixed sections, but still ensuring stable fixation at two ends. At this point, the operator can reversibly adjust the connector 910 to achieve the goal of adjusting the coil size, so as to suit to different surgical equipment sizes.

Figure 6:
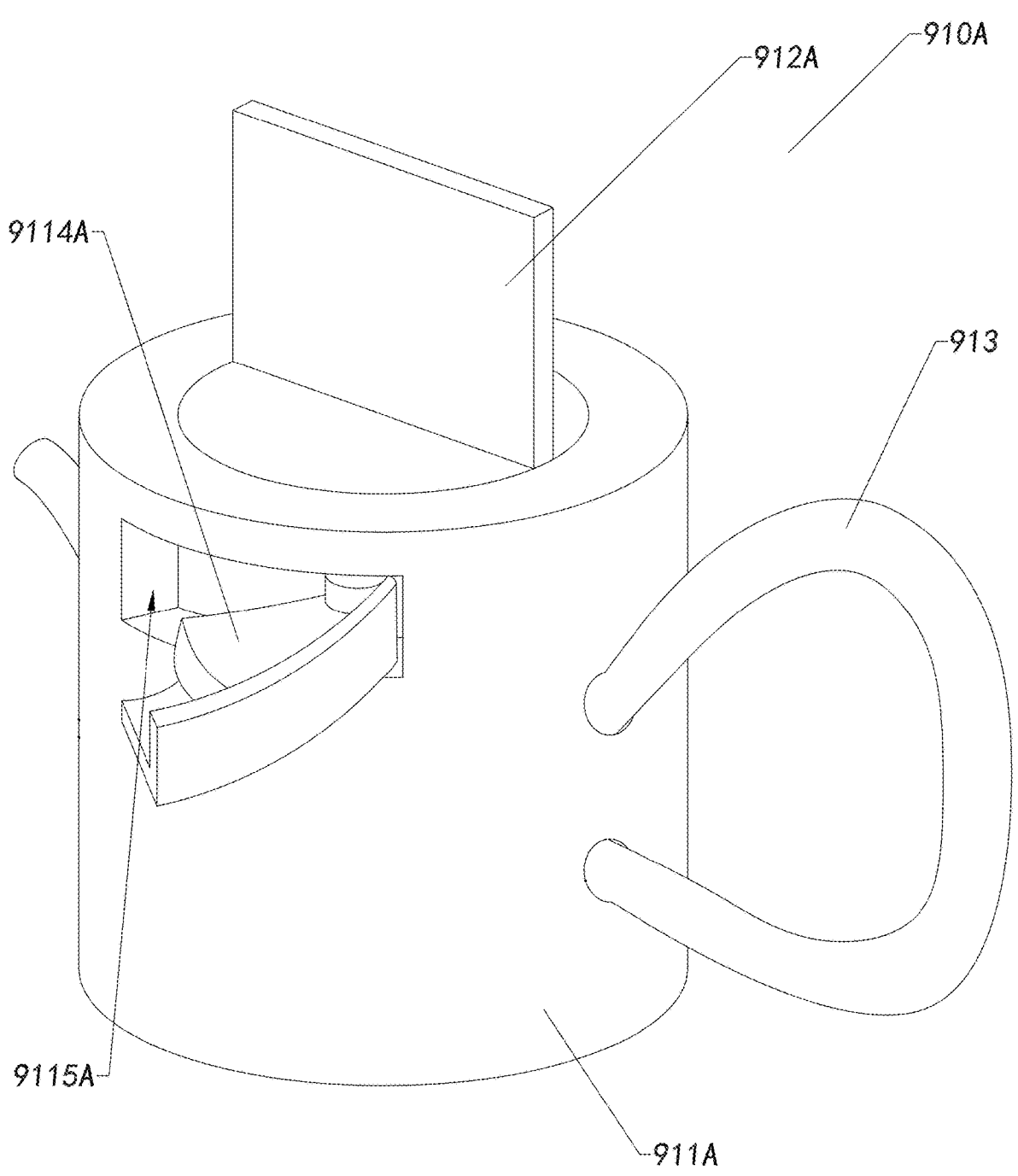
FIG. 6 is a perspective view of a connector of the head brace with the length-adjustable connector according to a second preferred embodiment of the present invention, illustrating the fixed state of the connector.
Figure 7:
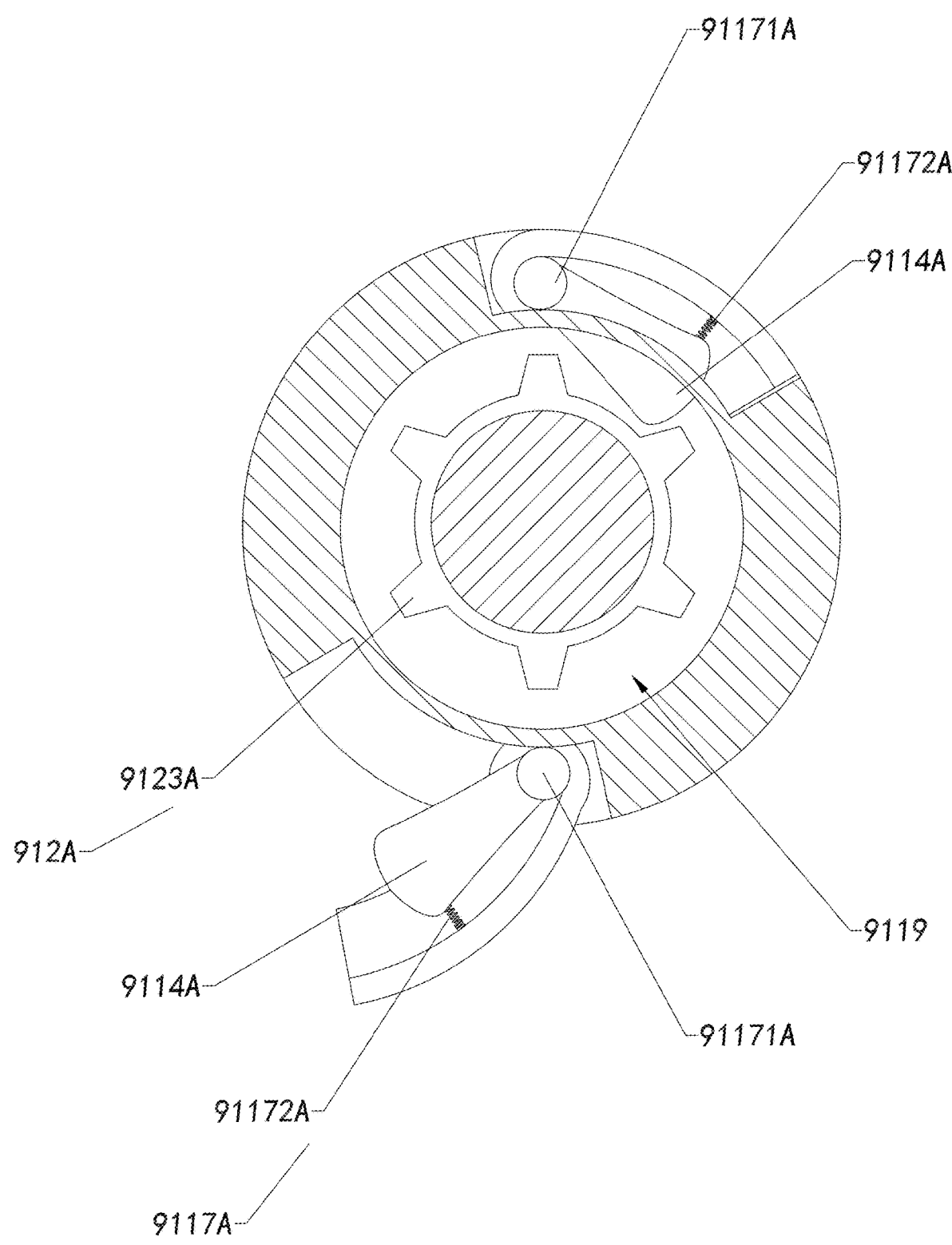
FIG. 7 is a schematic top sectional view of the connector of the head brace with the length-adjustable connector according to the above second preferred embodiment of the present invention, illustrating the fixed state of the connector.
Figure 8:
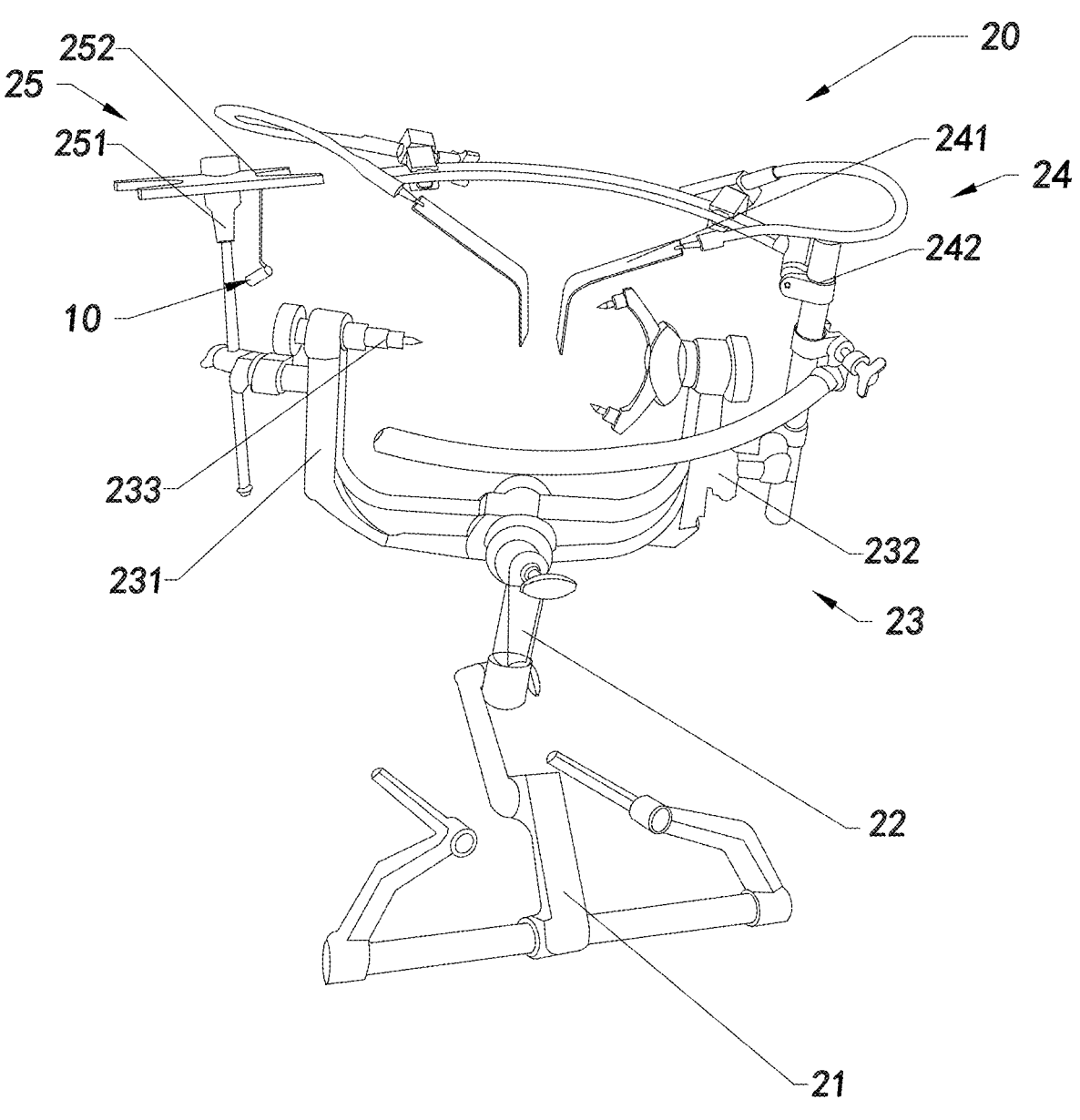
FIG. 8 is a perspective view of a head brace with a length-adjustable connector according to a third preferred embodiment of the present invention.
Figure 9:
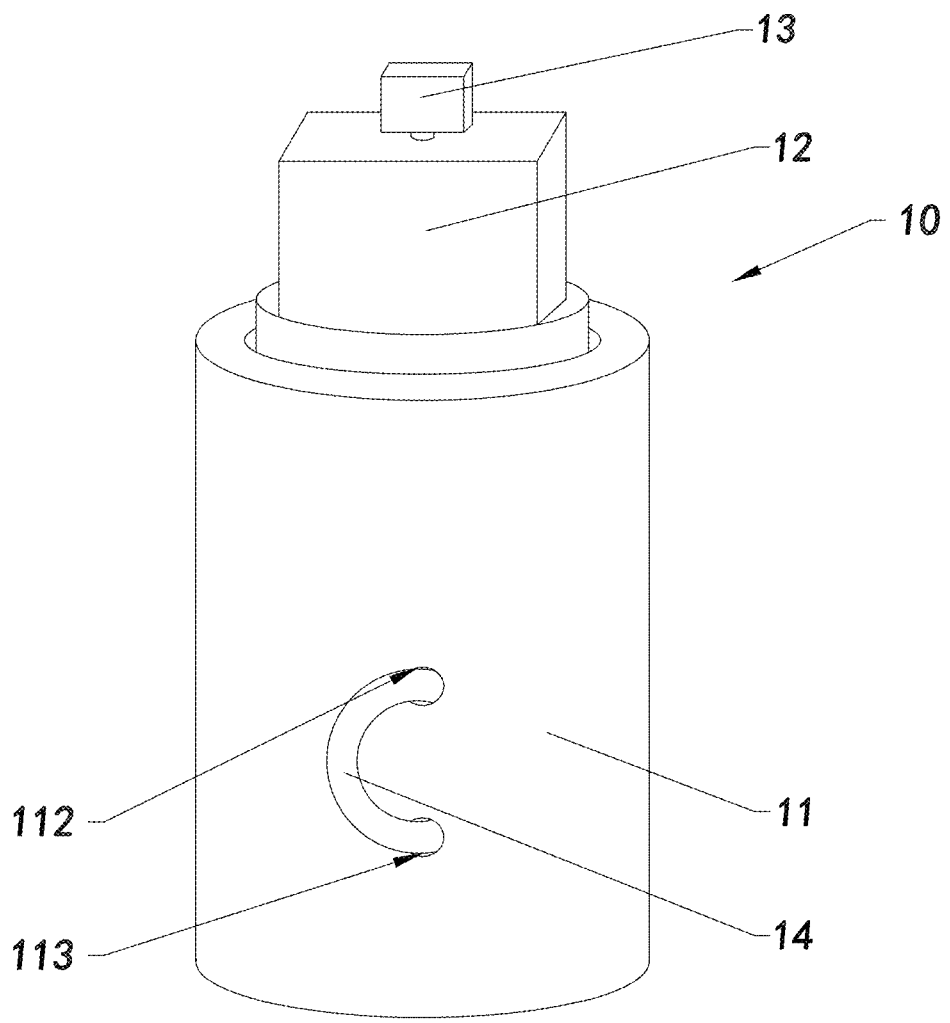
FIG. 9 is a perspective view of the connector of the head brace with the length-adjustable connector according to the above third preferred embodiment of the present invention.
Figure 10:
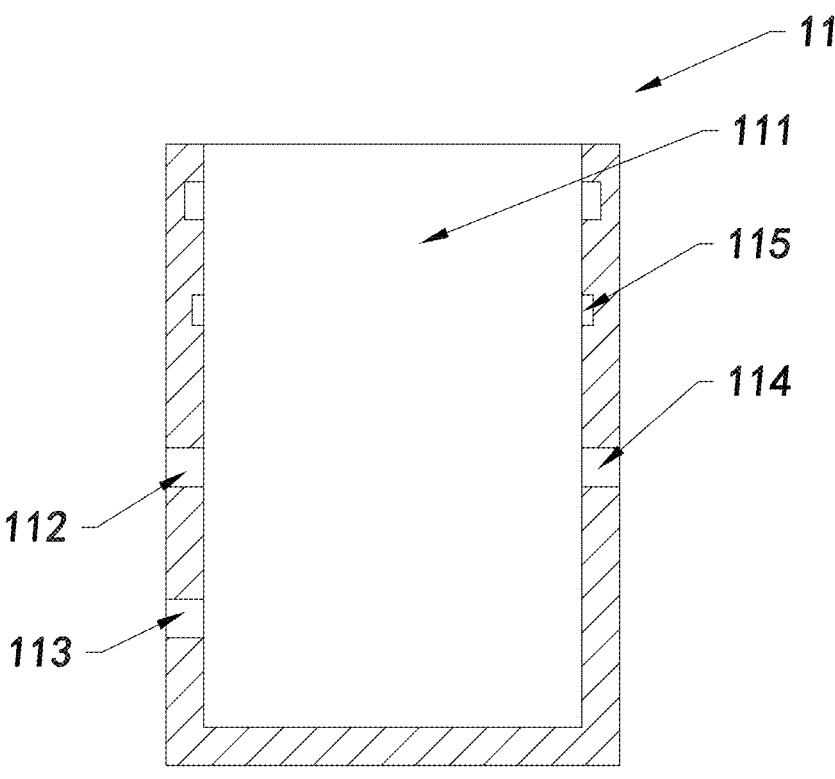
FIG. 10 is a sectional view of an outer main body of the connector of the head brace with the length-adjustable connector according to the above third preferred embodiment of the present invention.
Figure 11:
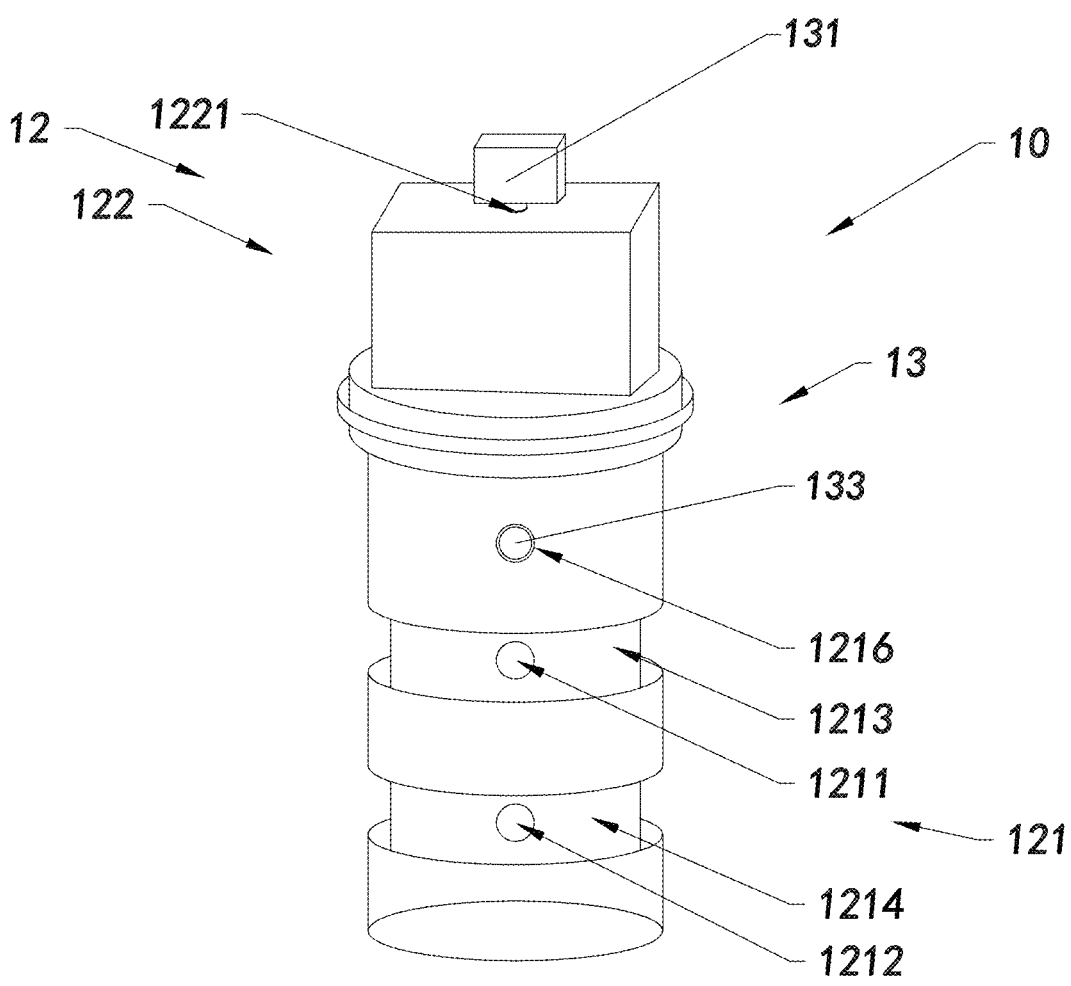
FIG. 11 is a perspective view of an inner core of the connector of the head brace with the length-adjustable connector according to the above third preferred embodiment of the present invention.
Figure 12:
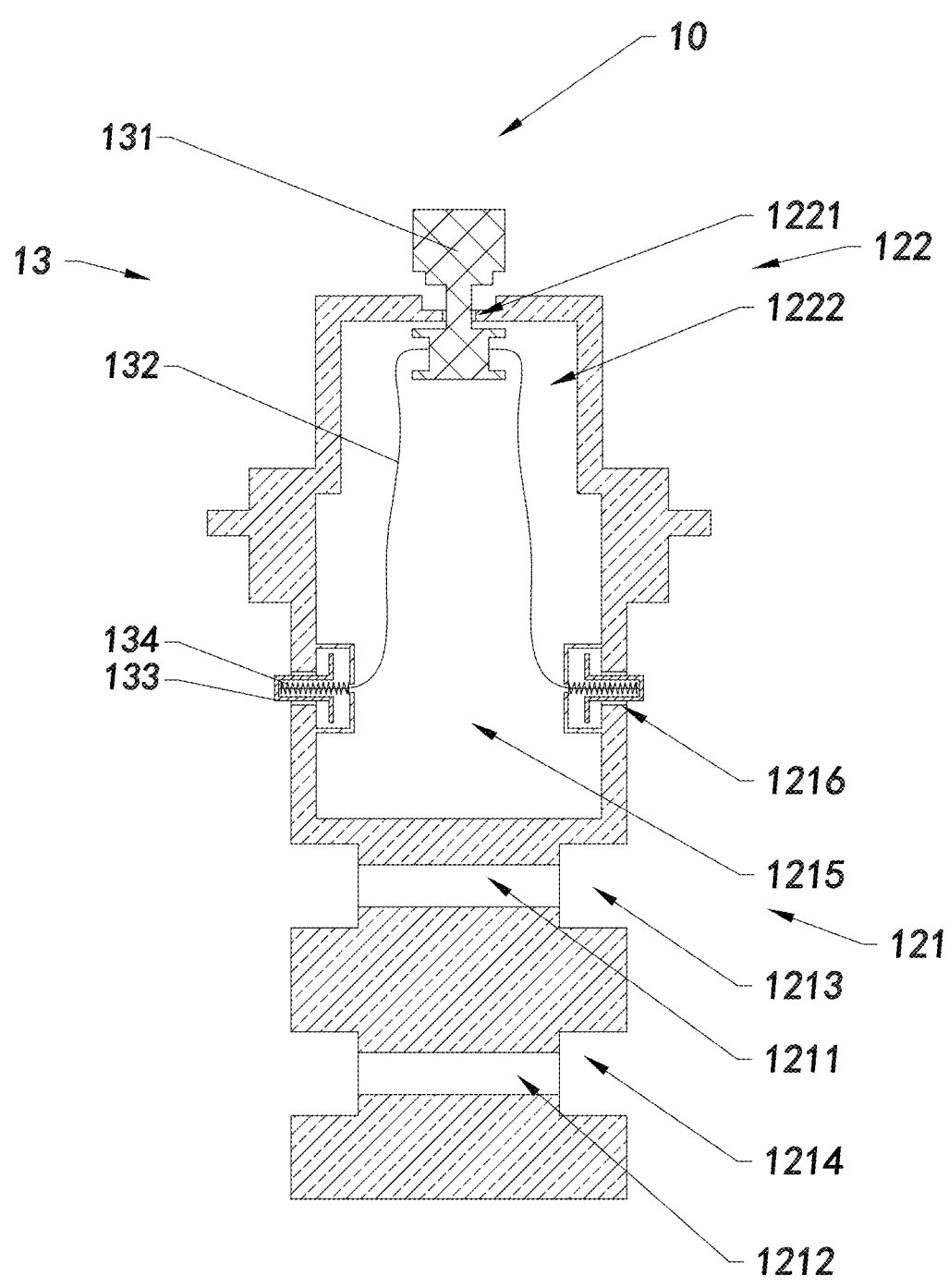
FIG. 12 is a sectional view of the inner core of the connector of the head brace with the length-adjustable connector according to the above third preferred embodiment of the present invention.
Figure 13:
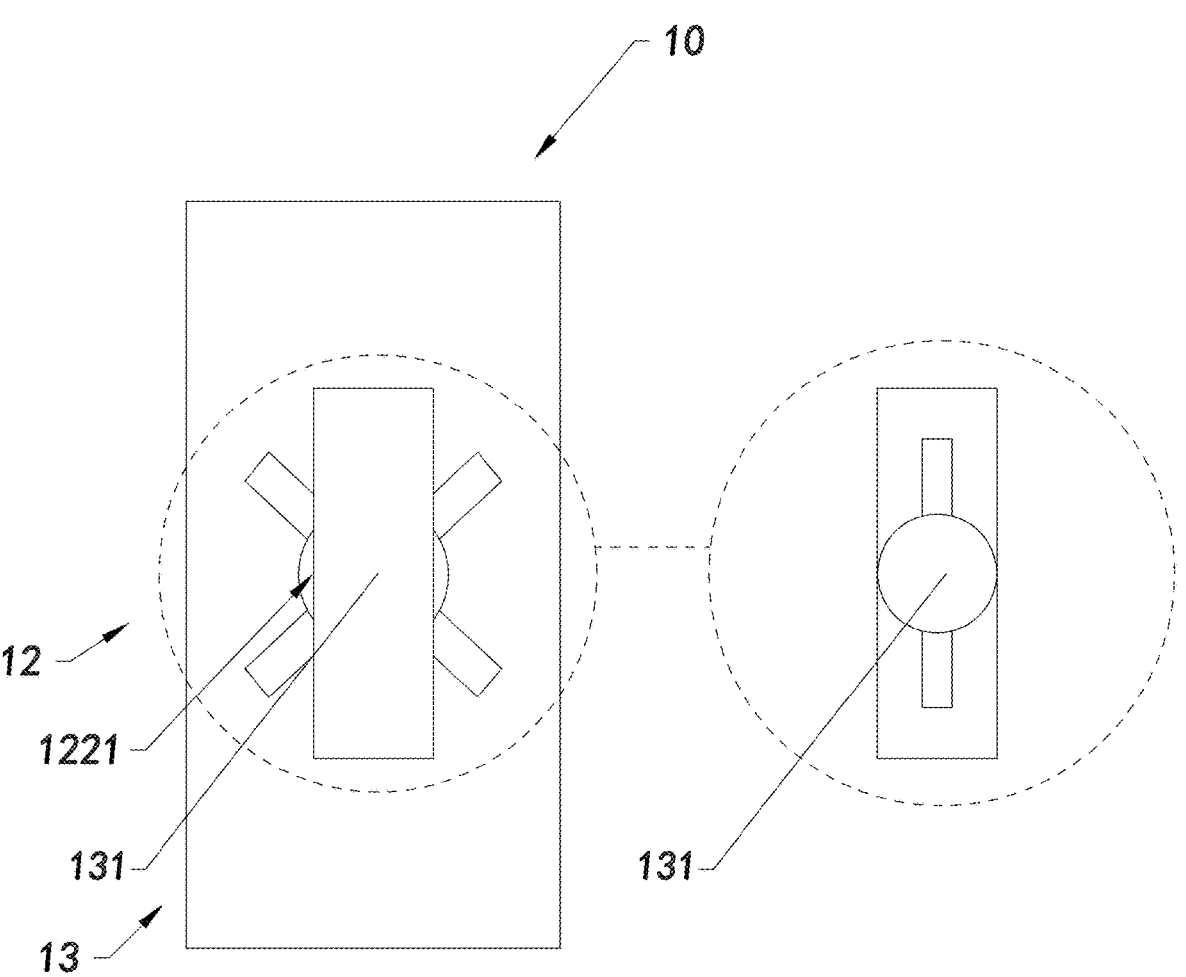
FIG. 13 is a partial enlarged view of the connector of the head brace with the length-adjustable connector according to the above third preferred embodiment of the present invention.
Figure 14:
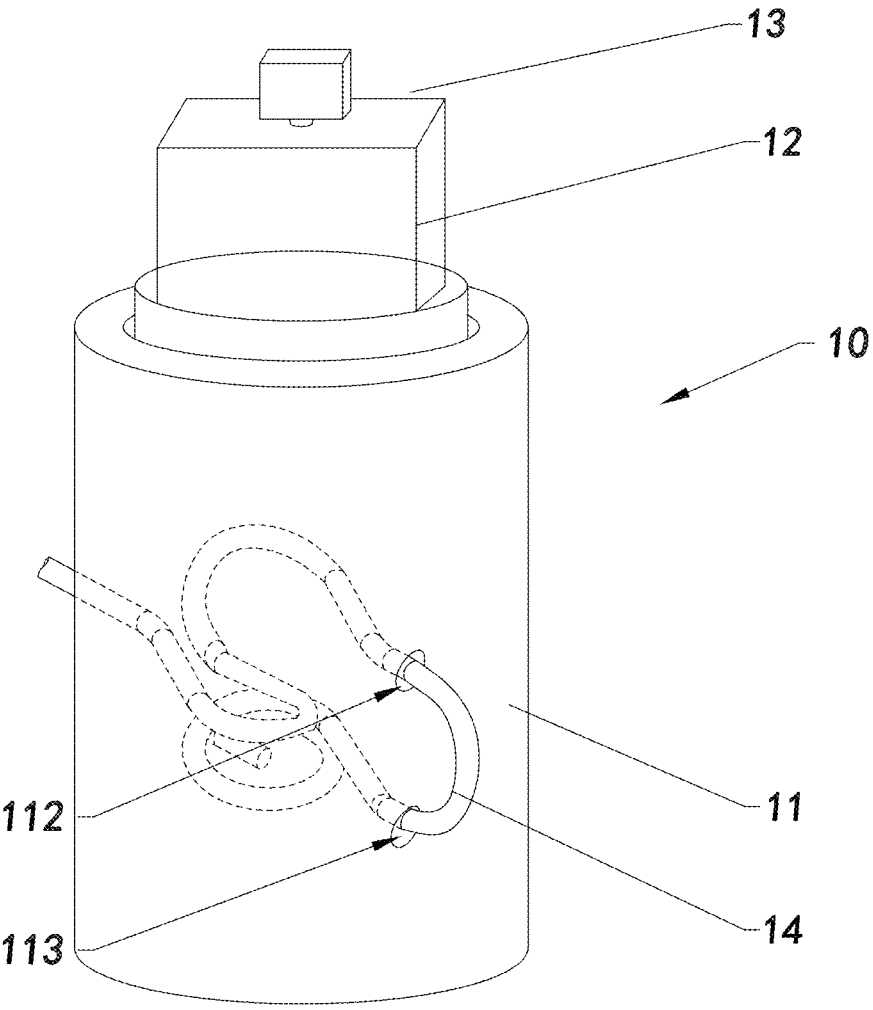
FIG. 14 is a perspective view of the connector of the head brace with the length-adjustable connector according to the above third preferred embodiment of the present invention.

As shown in FIGS. 6 to 7, a head brace with a length-adjustable connector according to a second preferred embodiment of the present invention is illustrated. The main change from the above embodiment is a connector 910A. The connector 910A comprises a housing 911A, an operation unit 912A, and a fixation rope 913. The housing 911A is adapted to cooperate with the operation unit 912A to fix and adjustably set the fixation rope 913 between the housing 911A and the operation unit 912A. Furthermore, the connector 910A adjustably controls the coil length of the fixation rope 913 fixed at two ends between the housing 911A and the operation unit 912A.

What is different from the above first preferred embodiment, the operation unit 912A comprises a second ratchet unit 9123A, wherein the second ratchet unit 9123A has a different shape with the second ratchet unit 9123 according to the above first preferred embodiment. In detail, the shape of the second ratchet unit 9123A is a regular symmetrical shape, with a smooth vertical line between the tooth tip and the tooth bottom, rather than a curved curve with a curvature. In other words, the second ratchet unit 9123A can cooperate with the housing 911A to complete forward and reverse rotation. In other words, the second ratchet unit 9123A reversibly rotates within the working chamber 9119 of the housing 911A.

The housing 911A comprises a pair of first ratchet units 9114A. The number of first ratchet units 9114A is at least two. The first ratchet units 9114A are located on two sides of the housing 911A. In detail, each of the first ratchet units 9114A is located on two sides of the housing 911A to control the unidirectional rotation of the operation unit 912A. The first ratchet unit 9114A is rotatably fixed within the working chamber 9119. When the first ratchet unit 9114A located on one side is located inside the working chamber 9119, the operation unit 912A irreversibly rotates inside the working chamber 9119. When the first ratchet unit 9114A on the other side is located inside the working chamber 9119, the operation unit 14A irreversibly rotates in the opposite direction inside the working chamber 9119. The first ratchet units 9114A respectively control the irreversible rotation of the operation unit 912A in the two directions. In other words, only one of the first ratchet units 9114A is located in the working chamber 9119 at one time.

The first ratchet unit 9114A is located on the outer wall of the housing 911A in a rotatable manner. In detail, the housing 911A has a reservation groove 9115A, so as to connect the working chamber 9119 to the outside. In other words, the reservation groove 9115A allows the first ratchet unit 9114A to pass through. The number of the reservation grooves 9115A is two. In detail, the reservation grooves 9115A are distributed on the two sides of the housing 911A.

The housing 911A further comprises a limitation member 9117A. The limitation member 9117 is suitable for being located in the reservation groove 9115A. The number of limitation members 9117 is two. The limitation member 9117 is adapted to switch the position between the external and the working chamber 9119 through the reservation grooves 9115, thereby controlling the forward and reverse rotation of the operation unit 912A respectively. At one time, only one of the limitation members 9117A is located inside the working chamber 9119. The other limitation member 9117A is located outside the housing 911A. If all the limitation members 9117A are inside the working chamber 9119, the operation unit 912A is limited to one position and cannot move at all.

Furthermore, the limitation member 9117A comprises a rotation member 91171A and an elastic member 91172A, wherein the rotation member 91171A is connected to the elastic member 91172A. The rotation member 91171A is rotatably connected to the outer wall of the housing 911A. In other words, the rotation member 91171A is rotatably connected through the reservation groove 9115A. One end of the elastic member 91172A is connected to the first ratchet unit 9114A. The other end is connected to the rotation member 91171A. In other words, the first ratchet unit 9114A is rotatably connected to the rotation member 91171A through the elastic member 91172A. The rotation of the operation unit 912A within the working chamber 9119 can only be achieved when the first ratchet unit 9114A is movable and located within the working chamber 9119.

When the second ratchet unit 9123A rotates in the working chamber 9119, the first ratchet unit 9114A connected to one side of the limitation member 9117A restricts unidirectional rotation. By using the operation method of fixing the fixation rope 913 in the above first preferred embodiment, the fixation rope 913 is fixed between the housing 911A and the operation unit 912A. The fixing of the fixation rope 913 is achieved by rotating the operation unit 912A in one direction. The change in the size of the coil in the middle of the fixation rope 913 is achieved by rotating a certain angle.

When it is necessary to adjust the coil size of the fixation rope 913, simply drive the first ratchet unit 9114A to disengage from the working chamber 9119 by the limitation members 9117A on two sides. The second ratchet unit 9123A can rotate unobstructed. At this point, the operator can reversibly adjust the coil size of the fixation rope 913.

As shown in FIGS. 8 to 14, a head brace with a length-adjustable connector according to a third preferred embodiment of the present invention is illustrated. The structure of the head brace with the length-adjustable connector comprises a connector 10 and a head brace 20. The connector 10 is suitable for being installed on the head brace 20 to fix small surgical instruments and assist the operator in completing intracranial surgery together with the head brace 20.

The head brace 20 is suitable for fixing the patient's head during intracranial surgery to expose a better surgical field of view and facilitate the operator to perform intracranial surgery more accurately. The connector 10 is suitable for fixing small surgical instruments to facilitate the operator's better access to surgical instruments during surgery, enabling the operator to complete intracranial surgery faster and shorten the surgery time.

The head brace 20 comprises a pedestal 21, a rotation shaft 22, and a head clamp 23. The head brace 20 is adapted to be fixed to a surgical worktable through the pedestal 21. One end of the rotation shaft 22 is connected to the pedestal 21. The other end is connected to the head clamp 23. The head clamp 23 is suitable for fixing the patient's head during surgery to select a better operating position. At the same time, the rotation shaft 22 is rotatably connected to the head clamp 23, so that the direction and position of the head clamp 23 can be adjusted through the rotation shaft 22. The rotation shaft 22 enables the head clamp 23 to better fix the patient's head.

In addition, the head brace 20 further comprises a retraction system 24 and a guidance adapter 25, both of which are installed on the head brace 20. The retraction system 24 is suitable for the operator to retract the patient's body tissue during intracranial surgery to better expose the surgical field and provide a larger operating space for the operator. The guidance adapter 25 is installed on the head clamp 23, suitable for installing the connector 10. In other words, the connector 10 is suitable for being installed on the head brace 20 through the guidance adapter 25.

The head clamp 23 comprises a left clamp arm 231, a right clamp arm 232, and a head nail 233, both of which are in a "C" shape. One end of the left clamp arm 231 and one end of the right clamp arm 232 are adjustably connected to the rotation shaft 22. The other end of the left clamp arm 231 and the other end of the right clamp arm 232 are respectively connected to the head nail 233. One end of the left clamping arm 231 and one end of the right clamping arm 232 are adjustably connected to the rotation shaft 22, so that the head clamp 23 can not only adjust and fix the position and direction of the patient's head, but also adjust the left clamping arm 231 and the right clamping arm 232 according to the patient's head shape and size, thereby controlling the tightness of the head clamp 23 to better fix the patient's head for the operator to perform surgery.

The retraction system 24 comprises a pair of soft shaft retractors 241 and an extension arm 242. One end of the extension arm 242 connects to the head clamp 23 and the other end of the extension arm 242 is used for installing the soft shaft retractors 241. The pair of soft shaft retractors 241 are respectively set at two ends of the extension arm 242 during use, so that the pair of soft shaft retractors 241 are respectively located on two sides of the patient's head, so as to cut open the patient's scalp and craniotomy. Then retracting the patient's scalp tissue from two sides of the patient's head during surgery, providing a good field of view and surgical operation space for the operator.

The guidance adapter 25 comprises a supportation rod 251 and an adapter 252. One end of the supportation rod 251 is fixed to the head clamp 23. The other end is connected to the adapter 252. In other words, the adapter 252 is adapted to be installed on the head clamp 23 through the supportation rod 251. And the guidance adapter 25 is suitable for installing the connector 10. In other words, the connector 10 is suitable for being installed on the head brace 20 through the adapter 252 of the guidance adapter 25.

The connector 10 comprises an outer cover body 11, an inner core body 12, a reversible structure 13, and a fixation rope body 14. The outer cover body 11 is adapted to be sleeved on one end of the inner core body 12, the reversible structure 13 is adapted to be installed on the inner core body 12. The fixation rope body 14 is installed on the outer cover body 11 and connected to the inner core body 12. It is adapted to shrink the fixation rope body 14 by rotating and cooperating with the outer cover body 11 and the inner core body 12, thereby fixing small medical devices to the connector 10.

The relative rotation between the inner core body 12 and the outer cover body 11 of the existing connector is irreversible. In other words, the rotation of the outer cover body 11 and the inner core body 12 of the existing connector is unidirectional and can only be contracted and fixed. After being fixed, they cannot be released, so there are many drawbacks. The connector 10 of the head brace with a length-adjustable connector has a reversible structure 13, so the rotation of the outer cover body 11 and the inner core body 12 is reversible during use. After being fixed, they can be released, reducing many drawbacks. During surgery, instrument use is more convenient. The cost of using the connector 10 is also reduced.

The outer cover body 11 is preferably cylindrical in shape. The shape of the outer cover body 11 is not limited in the present invention. The outer cover body 11 has an opening on the top. The opening extends into the interior of the outer cover body 11 to form an inner core accommodation cavity 111, which is suitable for accommodating the inner core body 12.

The outer wall of the outer cover body 11 has a first fixation hole 112, a second fixation hole 113, and a third fixation hole 114. The first fixation hole 112 and the second fixation hole 113 are located on the same side of the outer wall of the outer cover body 11. The third fixation hole 114 is located on the other side of the outer wall of the outer cover body 11. In other words, the third fixation hole 114 is in a relative position with the first fixation hole 112 and the second fixation hole 113 on the same outer wall. And the third fixation hole 114 is located on the same horizontal axis as the first fixation hole 112. The first fixation hole 112 and the third fixation hole 114 are symmetrically distributed with a mirror image of the central axis of the outer cover body 11.

The first fixation hole 112, the second fixation hole 113. The third fixation hole 114 are spaced apart on the outer wall of the outer cover body 11, and extend from the outer wall surface into the inner core accommodation cavity 111, penetrating through the outer wall.

The inner wall of the outer cover body 11 has an installation groove located near the opening of the inner core accommodation cavity 111. The installation groove is suitable for holding the inner core body 12 inside the inner core accommodation cavity 111.

The inner wall of the outer cover body 11 further has a plurality of clamping groove 115, which is suitable for limiting and fixing the inner core body 12 when it rotates relative to the outer cover body 11. The clamping grooves 115 are suitable for holding the inner core body 12 in a certain rotational position through a snap connection when the inner core body 12 rotates, achieving fixation after rotation. The inner core body 12 cooperates with the outer cover body 11. The fixation rope body 14 contracts by rotating and fixing, thereby fixing the small medical device.

The outer wall of the outer cover body 11 further has an anti-slip surface protruding from the outer wall of the outer cover body 11, which is suitable for users to grip and prevent the connector 10 from slipping during use, making it impossible to rotate the core body 12 and achieve fixation.

The inner core body 12 comprises a fixation member 121 and a grip member 122. One end of the fixation member 121 is integrally connected to the grip member 122. The other end is accommodated and held in the inner core accommodation cavity 111 of the outer cover body 11.

The fixation member 121 is preferably formed by splicing two halves. The side end of the fixation member 121 has a second fixation groove 1214 near the bottom of the fixation member 121. The second fixation groove 1214 extends vertically from the side end surface of the fixation member 121 to the inside of the fixation member 121, so that the second fixation groove 1214 is recessed on the side end surface of the fixation member 121. The second fixation groove 1214 surrounds the side end of the fixation member 121 once. The second fixation groove 1214 is suitable for accommodating the fixation rope body 14 when the inner core body 12 rotates relative to the outer cover body 11.

The fixing component 121 further has a second inner hole 1212, which is located at the bottom of the second fixation groove 1214. The second inner hole 1212 extends vertically from the bottom of the second fixation groove 1214 to the inside of the fixing component 121, passing through the fixing component 121 horizontally. The second inner hole 1212 is suitable for the fixation rope body 14 to pass through.

The side end of the fixation member 121 has a first fixation groove 1213, which is located near the top of the fixation member 121. The first fixation groove 1213 extends vertically from the side end surface of the fixation member 121 to the inside of the fixation member 121, so that the first fixation groove 1213 is recessed on the side end surface of the fixation member 121 and surrounds the side end of the fixation member 121. The first fixation groove 1213 is suitable for accommodating the fixation rope body 14 when the inner core body 12 rotates relative to the outer cover body 11.

The side end of the fixation member 121 further has a first inner hole 1211, which is located at the bottom of the first fixation groove 1213. The first inner hole 1211 extends vertically from the bottom of the first fixation groove 1213 to the inside of the fixation member 121, so as to horizontally penetrate the fixation member 121. The first inner hole 1211 is suitable for the fixation rope body 14 to pass through.

When the inner core body 12 is installed in the inner core accommodation cavity 111 of the outer cover body 11, the first inner hole 1211 is adapted to be on the same horizontal axis as the first fixation hole 112 and the third fixation hole 114. The second inner hole 1212 is adapted to be on the same horizontal axis as the second fixation hole 113, for the fixation rope body 14 to pass through and tighten the fixation rope body 14 through the relative rotation of the inner core body 12 and the outer cover body 11, thereby achieving a fixing effect.

The side end of the fixation member 121 has an installation hole 1216, which is located at the opposite upper end of the first fixation groove 1213. Compared with the first fixation groove 1213, the installation hole 1216 is located closer to the top of the fixation member 121. The installation hole 1216 extends from the side surface of the fixation member 121 and runs horizontally through the fixation member 121.

The interior of the fixation member 121 further has a second traction chamber 1215, which is connected to the first traction chamber 1222. The second traction chamber 1215 is suitable for accommodating the reversible structure 13.

The grip member 122 is preferably formed by splicing two halves together. The grip member 122 is integrally connected to the top of the fixation member 121. Inside the grip member 122, there is a first traction chamber 1222, which is connected to the second traction chamber 1215. The first traction chamber 1222 is suitable for installing the reversible structure 13.

One end of the grip member 122 is connected to the fixation member 121. The other end has a control member installation hole 1221. The control member installation hole 1221 extends vertically from the end plane of the grip member 122 to the interior of the grip member 122, connecting to the first traction chamber 1222. The periphery of the control member installation hole 1221 has a plurality of recessed portions, which are recessed in the end plane of the grip member 122 and are suitable for cooperating with the control member installation hole 1221 for installing the reversible structure 13.

The reversible structure 13 comprises a control member 131, a connection unit 132, a clamping member 133, and an elastic element 134. One end of the connection unit 132 is connected to the control member 131. The other end of the connection unit 132 is connected to the clamping member 133. It is suitable for controlling the movement of the connection unit 132 by rotating the control member 131, thereby driving the movement of the clamping member 133 and achieving the clamping and disengagement of the clamping member 133.

The control member 131 is rotatably mounted on the grip member 122 through the control member installation hole 1221 at the top of the grip member 122. The control member 131 comprises a head and a tail, and is mounted on the grip member 122 through the tail. The tail is also connected to the connection unit 132. When the control member 131 rotates, the connection unit 132 wraps around the head and tail, achieving the contraction of the connection unit 132. The head of the control member 131 has a protruding portion located at one end of the head near the tail. The protruding portion is suitable for being accommodated in the recessed portion of the grip member 122, and is suitable for fixing the control member 131 after rotation by engaging with the recessed portion through the protruding portion.

The clamping member 133 is installed on the fixation member 121 through the installation hole 1216 and the second traction chamber 1215. The clamping member 133 is preferably in a "convex" shape. The top of the "convex" shape of the clamping member 133 protrudes from the side end surface of the fixation member 121 through the installation hole 1216. The clamping member 133 is suitable for being accommodated in the clamping groove 115 of the outer cover body 11 after protruding from the side end surface of the fixation member 121, and is suitable for holding the fixation member 121 in the rotated position after the fixation member 121 rotates.

The diameter of the "convex" bottom of the clamping member 133 is larger than that of the installation hole 1216, so the "convex" bottom of the clamping member 133 is located inside the second traction chamber 1215. The convex bottom of the clamping member 133 has an elastic element receiving cavity, and one end of the elastic element 134 is connected to the control member 131 through the elastic element receiving cavity. The other end is connected to the inner wall of the second traction chamber 1215. The elastic element 134 is suitable for causing the compressed clamping member 133 to rebound when the fixation member 121 rotates.

One end of the connection unit 132 is connected to the control member 131. The other end passes through the first traction chamber 1222 and the second traction chamber 1215 and is connected to the "convex" bottom of the clamping member 133.

The fixation rope body 14 comprises a head end and a tail end. When in use, the head end or tail end of the fixation rope body 14 is inserted into the outer cover body 11 through the second fixation hole 112, and enters the fixation member 121 through the second inner hole 1212. The fixation member 121 is rotated forward to wrap the fixation rope body 14 in the second fixation groove 1214. After winding is completed, the other end of the fixation rope body 14 is inserted into the outer cover body 11 through the first fixation hole 112, and enters the fixation member 121 through the first inner hole 1211. It exits from the first inner hole 1211 and passes through the third fixation hole 112. Thread out and rotate the fixing component 121 in the forward direction, so that the other end of the fixation rope body 14 is wrapped around the first fixation groove 1214. At this time, the fixation rope body 14 and the side wall of the outer cover body 11 will form a retractable circular structure. The medical device will be placed inside the retractable circular structure. The fixation member 121 will be rotated to continuously shrink the fixation rope body 14 to achieve instrument fixation. Because the clamping member 133 is engaged with the clamping groove 115, the fixation member 121 will remain in the rotated position after rotation, so the connector 10 can be fixed after rotation.

When the clamping member 133 is accommodated in the clamping groove 115, the medical device is fixed. When it is necessary to release the fixed medical device, the control member 131 is rotated in the opposite direction to drive the connection unit 132 to move, so that one end of the connection unit 132 is wrapped around the tail. The connection unit 132 contracts, driving the clamping member 133 to move towards the second traction chamber 1215 inside the fixation member 121, so that the clamping member 133 is released from the clamping groove 115, so that the fixation member 121 can rotate freely. When the fixation member is rotated in the opposite direction, the fixation rope body 14 is relaxed, the fixed medical device is released, and in the control member. After rotating, the protruding part of the control member 131 engages with the recessed part of the grip member 122, achieving reverse rotation and fixation.

Figure 15:
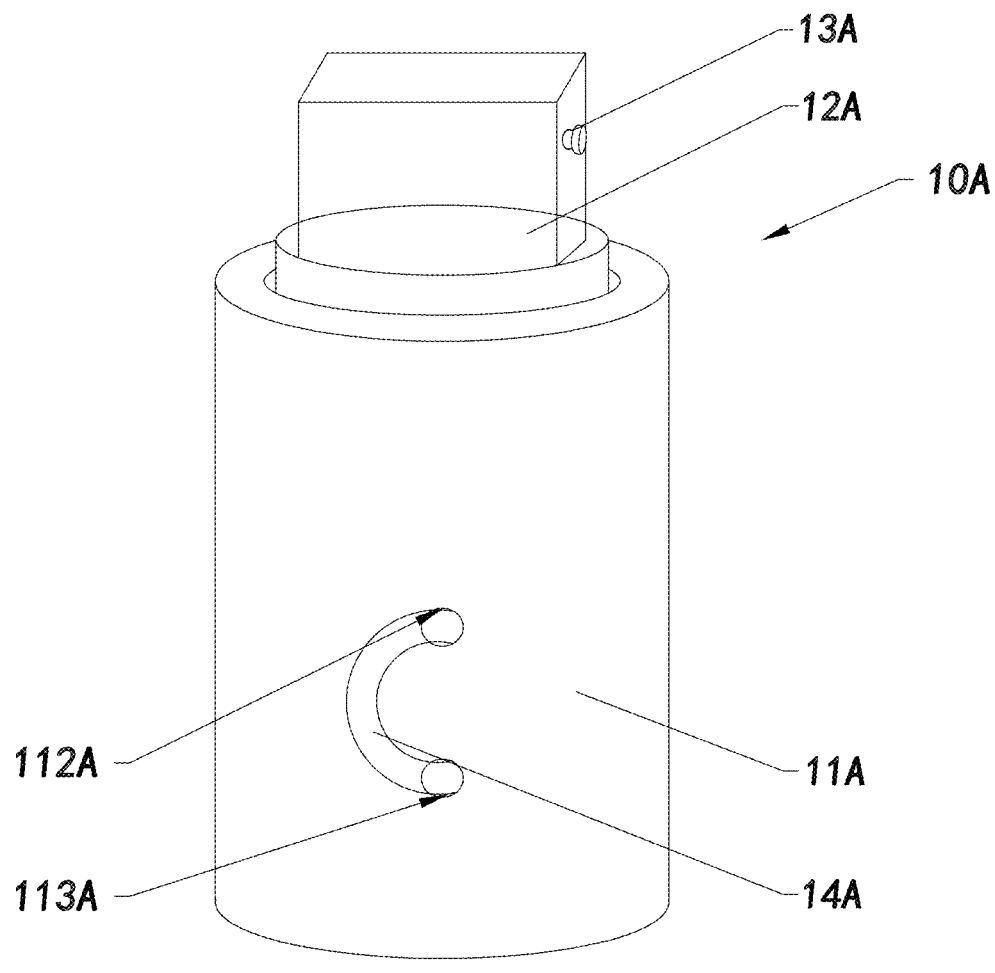
FIG. 15 is a perspective view of the connector of a head brace with a length-adjustable connector according to a fourth preferred embodiment of the present invention.
Figure 16:
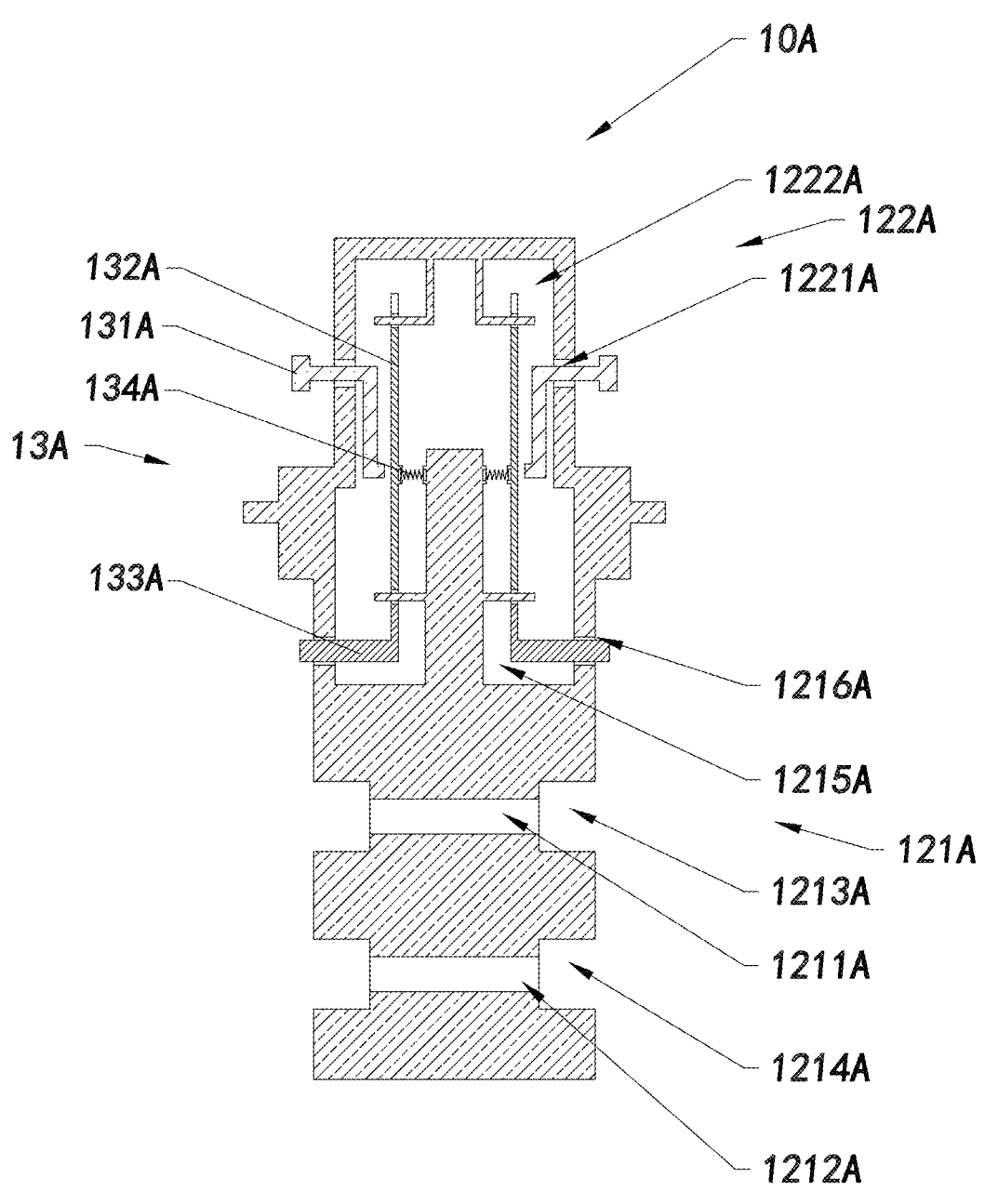
FIG. 16 is a sectional view of an inner core of the connector of the head brace with the length-adjustable connector according to the above fourth preferred embodiment of the present invention.

As shown in FIGS. 15 to 16, a head brace with a length-adjustable connector according to a fourth preferred present invention is illustrated. The structure of the head brace with the length-adjustable connector comprises a connector 10A and a head brace 20A. The connector 10A is suitable for being installed on the head brace 20A for fixing small surgical instruments and assisting the operator in completing intracranial surgery together with the head brace 20A.

The head brace with the length-adjustable connector according to the third preferred embodiment and the head brace with the length-adjustable connector according to the fourth embodiment are structurally similar. The head brace 20A has the same structure. The only difference is that the reversible structure 13A of the connector 10A is different.

The inner core body 12A in the fourth embodiment comprises a fixation member 121A and a grip member 122A. One end of the fixation member 121A is integrally connected to the grip member 122A. The other end is accommodated and held in the inner core accommodating cavity 111A of the outer cover body 11A.

The fixation member 121A is preferably formed by splicing two halves. The side end of the fixation member 121A, near the bottom of the fixation member 121A, has a second fixation groove 1214A. The second fixation groove 1214A extends vertically from the side end surface of the fixation member 121A to the inner part of the fixation member 121A, so that the second fixation groove 1214A is recessed on the side end surface of the fixation member 121A. The second fixation groove 1214A surrounds the side end of the fixation member 121A once. The second fixation groove 1214A is suitable for accommodating the fixation rope body 14A when the inner core body 12A rotates relative to the outer cover body 11A.

The bottom of the second fixation groove 1214A further has a second inner hole 1212A, which extends vertically from the bottom of the second fixation groove 1214A to the inside of the fixation member 121A, so as to pass through the fixation member 121A laterally. The second inner hole 1212A is suitable for the fixation rope body 14A to pass through.

The side end of the fixation member 121A, near the top of the fixation member 121A, has a first fixation groove 1213A. The first fixation groove 1213A extends vertically from the side end surface of the fixation member 121A to the inside of the fixation member 121A, so that the first fixation groove 1213A is recessed into the side end surface of the fixation member 121A. The first fixation groove 1213A surrounds the side end of the fixation member 121A. The second fixation groove 1213A is suitable for accommodating the fixation rope body 14A when the inner core body 12A rotates relative to the outer cover body 11A.

The bottom of the first fixation groove 1213A further has a first inner hole 1211A, which extends vertically from the bottom of the first fixation groove 1213A to the inside of the fixation member 121A, so as to horizontally penetrate the fixation member 121A. The first inner hole 1211A is suitable for the fixation rope body 14A to pass through.

When the inner core body 12A is installed in the inner core accommodation cavity 111A of the outer cover body 11A, the first inner hole 1211A is adapted to be on the same horizontal axis as the first fixation hole 112A and the third fixation hole 114A. The second inner hole 1212A is adapted to be on the same horizontal axis as the second fixation hole 113A, for the fixation rope body 14A to pass through and tighten the fixation rope body 14A through the relative rotation of the inner core body 12A and the outer cover body 11A, thereby achieving a fixing effect.

The side end of the fixation member 121A has an installation hole 1216A, which is located at the opposite upper end of the first fixation groove 1213A. Compared to the first fixation groove 1213A, the installation hole 1216A is located closer to the top of the fixation member 121A. The installation hole 1216A extends from the side surface of the fixation member 121A and runs horizontally through the fixation member 121A.

The interior of the fixation member 121A further has a second traction chamber 1215A, which is connected to the installation hole 1216A. The second traction chamber 1215A is suitable for accommodating the reversible structure 13A.

The grip member 122A is preferably made by splicing two halves together, and is integrally connected to the top of the fixation member 121. Inside the grip member 122A, there is a first traction chamber 1222A, which is connected to the second traction chamber 1215A. The first traction chamber 1222A is suitable for installing the reversible structure 13A.

The two ends of the grip member 122A each have a control member installation hole 1221A, which extends vertically from the plane of the two ends of the grip member 122A towards the interior of the grip member 122A to connect with the first traction chamber 1222A.

The reversible structure 13A comprises a control member 131A, a clamping member 133A, an elastic element 134A, and a connection unit 132A. One end of the connection unit 132A is connected to the clamping member 133A. The other end is connected to the grip member 122A through the internal structure of the second traction chamber 1215A. The middle position of the connection unit 132A is respectively connected to the control member 131A and the elastic element 134A. The connection positions of the control member 131A and the elastic element 134A are located on two sides of the middle of the connection unit 132A, and one end of the elastic element 134A is connected to the middle of the connection unit 132A. One end is connected to the inner wall of the first traction chamber 1222A. When in use, the connection unit 132A is activated by pressing the control member 135A, so as to drive the clamping member 133A to move into the second traction chamber 1215A, achieving the detachment of the clamping member 133A from the clamping groove 115A, further causing the fixing component 121A to lose its fixing function and can rotate freely. After the rotation is completed, release the control member 131A. The elastic element 134A drives the connection unit 132A to rebound, driving the clamping member 133A to move outward through the installation hole 1216, so that the clamping member 133A can be locked with the clamping groove 115A and restore its fixing function.

As shown in FIGS. 17 to 34, fixation connectors according to other preferred embodiments of the present invention are illustrated. The fixation connector 101 is installed on a head brace, which is needed to fix the patient's head during head surgery for ease of surgical operation. The length of the fixation connector 101 can be adjusted and the adjusted length is very convenient for fixing, making it easy to fix small surgical instruments during surgery.

Figure 17:
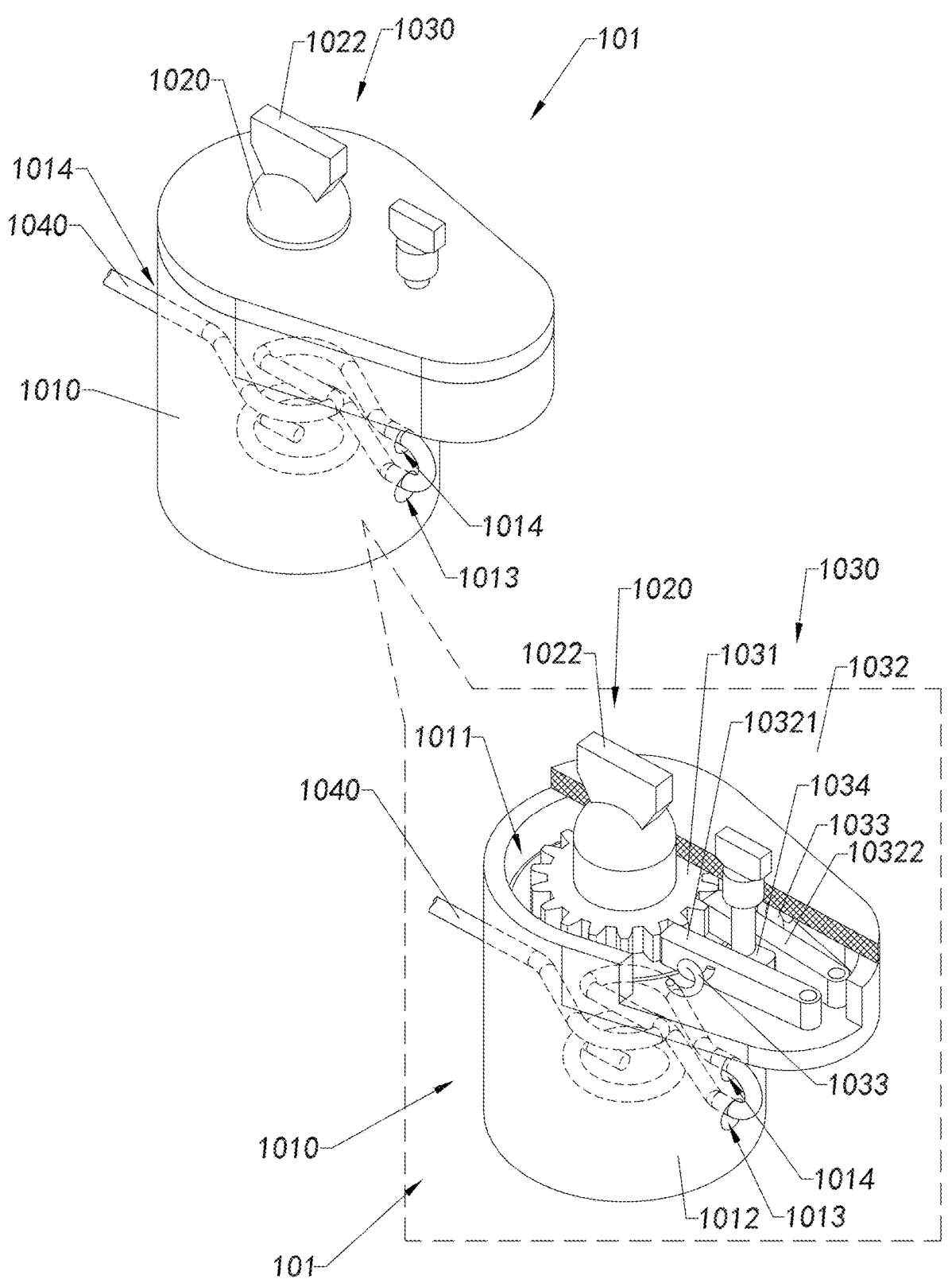
FIG. 17 is a perspective view of a fixation connector according to a fifth preferred embodiment of the present invention.
Figure 18:
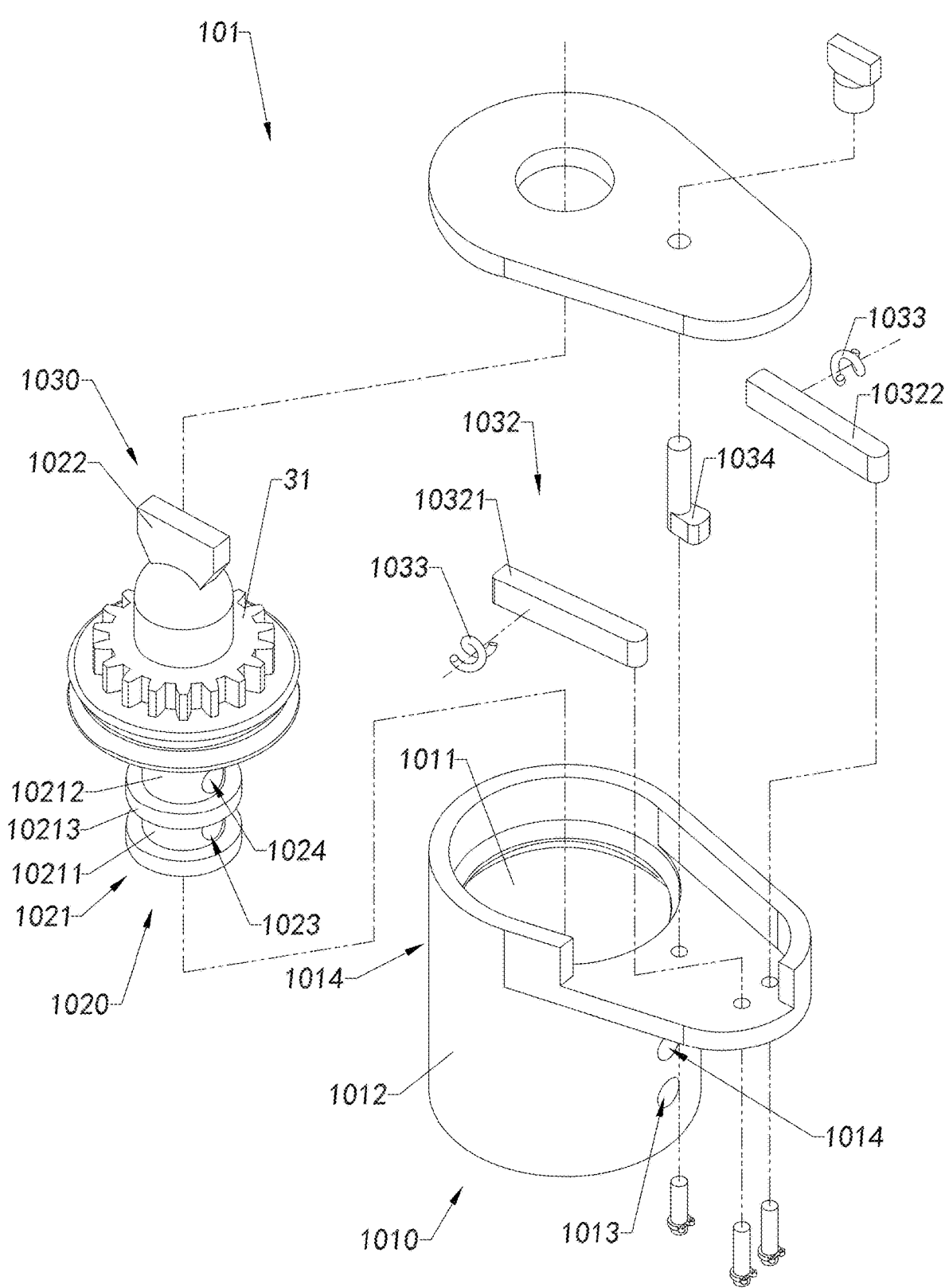
FIG. 18 illustrates a control unit of the fixation connector according to the above fifth preferred embodiment of the present invention.
Figure 19:
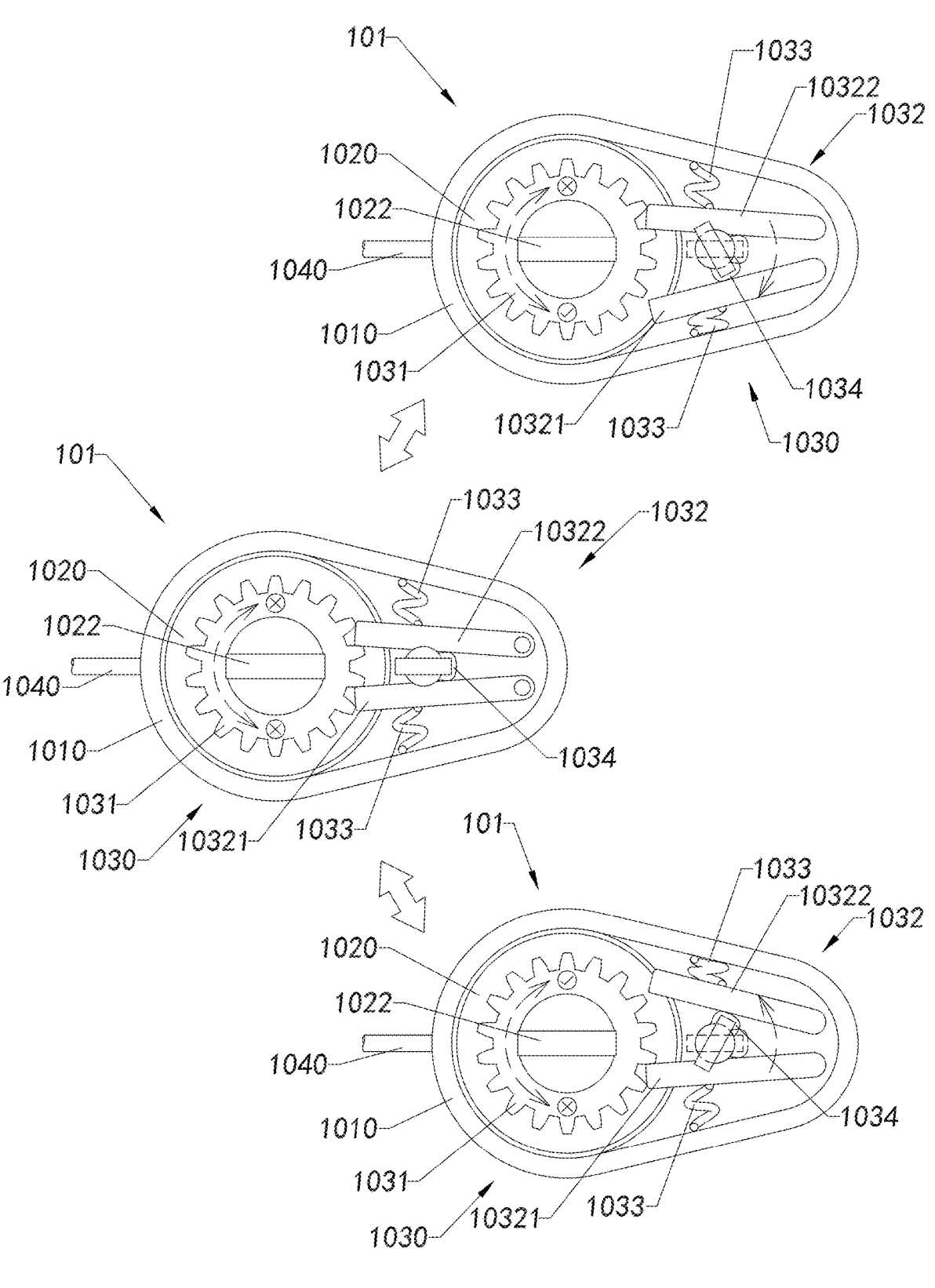
FIG. 19 illustrates a rotation process of the control unit of the fixation connector according to the above fifth preferred embodiment of the present invention.

FIG. 17 is a schematic diagram of the overall structure of a fixation connector according to a fifth preferred embodiment. The fixation connector 101 comprises a housing 1010, a plug unit 1020, a control unit 1030, and a fixation cable 1040. During surgery, small surgical instruments are suitable for hanging and fixing to the fixation cable 1040, the plug unit 1020 is suitable for plugging and fixing to the housing 1010, the fixation cable 1040 is connected to the housing 1010 and the plug unit 1020, the control unit 1030 is coaxially connected to the plug unit 1020 to control the pivot of the plug unit 1020. Then the fixation cable is wrapped around the plug unit 1020 to control the length of the fixation cable 1040, meeting different requirements. Suspension and fixation of surgical instruments.

The housing 1010 comprises a receiving cavity 1011, an inlet hole 1013, a communication hole 1014, and a surrounding wall 1012. The receiving cavity 1011 extends inward from the end of the housing 1010 to accommodate the plug unit 1020. The inlet hole 1013 extends inward from the surface of the surrounding wall 1012 to penetrate the surrounding wall 1012. The fixation cable 1040 enters the inlet hole 1013 and is fixed around the plug unit 1020. The communication hole 1014 extends inward from the surface of the surrounding wall 1012 to penetrate the surrounding wall 1012.

The housing 1010 is preferably made of transparent material. When the insertion unit 1020 is inserted into the receiving cavity 1011 of the housing 1010, the fixation cable 1040 is wrapped and fixed to the insertion unit 1020. Made of transparent material, it is convenient for medical staff to observe the fixing situation of the fixation cable 1040 and avoid the fixation cable 1040 from being wrapped and locked.

According to this fifth preferred embodiment, the number of inlet holes 1013 is set to one. The number of communication holes 1014 is set to two. In detail, to facilitate the explanation of the arrangement positions of the communication holes 1014, the first communication hole 1014 is specified as the first communication hole 1014A. The other communication hole 1014 is specified as the second communication hole 1014B. Furthermore, the inlet holes 1013 and the first communication hole 1014A are longitudinally arranged on the surrounding wall 1012. The first communication hole 1014A and the second communication hole 1014B are symmetrically arranged on two sides of the surrounding wall 1012. In other words, the first communication hole 1014A and the second communication hole 1014B are symmetrically arranged on two sides of the surrounding wall 1012. The communication hole 1014A and the second communication hole 1014B are symmetrically distributed axially on the surrounding wall 1012.

The plug unit 1020 comprises an inner core 1021 and a grip portion 1022. The grip portion 1022 is connected to one end of the inner core 1021 and protrudes from the housing 1010. The inner core 1021 is suitable for insertion into the receiving cavity 1011 of the housing 1010. The operator rotates the grip portion 1022 to drive the inner core 1021 to pivot from the receiving cavity 1011, thereby fixing the fixation cable 1040 around the inner core 1021.

Furthermore, the inner core 1021 comprises a surrounding portion 10211, a fixation portion 10212, and a protruding ring 10213. The protruding ring 10213 extends outward from the surface of the inner core 1021 and is annular, dividing the inner core 1021 into the surrounding portion 10211 and the fixation portion 10212. When using the fixation connector 101, one end of the fixation cable 1040 surrounds the surrounding portion 10211 and the other end is connected to the fixation portion 10212. The pivot of the inner core 1021 is controlled by the control unit 1030 to achieve the purpose of fixing the fixation cable 1040. At the same time, the fixation cable 1040 can be adjusted. Length to facilitate the fixation of different surgical instruments.

The plug unit 1020 further has a limitation hole 1023 and a fixation hole 1024. The limitation hole 1023 extends inward from the surface of the surrounding portion 10211 of the inner core 1021. The fixation hole 1024 extends inward from the surface of the fixation portion 10212.

It is worth mentioning that the limitation hole 1023 and the fixation hole 1024 respectively pass horizontally through the surrounding portion 10211 and the fixation portion 10212 of the inner core 1021. The limitation hole 1023 passes through the surrounding portion 10211 to form a limitation channel. The fixation hole 1024 passes through the fixation portion 10212 to form a fixation channel. The limitation channel and the fixation channel are perpendicular to the perpendicular line of the inner core 1021. In other words, the limitation channel and the fixation channel are set to pass horizontally through the inner core, providing a channel for fixing the fixation cable 1040.

It is worth mentioning that when the plug unit 1020 is plugged into the receiving cavity 1011 of the housing 1010, the inner core 1021 is accommodated in the receiving cavity 1011. The grip portion 1022 protrudes from the housing 1010. Furthermore, the inlet hole 1013 and the limitation hole 1023 are connected to each other. The communication hole 1014 and the fixation hole 1024 are connected to each other. In other words, the inlet hole 1013 and the limitation hole 1023 are horizontally and coaxially arranged. The communication hole 1014 and the fixation hole 1024 are also horizontally and coaxially arranged, so that one end of the fixation cable 1040 is fixed to the front end of the inner core 1021 by passing through the inlet hole 1013 and the limitation hole 1023 respectively. The other end of the fixation cable 1040 passes through the communication hole 1014 and the fixation hole 1024 respectively. Then, through the rotation of the control unit 1030, it drives the fixation cable 1040 to be fixed to the front end of the inner core 1021. The relative rotation between the plug unit 1020 and the housing achieves the purpose of fixing the fixation cable 1040, facilitating the fixation of small surgical instruments.

The control unit 1030 comprises a ratchet 1031, a stopper 1032, an elastic element 1033, and a guide member 1034. The ratchet 1031 is longitudinally and coaxially connected to the inner core 1021. The stopper 1032 is rotatably set at the end of the housing 1010. In other words, one end of the stopper 1032 is fixed to the housing 1010. The other end is pressed against the ratchet 1031 to control the rotation of the ratchet 1031, thereby controlling the fixed length of the fixation cable 1040. One end of the elastic element 1033 is connected to the housing 1010. The other end is fixed to the stopper 1032. Furthermore, the elastic element 1033 forces the stopper 1032 to always maintain contact with the ratchet 1031.

The guide member 1034 is also rotatably arranged at one end on the housing 1010. In other words, one end of the guide member 1034 is rotatably connected to the housing 1010. The other end is in contact with the stopper 1032 to limit the rotation direction of the ratchet 1031.

Furthermore, according to this fifth preferred embodiment, the stopper 1032 comprises a first stopper 10321 and a second stopper 10322, which are respectively disposed on two sides of the guide member 1034. The guide member 1034 can rotate and abut against the first stopper 10321 and the second stopper 10322 to limit the rotation direction of the ratchet 1031. According to this preferred embodiment, the number of elastic elements 1033 is also set to two, and two of the elastic elements 1033 are respectively connected to the first stopper 10321 and the second stopper 10322, forcing the first stopper 10321 and the second stopper 10322 to always maintain contact with the ratchet 1031.

Furthermore, for ease of explanation, in the present invention, the position of the first stopper 10321 is defined as the left side. The position of the second stopper 10322 is defined as the right side.

When the guide member 1034 rotates to be in contact with the first stopper 10321, the first stopper 10321 and the ratchet 1031 are separated and not in contact. The second stopper 10322 and the ratchet 1031 are in contact, so the ratchet 1031 can rotate counterclockwise. The elastic element 1033 forces the second stopper 10322 to always be in contact with the ratchet 1031, so the ratchet 1031 cannot rotate clockwise. When the guide member 1034 rotates to be in contact with the second stopper 10322, the first stopper 10321 and the ratchet 1031 are in contact. The second stopper 10322 and the ratchet 1031 are separated from each other, so the ratchet 1031 can rotate clockwise. The elastic element 1033 forces the first stopper 10322 to always maintain contact with the ratchet 1031, so the ratchet 1031 cannot rotate counterclockwise.

By rotating the guide member 1034, the position relationship between the first stopper 10321, the second stopper 10322. The ratchet 1031 is controlled, so that the ratchet 1031 can rotate in both directions, thereby driving the inner core 1021 to rotate in both directions. The contraction and stretching of the fixation cable 1040 are controlled to easily change the length of the fixation cable 1040. Moreover, when the ratchet 1031 rotates in the same direction, it cannot be reversed and can only be controlled by the guide member 1034 to adjust the rotation direction, so that the fixation cable 1040 can reach a certain length for easy fixation.

It is worth mentioning that, according to this fifth preferred embodiment, the ratchet 1031, the stopper 1032, the elastic element 1033. The guide member 1034 are all arranged on the same plane for the rotation switching of the guide member 1034, and are in contact with the first stopper 10321 and the second stopper 10322, respectively. At the same time, the elastic element 1033 forces the first stopper 10321 and the second stopper 10322 to abut against the ratchet 1031, completing the length adjustment and fixation of the fixation connector 101 after length adjustment, to meet the fixation of different small surgical instruments, improve surgical efficiency and safety.

It is worth mentioning that when the operator rotates the grip portion 1022 counterclockwise, the guide member 1034 and the second stopper 10322 come into contact with each other. During rotation, the second stopper 10322 is forced against the ratchet 1031 by the elastic element 1033. When rotating counterclockwise, the teeth of the ratchet 1031 press against the second stopper 10322, compressing the elastic element 1033, allowing the ratchet 1031 to easily complete counterclockwise rotation. When rotating clockwise, the teeth of the ratchet 1031 push the second stopper 10322, causing the elastic element 1033 to stretch. The elastic element 1033 has a certain tensile limit. When the elastic element 1033 reaches the tensile limit, the ratchet 1031 cannot rotate clockwise.

When the operator rotates the grip portion 1022 clockwise, the guide member 1034 and the first stopper 10321 come into contact with each other. When rotating, the first stopper 10321 is forced against the ratchet 1031 by the elastic element 1033. When rotating clockwise, the teeth of the ratchet 1031 press against the first stopper 10321, compressing the elastic element 1033, allowing the ratchet 1031 to easily complete clockwise rotation; When rotating counterclockwise, the teeth of the ratchet 1031 push the first stopper 10321, causing the elastic element 1033 to stretch. The elastic element 1033 has a certain tensile limit. When the elastic element 1033 reaches the tensile limit, the ratchet 1031 cannot complete counterclockwise rotation.

Therefore, the length of the fixation connector 101 can be adjusted through the control unit 1030. The adjusted length is very convenient for fixing, making it easy to fix different small surgical instruments during surgery.

The following is an exemplary introduction to the usage process of the fixation connector 101 according to this preferred embodiment. The method of using the fixation connector 101 comprises the following steps:

(a) Fixing the front end of the fixation cable 1040 to the surrounding portion 10211 of the inner core 1021;

(b) Fixing the rear end of the fixation cable 1040 to the fixation portion 10212 of the inner core 1021; and (c) Adjusting the guide member 1034, rotating the grip portion to drive the ratchet 1031 to rotate, and adjust the fixation cable 1040 to the appropriate length.

In detail, in step (a), the front end of the fixation cable 1040 is inserted into the inlet hole 1013 and the limitation hole 1023, the grip portion 1022 is rotated to fix the front end of the fixation cable 1040 to the surrounding portion 10211. The number of turns the fixation cable 1040 is wrapped around the surrounding portion 10211 can be adjusted according to actual usage, as long as it can be fixed to the surrounding portion 10211. One skilled in the art should understand that the fixing method of the front end of the fixation cable 1040 and the surrounding portion 10211 is not a limitation of the present invention, so the length of the fixation connector 101 can be easily fixed after adjustment.

In detail, in step (b), according to this preferred embodiment, the rear end of the fixation cable 1040 is inserted into the communication hole 1014 and the fixation hole 1024, the grip portion 1022 is rotated to fix the rear end of the fixation cable 1040 in the fixation portion 10212

In step (c), the guide member 1034 adjusted, wherein the grip portion 1022 is rotated to drive the ratchet 1031 to rotate, and the fixation cable 1040 is adjusted to a suitable length. The part of the fixation cable 1040 outside the housing 1010 is a suspension area for small surgical instruments. By rotating the ratchet 1031, the length of the fixation cable 1040 wrapped around the fixation portion 1024 at the end of the fixation cable 1040 is changed, thereby changing the length of the fixation cable 1040 outside the housing 1010 to achieve the change of the length of the fixation connector 101 to fix different small surgical instruments.

Figure 20:
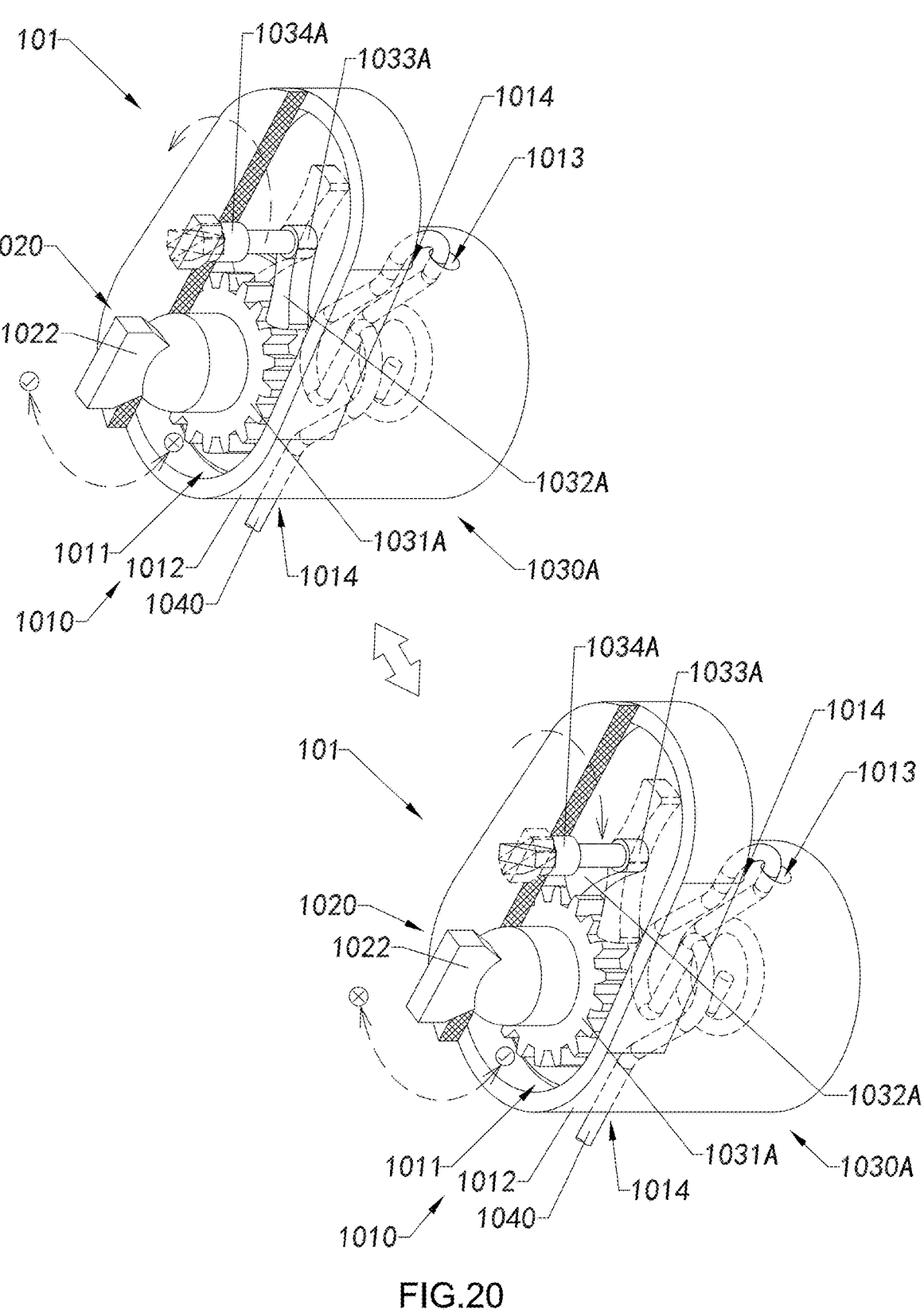
FIG. 20 is a perspective view of a fixation connector according to a sixth preferred embodiment of the present invention.

As illustrated in FIG. 20, another preferred embodiment of the present invention provides a fixation connector. The fixation connector is an alternative mode of the fifth preferred embodiment. Compared to the fifth preferred embodiment, the control unit 1030 is different.

In detail, according to this preferred embodiment, the control unit 1030A comprises a ratchet 1031A, a stopper 1032A, an elastic element 1033A, and a guide member 1034A. The ratchet 1031A is longitudinally and coaxially connected to the inner core 1021, and one end of the guide member 1034A is rotatably connected to the ratchet 1031A. The guide member 1034A protrudes from a portion of the ratchet 1031A. In detail, one end of the guide member 1034A protrudes from the outer circumference of the ratchet 1031A. The elastic element 1033 A is set at the top of the guide member 1034A to connect the stopper 1032A. In order to allow the stopper 1032A to be rotatably installed at the top of the guide member 1034A, one end of the stopper 1032A is connected to the elastic element 1033A. The other end is connected to the ratchet 1031A when it rotates. The claws are against each other.

In more detail, the ratchet 1031A, the stopper 1032A. The guide member 1034A are all arranged on the same plane to facilitate the rotation switching of the stopper 1032A, control the rotation direction of the ratchet 1031A, and complete the length adjustment and fixation of the fixation connector 101 to meet the fixation of different small surgical instruments, improve surgical efficiency and safety.

Furthermore, when the ratchet 1031A needs to rotate to the right, the stopper 1032A rotates to the right of the ratchet 1031A through the guide member 1034. When the ratchet 1031A needs to rotate to the left, the stopper 1032A rotates to the left of the ratchet 1031A through the elastic element 1033A. Therefore, the length of the fixation connector 101 can be adjusted through the control unit 1030A. The adjusted length is very convenient for fixing, making it easy to fix different small surgical instruments during surgery.

Figure 21:
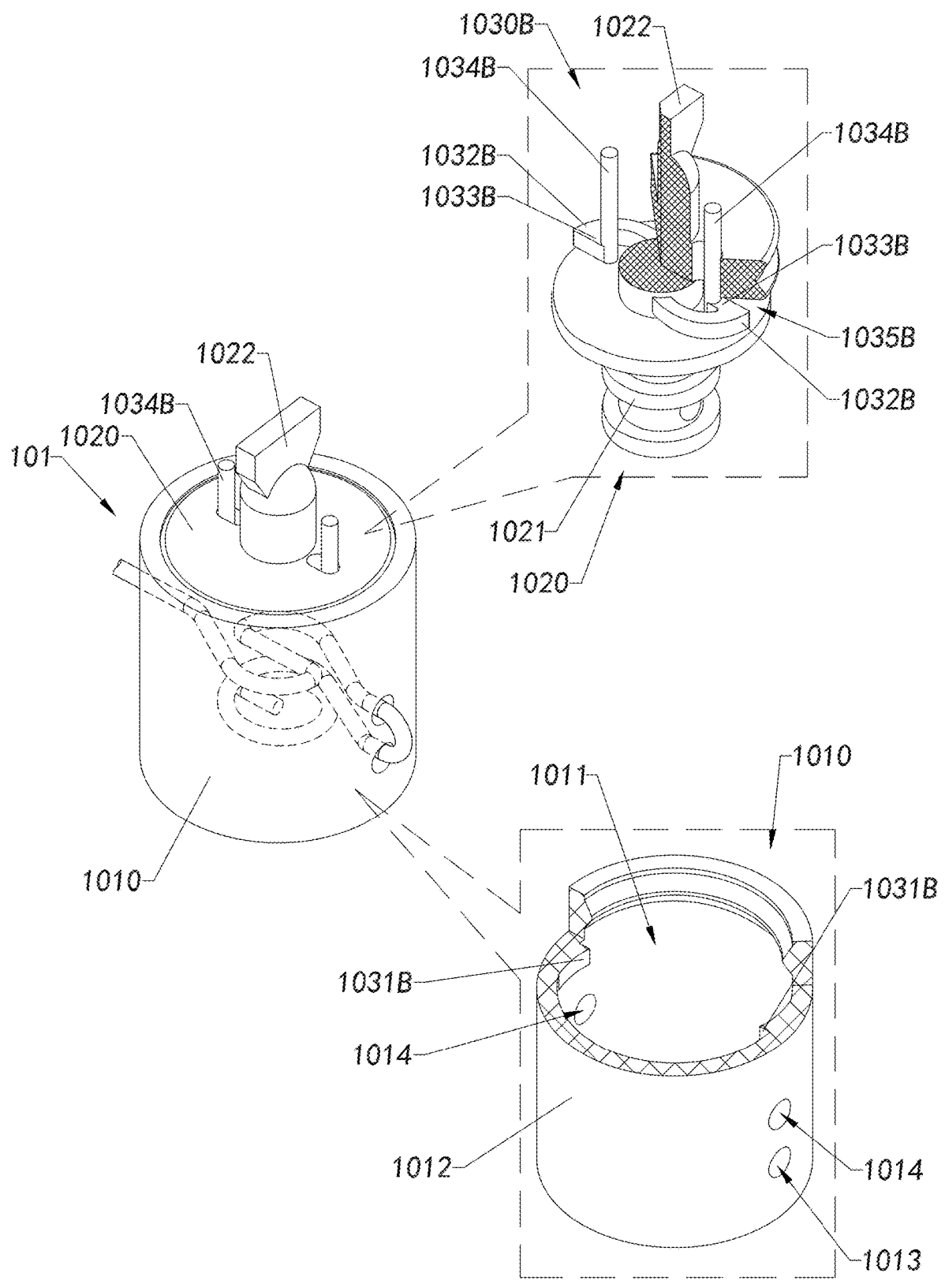
FIG. 21 is a perspective view of a fixation connector according to a seventh preferred embodiment of the present invention.
Figure 22:
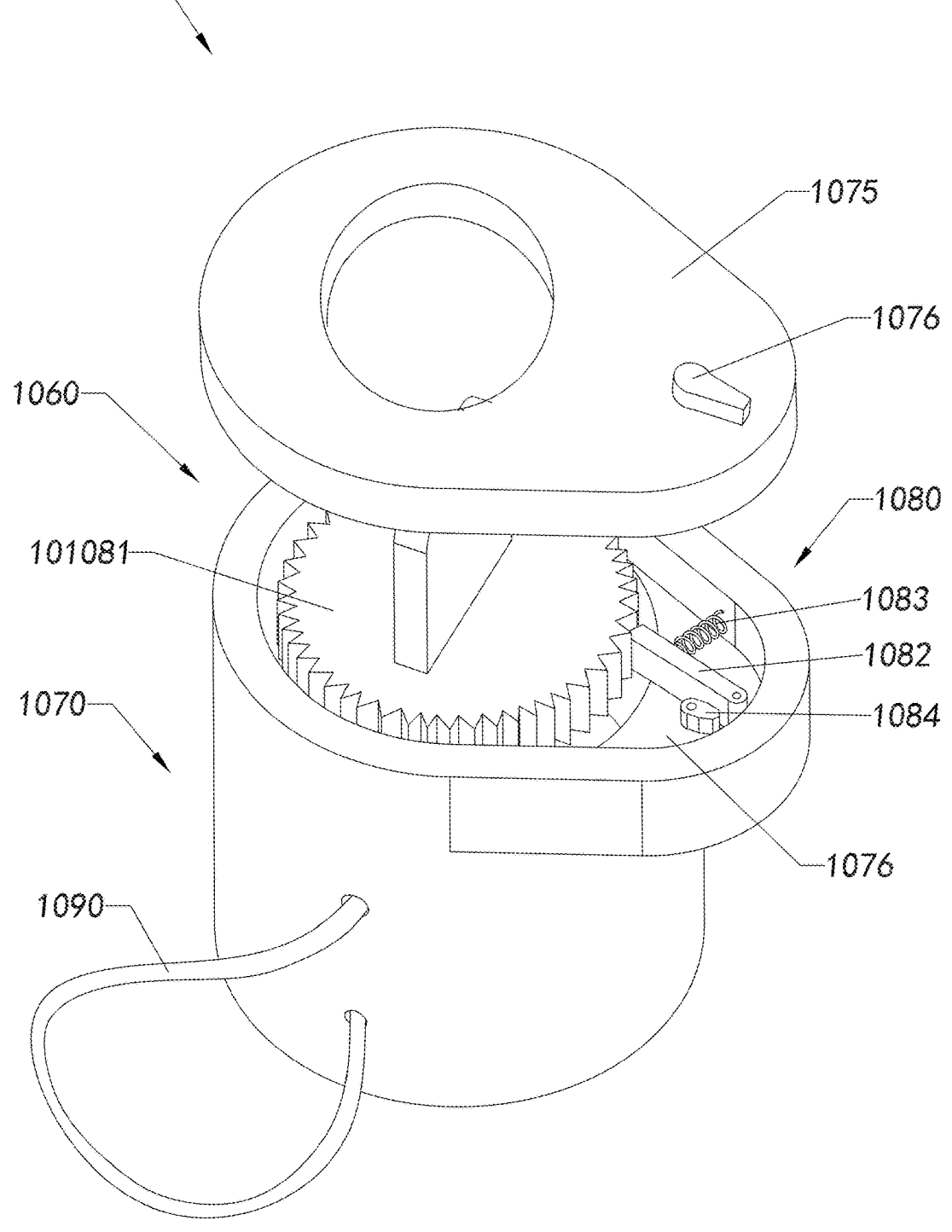
FIG. 22 is a perspective view of a fixation connector according to a eighth preferred embodiment of the present invention.
Figure 23:
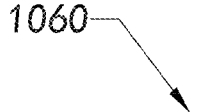
FIG. 23 illustrates the structure of a core body of the fixation connector according to the above eighth preferred embodiment of the present invention.
Figure 23:
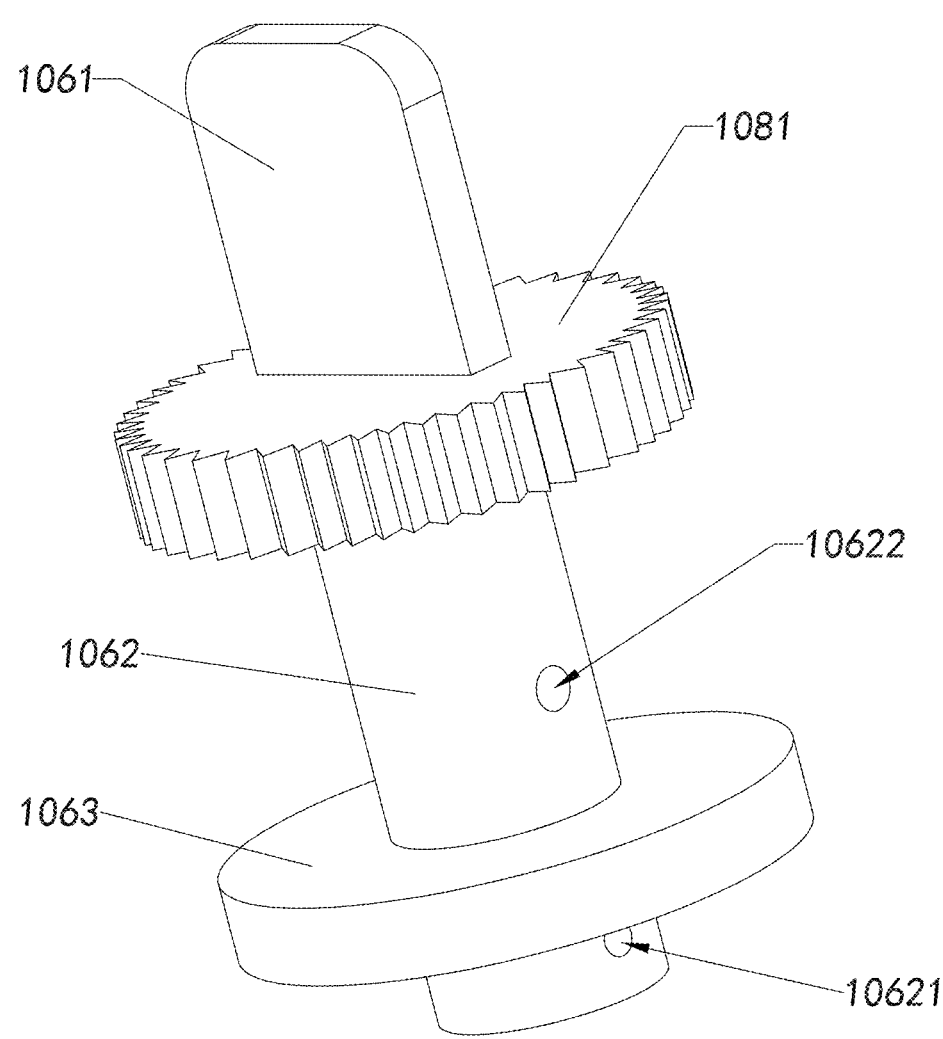
Figure 24:
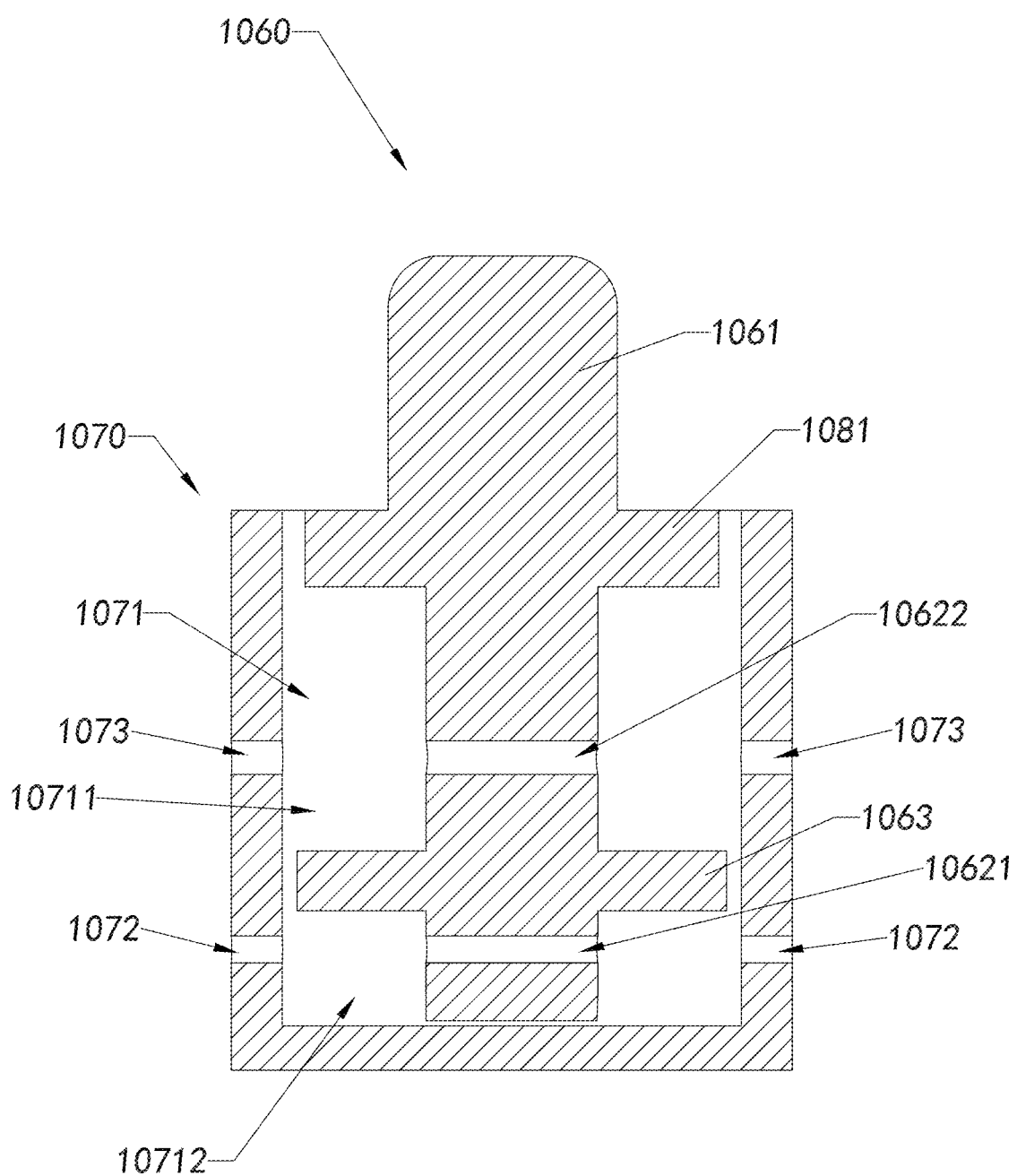
FIG. 24 is a cross-sectional view of the fixation connector according to the above eighth preferred embodiment of the present invention.
Figure 25:
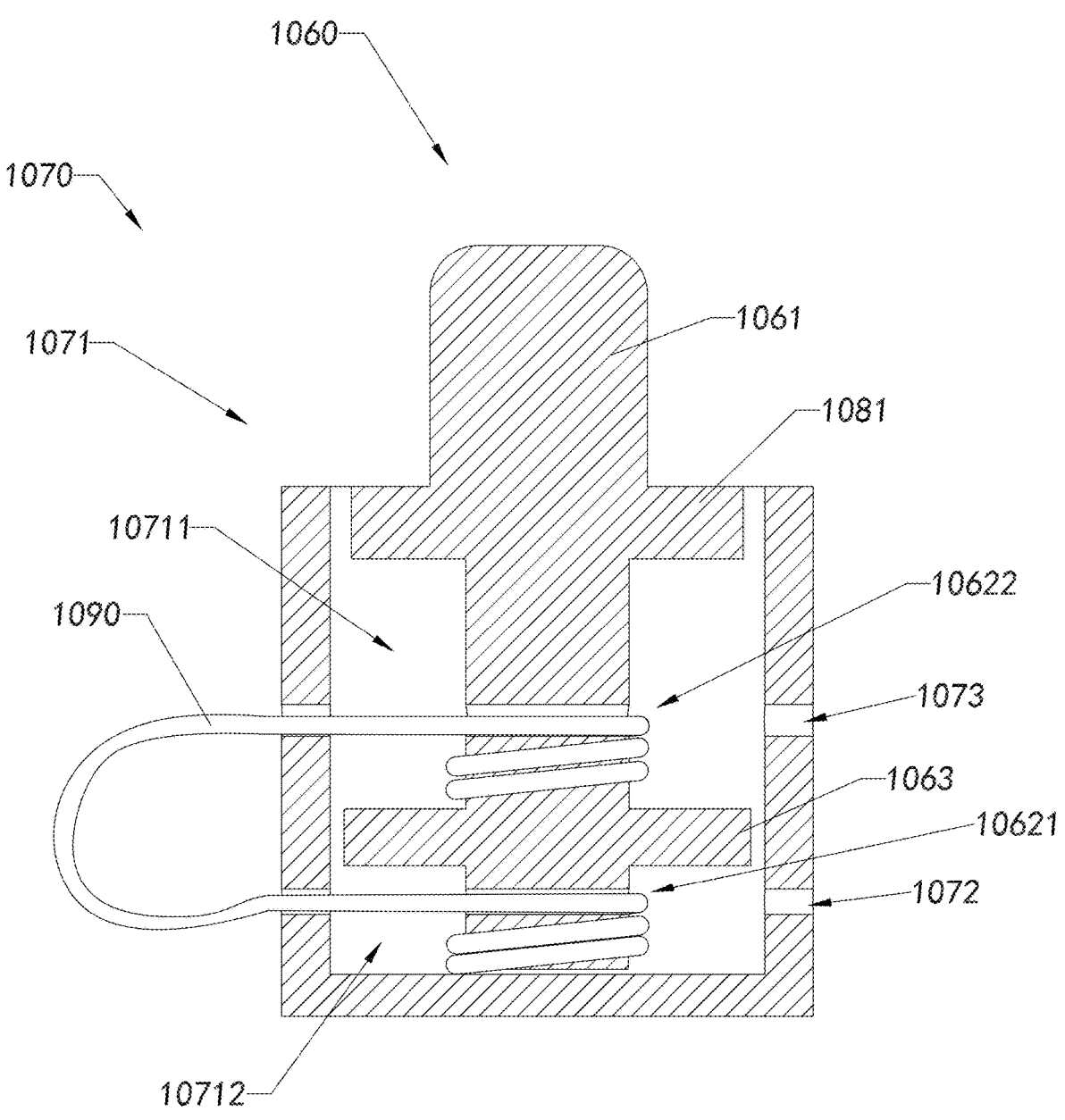
FIG. 25 is another cross-sectional view of the fixation connector according to the above eighth preferred embodiment of the present invention, wherein the fixation connector is wound with a fixation cable.
Figure 26:
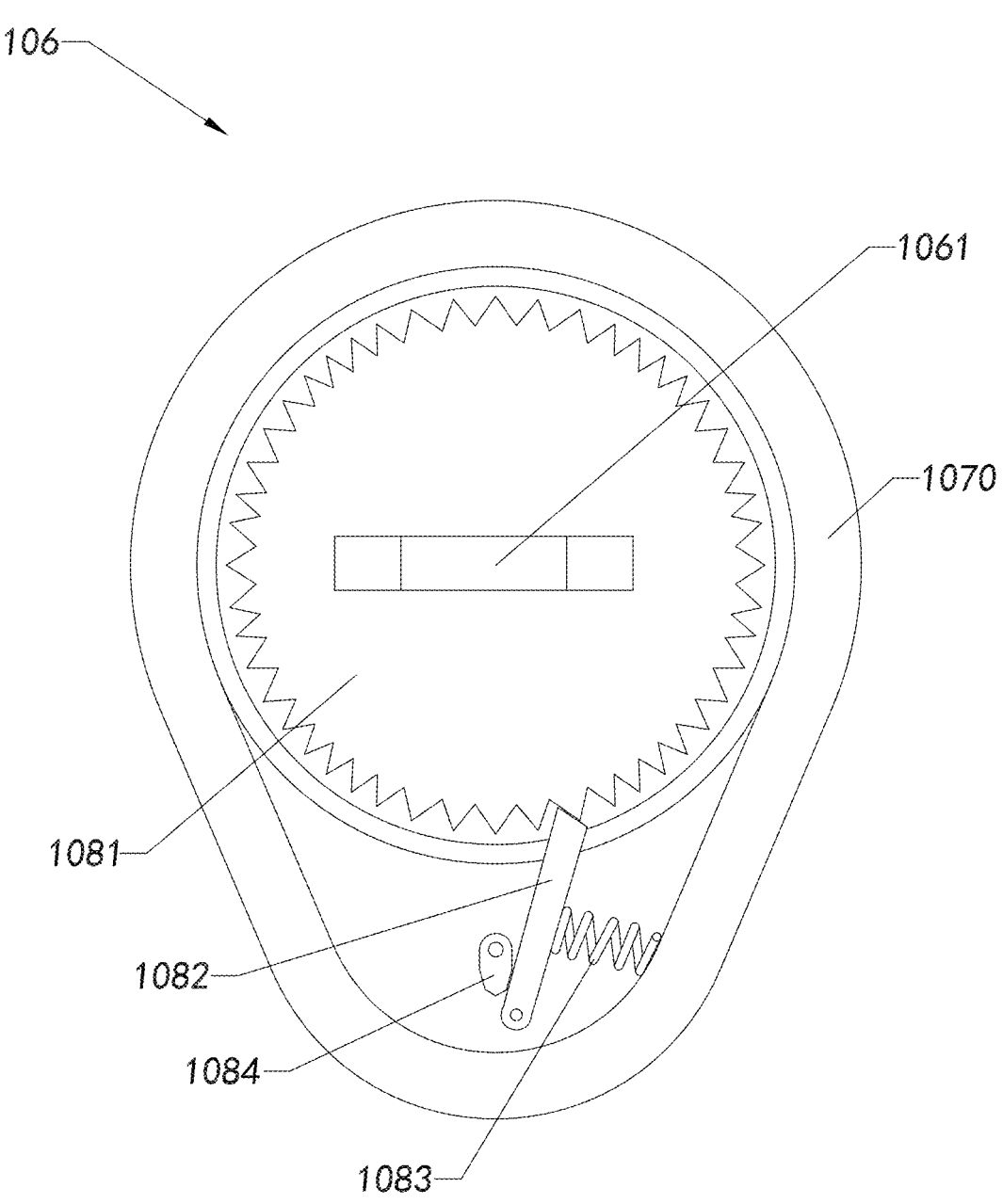
FIG. 26 illustrates a locking state of a ratchet locking component of the fixation connector according to the above eighth preferred embodiment of the present invention.
Figure 27:
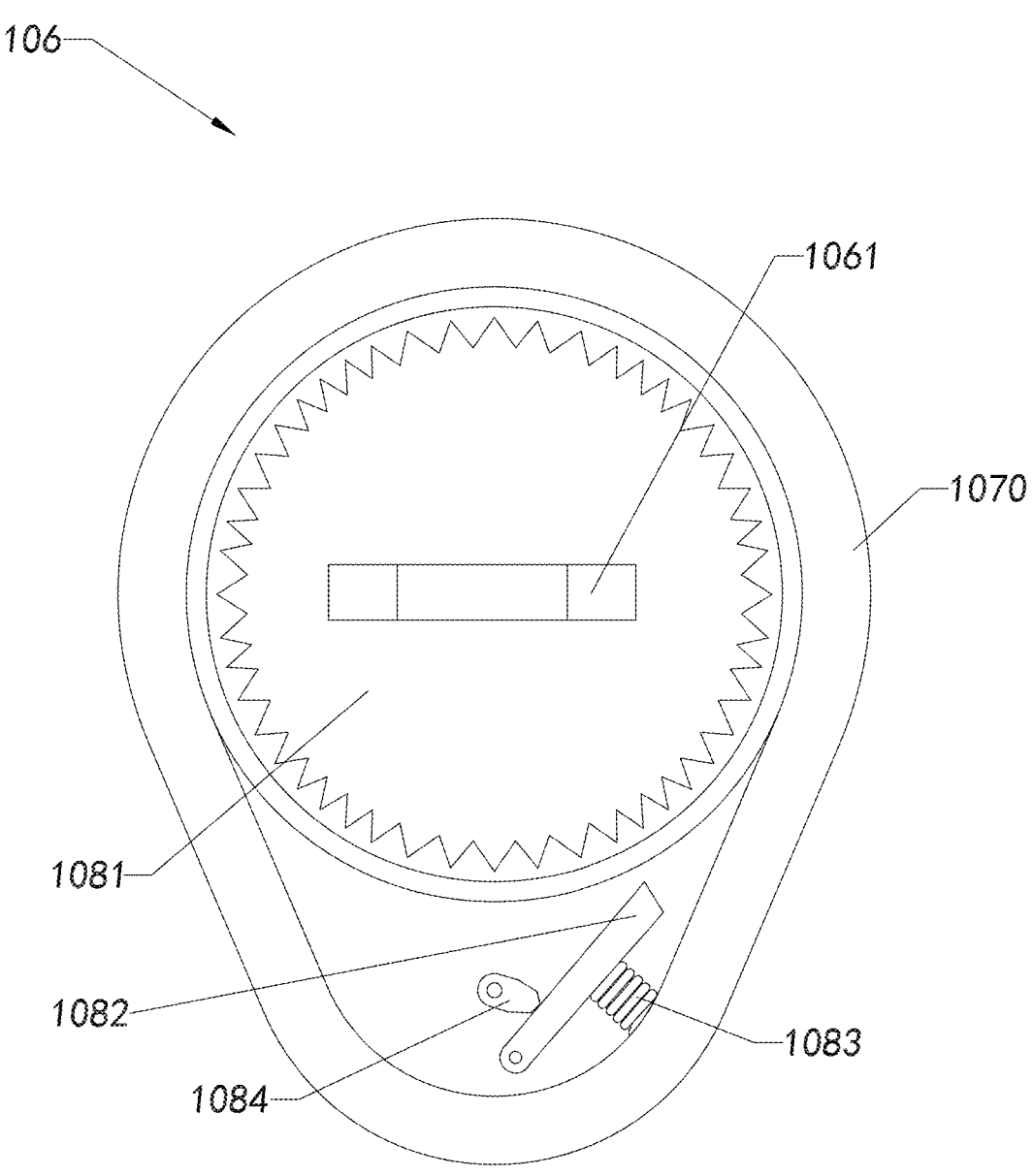
FIG. 27 illustrates an unlocked state of the ratchet locking component of the fixation connector according to the above eighth preferred embodiment of the present invention.
Figure 28:
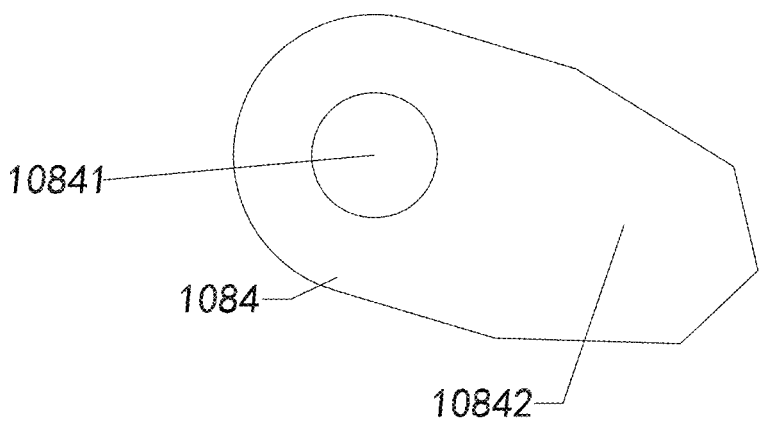
FIG. 28 illustrates a reversing component of the fixation connector according to the above eight preferred embodiment of the present invention.

FIG. 21 illustrates in a fixation connector according to a seventh preferred embodiment of the present invention. The fixation connector is an alternative of the fifth preferred embodiment.

In detail, according to this seventh preferred embodiment, the control unit 1030B comprises a ratchet 1031B and a stopper 1032B. The ratchet 1031B is arranged on the inner wall of the housing 1010, and is close to the outside of the housing 1010. The stopper 1032B is arranged on the inner core 1021 of the plug unit 1020. When the plug unit 1020 is inserted into the receiving cavity 1011 of the housing 1010, the ratchet 1031B and the stopper 1032B are in contact.

In more detail, the claws of the ratchet 1031B are distributed in a circular manner from the inner wall of the housing 1010, and each claw extends obliquely from the inner wall. The stopper 1032B extends obliquely from the inner core 1021 to engage with the claws, so that the stopper 1032B can only rotate in one direction. When rotated in the opposite direction, the protruding end of the claw and the protruding end of the stopper 1032B are in contact to block the reverse rotation of the stopper 1032B.

The control unit 1030B further comprises a traction member 1033B, a control member 1034B, and an installation groove 1035B. The control member 1034B is set on the grip portion 1022 of the plug unit 1020. The installation groove 1035B extends inward from the surface of the inner core 1021 to accommodate the stopper 1032B. The shape and quantity of the installation groove 1035B are consistent with those of the stopper 1032B. The traction member 1033B is connected to the control member 1034B. The other end is connected to the stopper 1032B. The operator can insert the stopper 1032B into the installation through the control member 1034B. Slot 1035B.

Furthermore, according to this preferred embodiment, the number of the stoppers 1032B is preferably set to two. The two stoppers 1032B can be directly connected to the control member 1034B through a separate traction member 1033B. Through the control member 1034B, the traction member 1033B drives the stoppers 1032B to rotate along a predetermined trajectory into the installation chamber 1035B, which is accommodated in the installation chamber 1035B. This avoids mutual engagement between the stoppers 1032B and the ratchet 1031B, allowing the stoppers 1032B to rotate in the opposite direction. Based on this, the control unit 1030B can achieve forward and reverse rotation, thereby facilitating the change of the length of the fixation connector 101 to fix different small surgical instruments.

Furthermore, when the fixation connector 101 is adjusted to the appropriate length, the stopper 1032B is rotated out of the installation slot 1035B again through the control member 1034B, so that the stopper 1032B and the ratchet 1031B are engaged with each other to fix the length of the fixation connector 101.

Referring to FIGS. 22 to 28, a fixation connector 106 according to a eighth preferred embodiment of the present invention is illustrated.

The fixation connector 106 is used in head or neck housing surgery, especially in surgical work of head fixation and retraction systems, for fixing the pipelines and some small instruments required in surgery. One skilled in the art should understand that the fixation connector 106 can also be used in other places that require fixation, including but not limited to the above-mentioned usage scenarios and fields.

During the surgical process, fixed pipelines and surgical instruments may need to be fixed due to changes in the surgical procedure and actual circumstances, in order to increase stability while preventing displacement of pipelines or surgical instruments, and preventing harm to patients caused by pipeline displacement or surgical instrument displacement. The fixation connector 106 can fix pipelines or surgical devices in the appropriate position and lock them to prevent displacement of pipelines or surgical instruments during surgery.

It is worth mentioning that the fixation connector 106 can switch between a locked state and an unlocked state, so that the fixation connector 106 can adjust the position of the pipeline and surgical instruments according to the actual needs of the surgery, and fix the position. In other words, the fixation connector 106 can be reused and reused repeatedly. And it can be used in a plurality of combination to achieve the desired fixed effect.

In detail, the fixation connector 106 may comprise a core 1060, a housing 1070, a ratchet locking component 1080, and a fixation cable 1090. The ratchet locking component 1080 is matched with the core 1060 and installed on the housing 1070. The fixation cable 1090 is suitable for being fixed by the core 1060.

The core 1060 wraps the fixation cable 1090 into the housing 1070 to form a closed ring with the housing 1070, which is used to fix it on the head retraction system. The pipeline and surgical instruments can be lifted onto the fixation connector 106 through the closed ring.

The ratchet locking component 1080 restricts the rotation of the core 1060, thereby limiting the length of the fixation cable 1090. In other words, the ratchet locking component 1080 can be used to control the distance between the pipeline and surgical instruments fixed by the fixation cable 1090 and the head retraction system, so as to enable the pipeline and surgical instruments to reach the appropriate surgical position and promote the favorable progress of the surgery.

The core 1060 comprises a grip portion 1061, a main body shaft 1062, and a spacer ring 1063. The grip portion 1061 is flat and integrally installed at one end of the main body shaft 1062. The main body shaft 1062 is cylindrical. The width of the grip portion 1061 is slightly larger than the diameter of the main body shaft 1062. The grip portion 1061 and the main body shaft 1062 are located on the same axis, so that when the grip portion 1061 is rotated, it will drive the main body shaft 1062 to rotate.

The spacer ring 1063 is installed on the main shaft 1062 and divides the main shaft 1062 into upper and lower parts. In detail, the diameter of the spacer ring 1063 is larger than the diameter of the main body shaft 1062, which means that the spacer ring 1063 protrudes around the main body shaft 1062. The thickness of the spacer ring 1063 is smaller than the diameter of the main body shaft 1062.

The main shaft 1062 further has a locking hole 10621 and a sealing hole 10622. The locking hole 10621 is located below the spacer ring 1063 and arranged perpendicular to the axis of the main body shaft 1062. The diameter of the locking hole 10621 is slightly larger than that of the fixation cable 1090 to facilitate the insertion of the fixation cable 1090.

The sealing hole 10622 is arranged above the spacer ring 1063 and perpendicular to the axis of the main body shaft 1062. The diameter of the sealing hole 10622 is slightly larger than that of the fixation cable 1090 to facilitate the insertion of the fixation cable 1090.

The housing 1070 has an installation cavity 1071. The core 1060 is rotatably installed in the installation cavity 1071. The diameter of the spacer ring 1063 is slightly smaller than that of the installation cavity 1071, so that the spacer ring 1063 can be accommodated by the installation cavity 1071.

The housing 1070 is cylindrical in shape. The installation chamber 1071 is also cylindrical in shape. In other words, the installation chamber 1071 is coaxially arranged on the housing 1070, so that the housing 1070 is cup-shaped. The core 1060 is installed inside the installation chamber 1071.

In detail, the gap between the spacer ring 1063 and the inner wall of the installation chamber 1071 should be smaller than the diameter of the fixation cable 1090 to prevent the fixation cable 1090 from exchanging positions through the spacer ring 1063.

The spacer ring 1063 divides the installation cavity 1071 into two upper and lower cavities, namely the first winding cavity 10711 and a second winding cavity 10712.

The housing 1070 further has a fixation hole 1072 and a pair of threading holes 1073. The fixation hole 1072 is set on the side wall of the housing 1070 and coaxial with the locking hole 10621. The threading hole 1073 is symmetrically set on the side wall of the housing 1070 and coaxial with the sealing hole 10622.

In other words, the fixation hole 1072 and the locking hole 10621 are located on the same straight line. The diameters of the fixation hole 1072 and the locking hole 10621 are the same. The threading hole 1073 and the sealing hole 10622 are located on the same straight line. The threading hole 1073 and the sealing hole 10622 have the same diameter.

One skilled in the art should understand that when one end of the fixation cable 1090 passes through the fixation hole 1072 of the housing 1070 and continues to be inserted into the locking hole 10621 of the core 1060, rotating the grip portion 1061 drives the core 1060 to rotate, causing displacement between the locking hole 10621 and the fixation hole 1072. The locking hole 10621 and the fixation hole 1072 are offset from each other, thereby driving the fixation cable 1090 to roll into the second winding cavity 10712 below the spacer ring 1063, thereby fixing one end of the fixation cable 1090 to the housing 1070.

At this point, the other end of the fixation cable 1090 can be passed through the position to be fixed and then inserted into the threading hole 1073 of the housing 1070, and continuously inserted into the sealing hole 10622 of the core 1060. At this time, rotating the grip portion 1061 drives the core 1060 to rotate. The sealing hole 10622 and the threading hole 1073 produce relative displacement. The sealing hole 10622 and the threading hole 1073 are offset from each other, so that the fixation cable 1090 is rolled up above the spacer ring 1063, In other words, the first winding cavity 10711, to complete the fixing of the connector 106 at the position to be fixed. The pipeline and surgical instruments can be placed on top of the fixation connector 106. Fixed on cable 1090 and lifted for support.

It is worth mentioning that the first winding cavity 10711 and the second winding cavity 10712 are separated by the spacer ring 1063. The fixation cable 1090 located in the first winding cavity 10711 will not affect the fixation cable 1090 in the second winding cavity 10712. In other words, during the rotation of the core 1060, the fixation cable 1090 will not entangle or knot with each other, and it is also convenient for the fixation cable 1090 to be pulled out from the first winding cavity 10711 and the second winding cavity 10712, so that the fixation connector 106 can flexibly adjust the length of the fixation cable 1090, and greatly improve its performance. Reduced the failure rate of the fixation connector 106.

Furthermore, the first winding cavity 10711 and the second winding cavity 10712 can prevent excess fixation cables 1090 from being exposed outside the housing 1070. In other words, after the fixing connector 106 is fixed, the fixation cables 1090 will not be exposed, which does not affect the doctor's surgery and prevents tripping, scratching, or puncturing of the doctor's surgery.

It is worth mentioning that the housing 1070 is made of transparent plastic as a whole, which means that during the rotation of the core 1060, it is easy to observe the winding situation of the fixation cable 1090 inside the housing 1070, and it is convenient to determine how much length can still be rolled in and out. There will be no situation where the fixation cable 1090 falls off from the core 1060 and the housing 1070 due to insufficient length, which increases the safety of fixation and prevents fixation failure.

It is worth mentioning that the ratchet locking component 1080 can limit and adjust the rotation of the core 1060, In other words, adjust the length of the fixation cable 1090. By controlling the length of the fixation cable 1090 exposed outside the housing 1070, the fixed position of the fixation connector 106 for fixing the tubing and surgical instruments can be controlled.

In detail, the ratchet locking component 1080 may comprise a ratchet 1081, a brake member 1082, an elastic component 1083, and a reversing component 1084.

The diameter of the ratchet 1081 is slightly smaller than that of the installation cavity 1071. The ratchet 1081 is installed between the grip portion 1061 and the main body shaft 1062. It can be understood that the ratchet 1081 is rigidly connected to the main body shaft 1062. When the grip portion 1061 rotates, it can drive the ratchet 1081 to rotate. In other words, when the ratchet 1081 rotates, it can drive the main body shaft 1061 to drive the fixation cable 1090 to be wound into the first winding cavity 10711 and the second winding cavity 10712.

The ratchet 1081 basically covers the opening position of the installation chamber 1071, and a support plate 1076 is also extended at the top of the housing 1070 for installing the brake component 1082, the elastic component 1083. The reversing component 1084.

One end of the brake component 1082 is rotatably mounted on the support plate 1076 of the housing 1070. The other end rests on the ratchet teeth of the ratchet 1081. The brake component 1082 and the ratchet 1081 are in the same plane. The brake component 1082 is in the form of a slender and hard strip, and its width is about the same as the thickness of the ratchet 1081. The brake component 1082 can be connected to the support plate 1076 of the housing 1070 by insertion or through a rotation shaft.

The elastic member 1083 is a spring, with one end fixed to the side of the support plate 1076 of the housing 1070. The other end elastically biased against the brake member 1082, causing the brake member 1082 to be elastically pressed against the ratchet teeth of the ratchet 1081.

The reversing component 1084 is located on the other side of the brake member 1082, which is the side without the elastic component 1083. The reversing component 1084 is a cam with a rotating end 10841 and a protruding end 10842, which can rotate around the rotating end 10841.

When the elastic bias of the brake component 1082 is on the ratchet teeth of the ratchet 1081, the rotating end 10841 of the reversing component 1084 tightly presses against the top of the pallet 1076 where the reversing component 1084 is pivot connected, to restrict the reversing component 1084. In other words, the elastic component 1083 not only elastically biases the brake component 1082 against the ratchet teeth of the ratchet 1081, but also elastically biases the brake component 1082 against the reversing component 1084. In other words, the brake component 1082 cannot rotate in the direction of the reversing component 1084, but can rotate in the direction of the elastic component 1083.

When in the locked state, the elastic member 1083 elastically biases the brake member 1082 against the ratchet teeth of the ratchet 1081. The rotating end 10841 of the reversing member 1084 is pressed against the reversing member 1084. At this time, when the ratchet 1081 rotates towards the reversing member 1084, the ratchet teeth will press against the brake member 1082, applying a force towards the reversing member 1084 to the brake member 1082. The brake member 1082 is blocked by the reversing member 1084, thereby restricting the movement of the ratchet 1081 towards the reversing member 1084.

When the ratchet 1081 moves towards the direction of the elastic member 1083, the ratchet teeth of the ratchet 1081 apply a pressure towards the direction of the elastic member 1083 to the braking member 1082, driving the braking member 1082 to compress the elastic member 1083 until the braking member 1082 no longer restricts the ratchet teeth of the ratchet 1081. The ratchet 1081 completes one tooth rotation. One skilled in the art should understand that the rotation of the ratchet 1081 towards the direction of the elastic member 1083 can be continuous and unidirectional.

Thread one end of the fixation cable 1090 through the fixation hole 1072 of the housing 1070 and continue to insert it into the locking hole 10621 of the core 1060. At this time, rotate the grip portion 1061 towards the direction of the elastic member 1083, which in turn drives the ratchet 1081 to rotate. The locking hole 10621 and the fixation hole 1072 are displaced. The locking hole 10621 and the fixation hole 1072 are offset from each other, thereby driving the fixation cable 1090 to be wound into the second winding cavity 10712 below the spacer ring 1063, thereby fixing one end of the fixation cable 1090 to the housing 1070.

At this point, the other end of the fixation cable 1090 can be threaded through the position to be fixed and then inserted into the threading hole 1073 of the housing 1070, and continuously inserted into the sealing hole 10622 of the core 1060. At this time, the grip portion 1061 is rotated towards the direction of the elastic member 1083, which in turn drives the ratchet 1081 to rotate. The sealing hole 10622 and the threading hole 1073 produce relative displacement. The sealing hole 10622 and the threading hole 1073 are offset from each other, thereby winding the fixation cable 1090 into the first winding cavity 10711 above the spacer ring 1063, completing the fixing of the fixation connector 106 at the position to be fixed. The tubing and surgical instruments can be placed on the fixation cable 1090 and lifted for support.

By continuously rotating the grip portion 1061, the length of the fixation cable 1090 exposed to the housing 1070 can be continuously reduced, thereby reducing the position of the fixed tubing and surgical instruments.

It is worth mentioning that the tooth rotation of the ratchet 1081 is segmented, In other words, for each tooth rotation of the ratchet 1081, the length of the fixation cable 1090 changes slightly. The changed length can also be locked, which is limited by the brake 1082, so that the fixation cable 1090 can be fixed in the appropriate position.

When in the unlocked state, the protruding end 10842 of the reversing member 1084 rotates around the rotating end 10841. The protruding end 10842 of the reversing member 1084 applies an outward thrust to the braking member 1082, moving the braking member 1082 in the direction of the elastic member 1083. The braking member 1082 compresses the elastic member 1083 and moves away from the ratchet teeth of the ratchet 1081. At this time, the rotation of the ratchet 1081 is not restricted by the braking member 1082.

In other words, the ratchet 1081 can rotate left and right without restriction. At this time, the fixation cable 1090 can be pulled out from the first winding cavity 10711 and the second winding cavity 10712, so that the fixation connector 106 can flexibly adjust the length of the fixation cable 1090. When adjusted to the appropriate length, the protruding end 10842 of the reversing member 1084 can be rotated away from the direction of the brake member 1082, In other words, the rotating end 10841 of the reversing member 1084 is attached to the brake member 1082. At this time, the brake member 1082 is supported by the elastic member 1083 and pressed against the reversing member 1084. And at the same time, it is pressed against the ratchet teeth of the ratchet 1081 to limit the rotation of the ratchet 1081 towards the direction of the reversing member 1084, completing the fixing work of the pipeline and surgical instruments.

One skilled in the art should understand that the locking hole 10621 and the fixation hole 1072 fix the fixation cable 1090 through the relative movement between the core 1060 and the housing 1070. The sealing hole 10622 and the threading hole 1073 fix the fixation cable 1090 through the relative movement between the core 1060 and the housing 1070. The above fixing method can quickly fix the fixation cable 1090 and lock it firmly, with a stable locking structure.

The reversing component 1084 only needs to be turned once to switch between the locked and unlocked states, greatly simplifying the operation steps of medical personnel, improving the efficiency of fixation, and reducing the use time of the fixation connector 106, which saves adjustment time during surgery.

The fixation connector 106 further comprises a cover plate 1075, which is connected to the pallet 1076 and encapsulates the ratchet locking component with the housing 1070 to ensure the integrity of the fixation connector 106.

The fixation connector 106 further comprises a directional switch 1076, which is set on the cover plate 1075 and connected to the directional component 1084, for controlling the directional component 1084 to switch between the locked and unlocked states of the fixation connector 106, facilitating quick operation by doctors.

Figure 29:
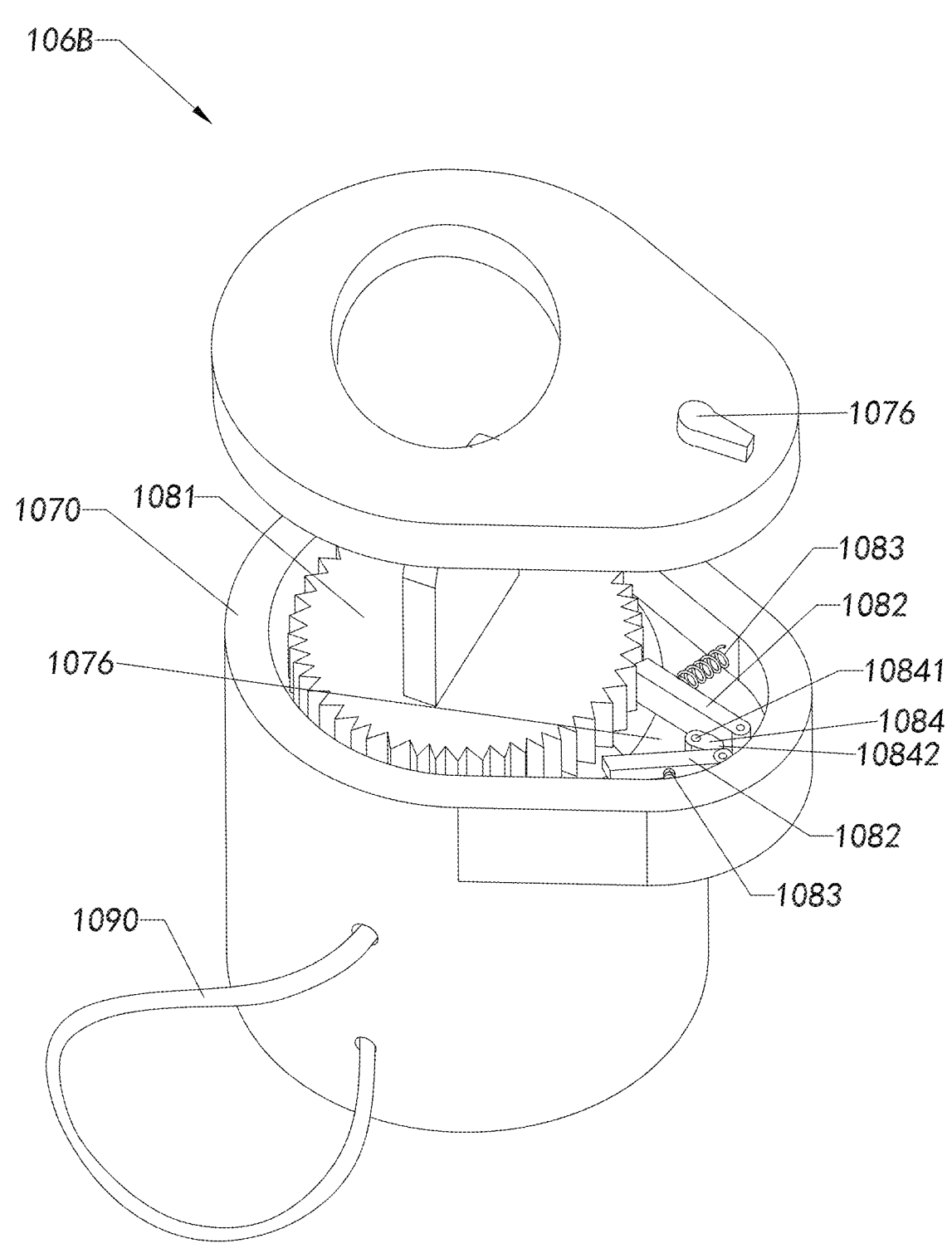
FIG. 29 is a perspective view of a fixation connector according to a ninth preferred embodiment of the present invention.
Figure 30:
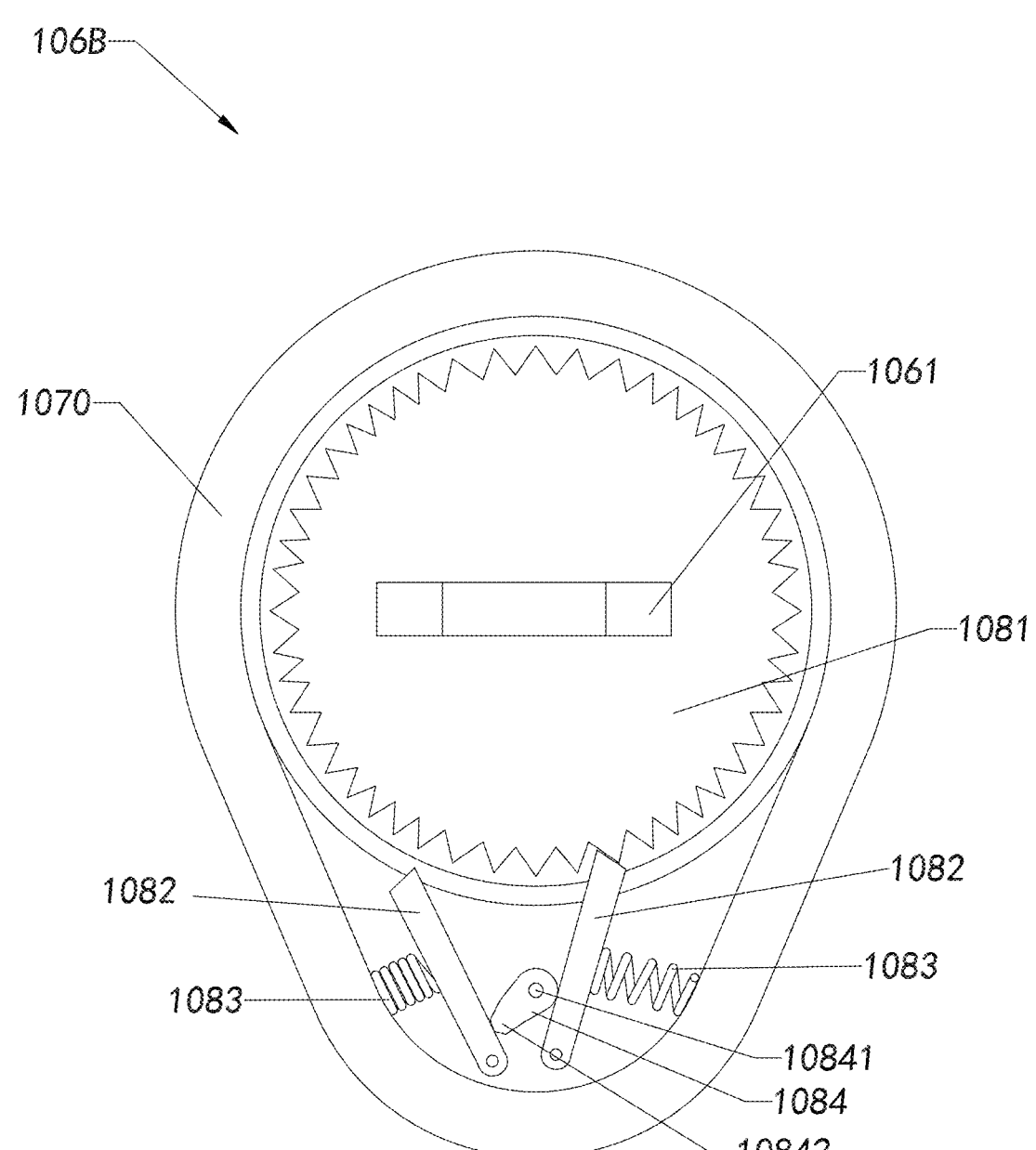
FIG. 30 illustrates a working state of the fixation connector according to the above ninth preferred embodiment of the present invention.
Figure 31:
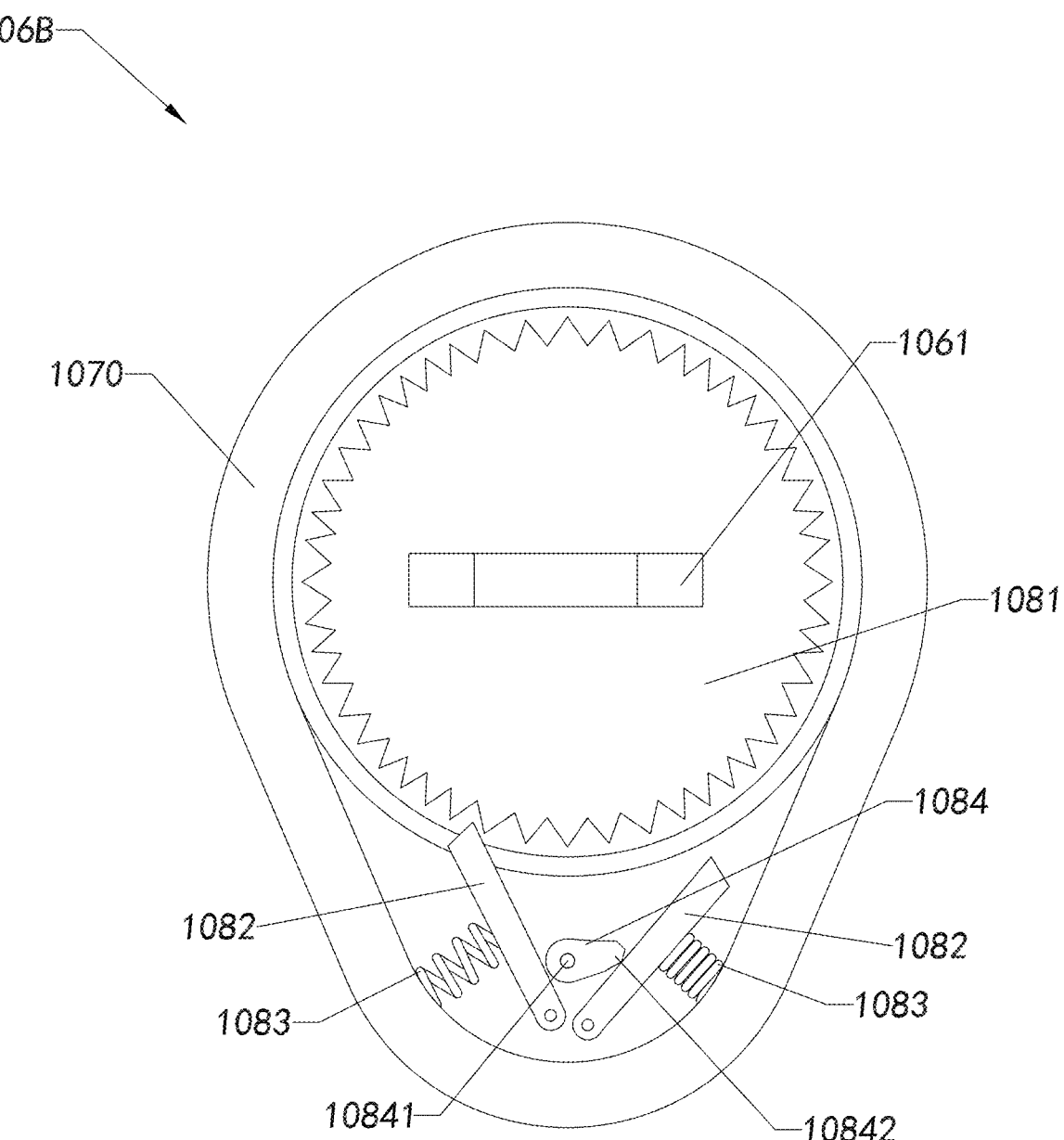
FIG. 31 illustrates another working state of the fixation connector according to the above ninth preferred embodiment of the present invention.

Referring to FIGS. 29 to 31, a fixation connector 106B according to a ninth preferred embodiment of the present invention is illustrated. Unlike the above embodiments, according to this embodiment, the number of the brake members 1082 of the fixation connector 106B is two. The number of the elastic members 1083 is two.

The brake component 1082 is symmetrically arranged on two sides of the reversing component 1084. One end of the brake component 1082 located on the right side of the reversing component 1084 is rotatably mounted on the support plate 1076 of the housing 1070. The other end rests on the ratchet teeth of the ratchet 1081. The brake component 1082 and the ratchet 1081 are in the same plane. The brake component 1082 is in the form of a slender and hard strip, and its width is about the same as the thickness of the ratchet 1081. The brake component 1082 can be connected to the support plate 1076 of the housing 1070 by insertion or through a rotation shaft.

The elastic member 1083 is a spring. One end of the elastic member 1083 on the right side is fixed to the right side of the support plate 1076 of the housing 1070. The other end is elastically biased against the brake member 1082 on the right side, so that the brake member 1082 on the right side is elastically pressed against the ratchet teeth of the ratchet 1081.

One end of the left brake component 1082 is rotatably mounted on the support plate 1076 of the housing 1070. The other end is pressed against the ratchet teeth of the ratchet 1081. One end of the left elastic component 1083 is fixed on the left side of the support plate 1076 of the housing 1070. The other end is elastically biased against the left brake component 1082, so that the left brake component 1082 is elastically pressed against the protruding end 10842 of the reversing component 1084.

In other words, when one end of the brake component 1082 on the right side is against the ratchet teeth of the ratchet 1081, the brake component 1082 on the left side is not against the ratchet 1081. The rotating end 10841 of the reversing component 1084 is against the brake component 1082 on the right side. The protruding end 10842 is biased against the brake component 1082 on the left side. This restricts the direction of rotation of the ratchet 1081 towards the left brake component 1082, so that the ratchet 1081 can only rotate towards the direction of the brake component 1082 on the right side.

When the directional switch 1076 is turned, the protruding end 10842 of the directional component 1084 is rotated to the brake member 1082 on the right side. The brake member 1082 on the right side moves away from the ratchet 1081, while the brake member 1082 on the left side is supported by the elastic component 1084 on the left side and rests against the ratchet 1081 and the rotating end 10841 of the directional component 1084.

At this time, the rotation of the ratchet 1081 towards the brake component 1082 on the right side is restricted. The ratchet 1081 can only rotate towards the brake component 1082 on the left side. In other words, through the switching of the reversing component 1084, the ratchet 1081 can achieve locking in both left and right directions. In other words, the fixation cable 1090 can achieve locking and paragraph style adjustment in both the shortening and side length adjustment dimensions. This adjustment is more stable and accurate. The operation is also very simple, making it convenient to fix the pipelines or surgical instruments needed for surgery.

Figure 32:
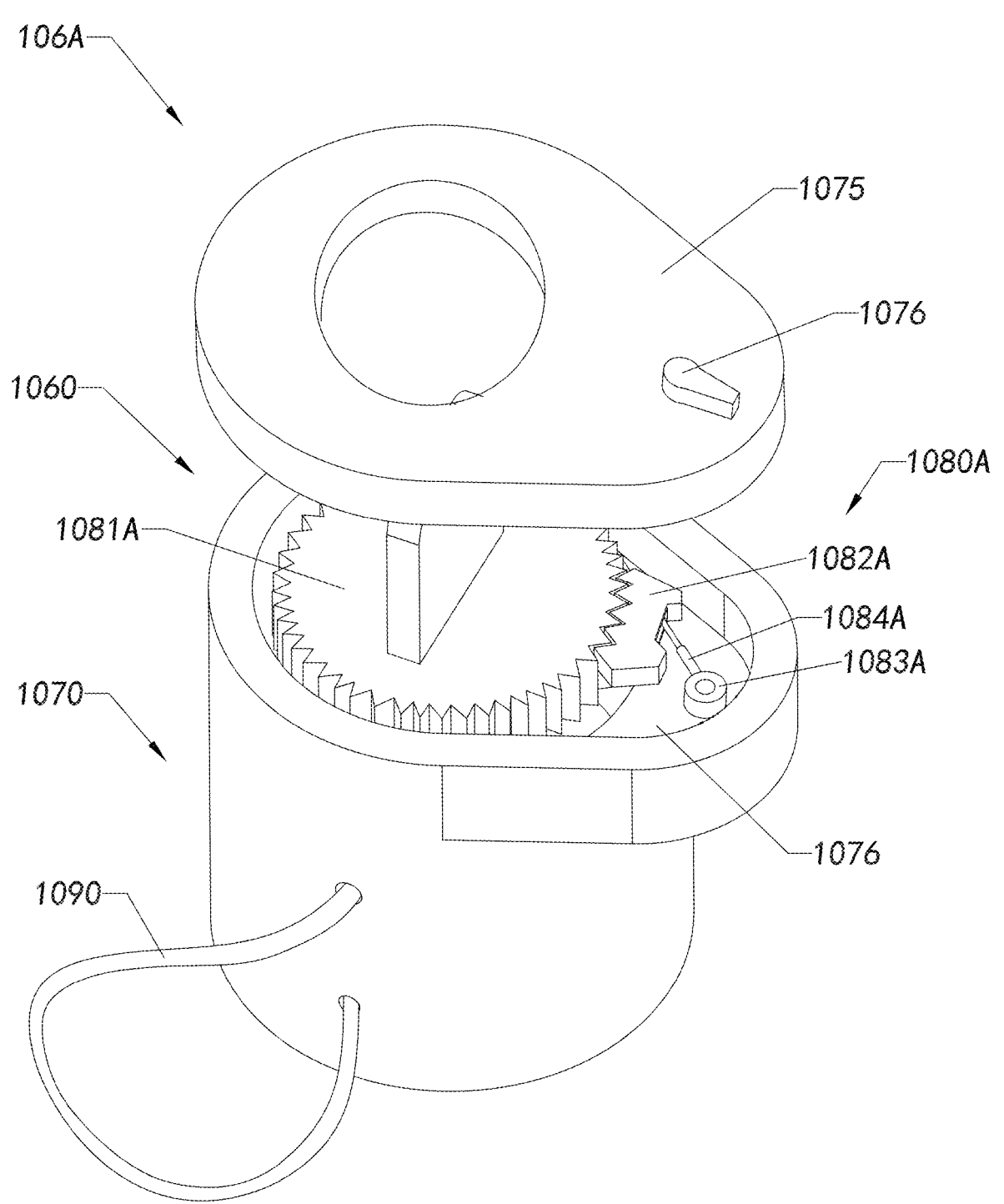
FIG. 32 is a perspective view of a fixation connector according to a tenth preferred embodiment of the present invention.
Figure 33:
FIG. 33 illustrates a working state of the fixation connector according to the above tenth preferred embodiment of the present invention.
Figure 33:
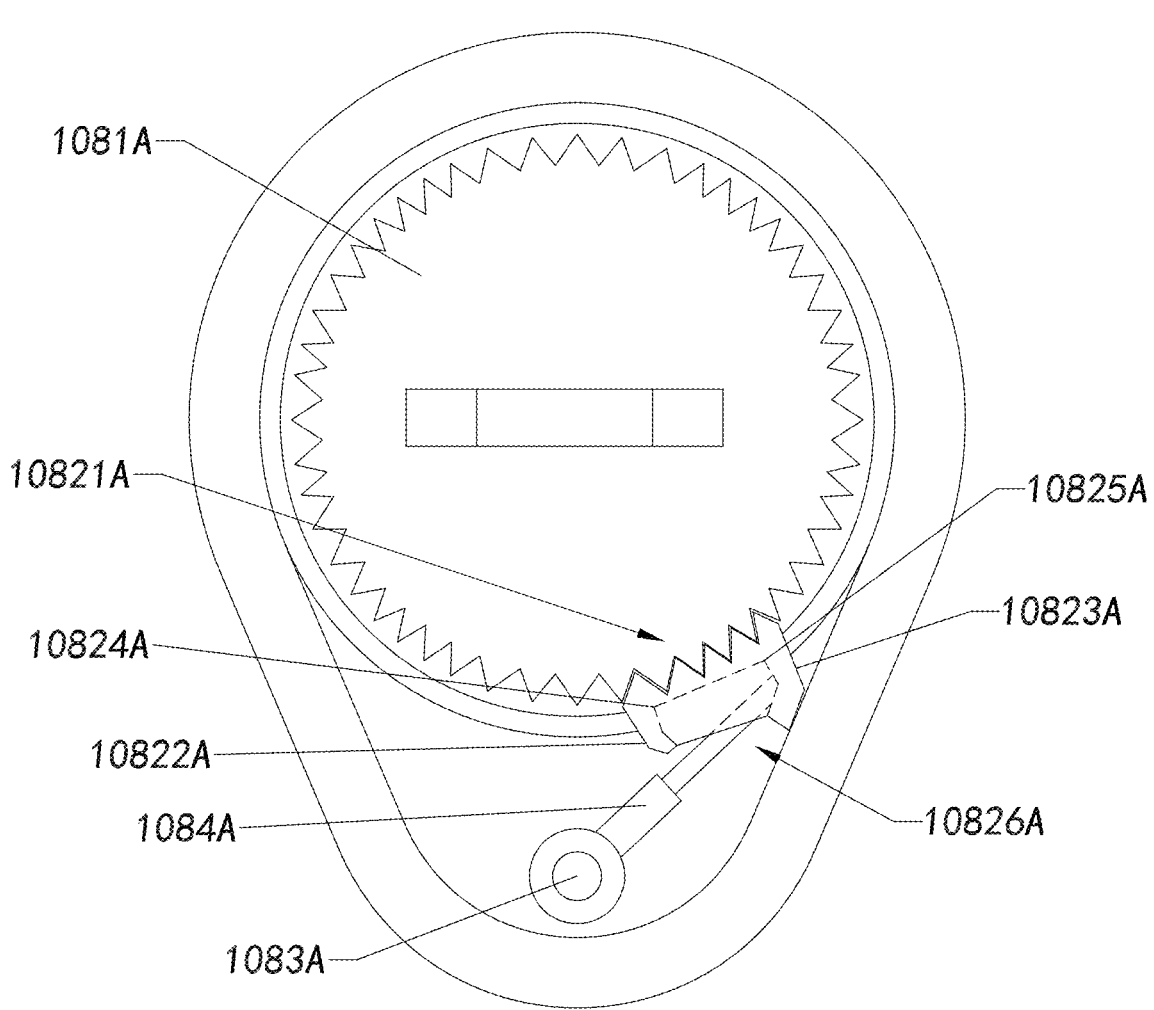
Figure 34:
FIG. 34 illustrates another working state of the fixation connector according to the above tenth preferred embodiment of the present invention . . .
Figure 34:
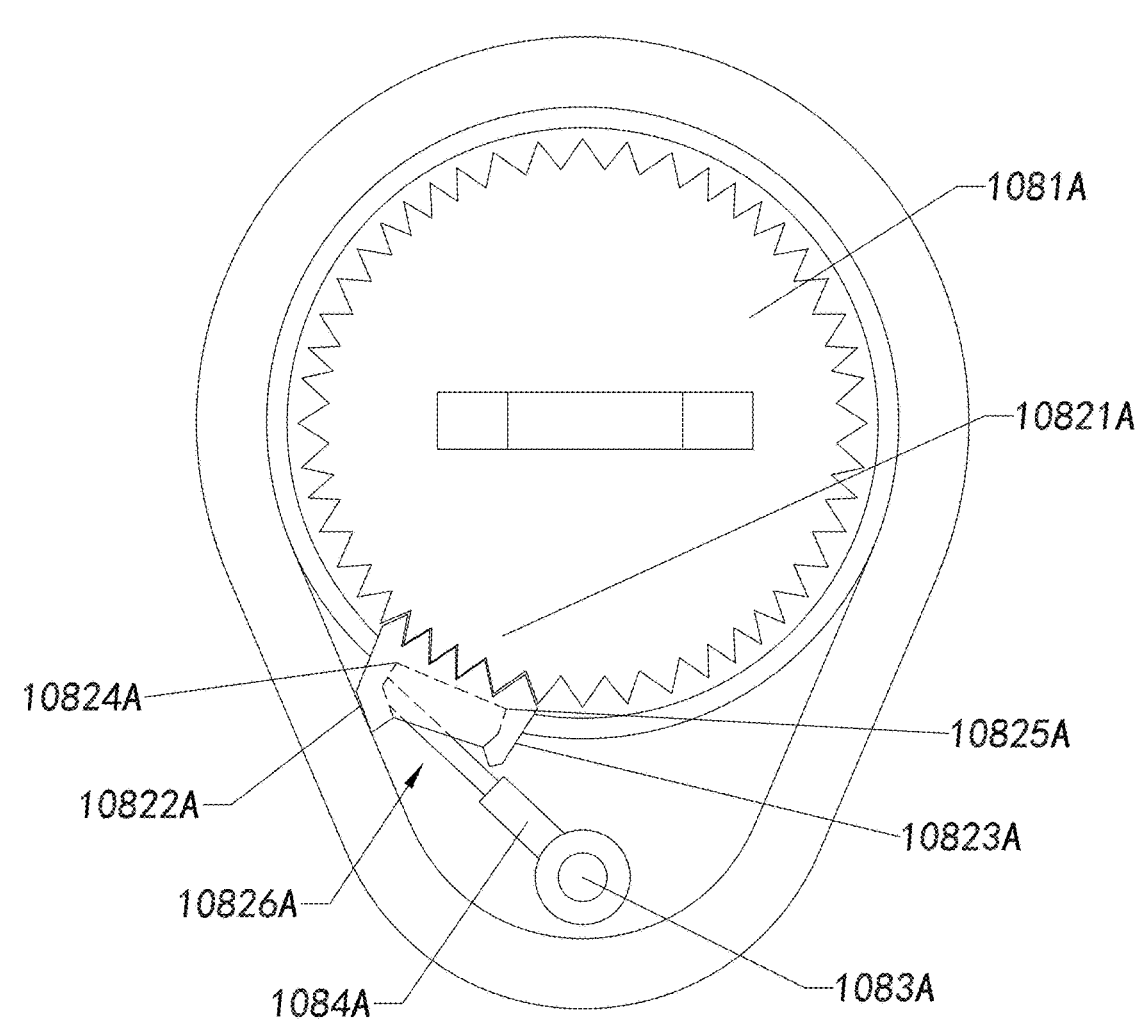

Referring to FIGS. 32 to 34, a fixation connector 106A according to a tenth preferred embodiment of the present invention is illustrated. Unlike the above embodiments, according to this embodiment, the ratchet component 1080A of the fixation connector 106A replaces the ratchet locking component 1080 in the fixation connector 106.

The ratchet component 1080A comprises a ratchet 1081A, a brake block 1082A, a reversing component 1083A, and a top pin 1084A. The top pin 1084A is elastically disposed on the reversing component 1083A and biases the brake block 1082A against the ratchet 1081A. The reversing component 1083A is rotatably disposed on the support plate 1076 of the housing 1070.

In detail, the brake block 1082A is trapezoidal in shape, with a top tooth surface 10821A on one end of the long side to rest against the ratchet 1081A. The top tooth surface 10821A is provided with a tooth groove that fits the corresponding ratchet 1081A, and a groove 10826A is formed inward on the short side. The top pin 1084A is pressed against the groove 10826A to elastically rest the brake block 1082A against the ratchet 1081A.

The top pin 1084A is elastically set on the reversing component 1083A, which means that the top pin 1084A can expand and contract towards the reversing component 1083A. The top pin 1084A rotates with the rotation of the reversing component 1083A.

The two sides of the support plate 1076 are inclined slopes, which decrease from the direction of the ratchet 1081A towards the direction of the reversing component 1083A to fit the inclined edge of the brake pad 1082A.

There are two contact points 10824A and 10825A in the groove 10826A of the brake block 1082A. The first contact point 10824A is close to the left side 10822A of the brake block 1082A. The second contact point 10825A is close to the right side 10823A of the brake block 1082A.

When the reversing component 1083A turns to the right, the top pin 1084A presses against the second contact point 10824A of the brake block 1082A, thereby elastically pressing the top tooth surface 10821A of the brake block 1082A against the ratchet 1081A, and causing the right side surface 10823A of the brake block 1082A to adhere to the right wall of the support plate 1076.

At this time, when the ratchet 1081A rotates to the right, it drives the brake block 1082A to move to the right. The right side surface 10823A of the brake block 1082A tightly adheres to the right wall of the pallet 1076 under the action of force, thereby restricting the ratchet 1081A from rotating to the right.

When the ratchet 1081A rotates to the left, it drives the brake block 10824A to move to the left. The ratchet teeth of the ratchet 1081A press down on the brake block 1082A. The brake block 1082A presses down on the top pin 1084A to disengage the ratchet teeth. The ratchet 1081A completes its rotation, and after the ratchet 1081A rotates, the brake block 1082A is elastically supported by the top pin 1084A on the ratchet 1081A, maintaining a locked state.

At this time, the ratchet 1081A can only rotate in one direction, In other words, move towards the left. Similarly, when the reversing component 1083A is turned to the left, the top pin 1084A presses against the first contact point 10824A of the brake block 1082A, thereby elastically pressing the top tooth surface 10821A of the brake block 1082A against the ratchet 1081A, and causing the left side surface 10822A of the brake block 1082A to adhere to the left wall of the support plate 1076.

At this time, when the ratchet 1081A rotates to the left, it drives the brake block 1082A to move to the left. The left side surface 10822A of the brake block 1082A tightly adheres to the left wall of the pallet 1076 under the action of force, thereby restricting the ratchet 1081A from rotating to the left.

When the ratchet 1081A rotates to the right, it drives the brake block 10824A to move to the right. The ratchet teeth of the ratchet 1081A press down on the brake block 1082A. The brake block 1082A presses down on the top pin 1084A to disengage the ratchet teeth. The ratchet 1081A completes its rotation, and after the ratchet 1081A rotates, the brake block 1082A is elastically supported by the top pin 1084A on the ratchet 1081A, maintaining a locked state. At this time, the ratchet 1081A can only rotate in one direction, In other words, move towards the right side.

It is worth mentioning that the tooth rotation of the ratchet 1081A is segmented, In other words, for each tooth rotation of the ratchet 1081A, the length of the fixation cable 1090 changes slightly. The changed length can also be locked, which is limited by the brake component 1082A, so that the fixation cable 1090 can be fixed in the appropriate position. One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and are subject to change without departure from such principles. Therefore, this invention includes all modifications encompassed within the spirit and scope of the following claims.

What is claimed is:

1. A head brace with an adjustable-length connector, comprising:

a connector comprising an outer cover body, an inner core body, a reversible structure, and a fixation rope body, wherein said outer cover body is suitable for being sleeved on the outer end of said inner core body, wherein said reversible structure is installed on said inner core body, wherein said fixation rope body is suitable for being connected to said outer cover body and said inner core body, so as to tighten said fixation rope body by the forward rotation of said inner core body relative to said outer cover body, and to relax said fixation rope body by a reverse rotation of said inner core body relative to said outer cover body through said reversible structure, so as to realize the adjustable length of said fixation rope body of said connector; and a head brace comprising a guidance adapter and a head clamp, wherein said guidance adapter is suitable for being installed on said head clamp, wherein said connector is suitable for being installed on said head clamp through said guidance adapter:

wherein said inner core body comprises a fixation member and a grip member, wherein said fixation member is integrally connected to said grip member;

wherein said outer cover body has an inner core accommodation cavity, wherein said fixation member of said inner core body is suitable for being accommodated in said outer cover body through said inner core accommodation cavity of said outer cover body:

wherein said outer cover body has a first fixation hole, a second fixation hole, and a third fixation hole, wherein said first fixation hole, said second fixation hole, wherein said third fixation hole are located on the side end of said outer cover body, wherein said first fixation hole and said second fixation hole are on one side of said outer cover body, wherein said third fixation hole is on the other side of said outer cover body, wherein said first fixation hole and said third fixation hole are on the same axis.

2. The head brace, as recited in claim 1, wherein said fixation member has a first fixation groove and a second fixation groove, wherein said first fixation groove and said second fixation groove are located on the side end of said fixation member, recessed on the surface of the side end of said fixation member, wherein said fixation member further has a first inner hole and a second inner hole, wherein said first inner hole and said second inner hole are respectively located at the bottom of said first fixation groove and said second fixation groove, and horizontally penetrate said fixation member, wherein said first inner hole is on the same axis as said first fixation hole and said third fixation hole, wherein said second inner hole is on the same axis as said second fixation hole, wherein one end of said fixation rope body is suitable for passing through said first fixation hole, said first inner hole, and said third fixation hole, wherein the other end of said fixation rope body is suitable for passing through said second fixation hole and said second inner hole, so that when said inner core body rotates relative to said outer cover body, the two ends of said fixation rope body are respectively wound around said first fixation groove and said second fixation groove, so that the length of said fixation rope is continuously reduced, thereby fixing the medical device on the outer wall of said outer cover body.

3. The head brace, as recited in claim 2, wherein said outer cover body has a clamping groove, which is located on said inner wall of said outer cover body, recessed on said inner wall of said outer cover body and communicating with said inner core accommodation cavity.

4. The head brace, as recited in claim 3, wherein said reversible structure comprises a control member and a connection unit, wherein said control member is installed on said grip member, wherein said clamping member is installed on said fixation member, wherein said clamping member is suitable for engaging with said clamping groove of said outer cover body to achieve fixation.

5. The head brace, as recited in claim 4, wherein said reversible structure further comprises a connection unit, wherein one end of said connection unit is connected to said clamping member, wherein the other end of said connection unit is connected to said control member, so as to drive the movement of said clamping member through said connection unit connected to said control member by controlling the movement of said control member, so as to realize the engagement and separation of said clamping member and said clamping groove, and thus realize the reversible rotation of said inner core body.

6. The head brace, as recited in claim 5, wherein said reversible structure further comprises an elastic element, wherein one end of said elastic element is connected to said clamping member or said connection unit, wherein the other end of said elastic element is connected to said inner core body.

7. The head brace, as recited in claim 6, wherein said fixation member further has an installation hole, wherein said clamping member is suitable for being installed on said fixation member through said installation hole.

* * * * *